US011147809B2

(12) United States Patent
Chen

(10) Patent No.: US 11,147,809 B2
(45) Date of Patent: Oct. 19, 2021

(54) METHODS OF TREATING NEUROFIBROMATOSIS WITH PERILLYL ALCOHOL

(71) Applicant: NeOnc Technologies, Inc., Los Angeles, CA (US)

(72) Inventor: Thomas Chen, La Canada, CA (US)

(73) Assignee: NeOnc Technologies, Inc., Los Angeles, CA (US)

( * ) Notice: Subject to any disclaimer, the term of this patent is extended or adjusted under 35 U.S.C. 154(b) by 0 days.

(21) Appl. No.: 16/313,388

(22) PCT Filed: Jun. 30, 2017

(86) PCT No.: PCT/US2017/040338
§ 371 (c)(1),
(2) Date: Dec. 26, 2018

(87) PCT Pub. No.: WO2018/005994
PCT Pub. Date: Jan. 4, 2018

(65) Prior Publication Data
US 2019/0167669 A1    Jun. 6, 2019

Related U.S. Application Data

(63) Continuation-in-part of application No. 15/291,847, filed on Oct. 12, 2016, now abandoned, which is a (Continued)

(51) Int. Cl.
*A61K 31/495* (2006.01)
*C07D 231/12* (2006.01)
(Continued)

(52) U.S. Cl.
CPC .......... *A61K 31/495* (2013.01); *A61K 9/0043* (2013.01); *A61K 31/045* (2013.01); (Continued)

(58) Field of Classification Search
CPC .. A61K 47/55; A61K 31/4188; A61K 31/045; A61K 31/415
See application file for complete search history.

(56) References Cited

U.S. PATENT DOCUMENTS

| 2013/0203828 A1 | 8/2013 | Chen et al. |
| 2013/0331422 A1 | 12/2013 | Chen et al. |
| 2014/0235631 A1 | 8/2014 | Bunt et al. |

FOREIGN PATENT DOCUMENTS

| WO | WO-2009040420 A2 * | 4/2009 | ............. A61K 47/44 |
| WO | 2016040656 | 3/2016 | |

OTHER PUBLICATIONS

International Search Report and Written Opinion dated Jun. 30, 2017 corresponding to International Patent Application No. PCT/US17/40338, 15 pages.

* cited by examiner

*Primary Examiner* — San Ming R Hui
(74) *Attorney, Agent, or Firm* — Leason Ellis LLP

(57) ABSTRACT

The present methods treat neurofibromatosis by a administering to a subject perillyl alcohol or iso-perillyl alcohol. The present methods also treat neurofibromatosis by administering to a subject a carbamate of perillyl alcohol, or a carbamate of iso-perillyl alcohol. The perillyl alcohol carbamate may comprise perillyl alcohol conjugated with rolipram or temozolomide.

28 Claims, 20 Drawing Sheets

Related U.S. Application Data continuation of application No. 13/818,972, filed as application No. PCT/US2011/049392 on Aug. 26, 2011, now Pat. No. 9,499,461.

(60) Provisional application No. 62/357,545, filed on Jul. 1, 2016, provisional application No. 61/471,402, filed on Apr. 4, 2011, provisional application No. 61/377,747, filed on Aug. 27, 2010.

(51) Int. Cl.
| | | |
|---|---|---|
| *A61K 31/4188* | (2006.01) | |
| *A61K 47/54* | (2017.01) | |
| *C07B 59/00* | (2006.01) | |
| *A61K 31/4015* | (2006.01) | |
| *A61K 9/00* | (2006.01) | |
| *A61K 31/045* | (2006.01) | |
| *A61K 31/415* | (2006.01) | |
| *C07D 207/26* | (2006.01) | |
| *C07C 33/14* | (2006.01) | |
| *C07D 487/04* | (2006.01) | |
| *A61K 45/06* | (2006.01) | |
| *A61N 5/10* | (2006.01) | |
| *A61K 31/635* | (2006.01) | |
| *A61K 47/55* | (2017.01) | |
| *A61K 31/366* | (2006.01) | |

(52) U.S. Cl.
CPC ........ *A61K 31/366* (2013.01); *A61K 31/4015* (2013.01); *A61K 31/415* (2013.01); *A61K 31/4188* (2013.01); *A61K 31/635* (2013.01); *A61K 45/06* (2013.01); *A61K 47/54* (2017.08); *A61K 47/542* (2017.08); *A61K 47/543* (2017.08); *A61K 47/55* (2017.08); *A61N 5/10* (2013.01); *C07B 59/00* (2013.01); *C07C 33/14* (2013.01); *C07D 207/26* (2013.01); *C07D 231/12* (2013.01); *C07D 487/04* (2013.01); *C07B 2200/05* (2013.01); *C07C 2601/16* (2017.05)

Perillyl alcohol (POH) effect on GTP-Ras in Neurofibromatosis type 1 (NF1 mutation)

NF1 : ATCC CRL-2884
(Human Schwann Cell NF1)

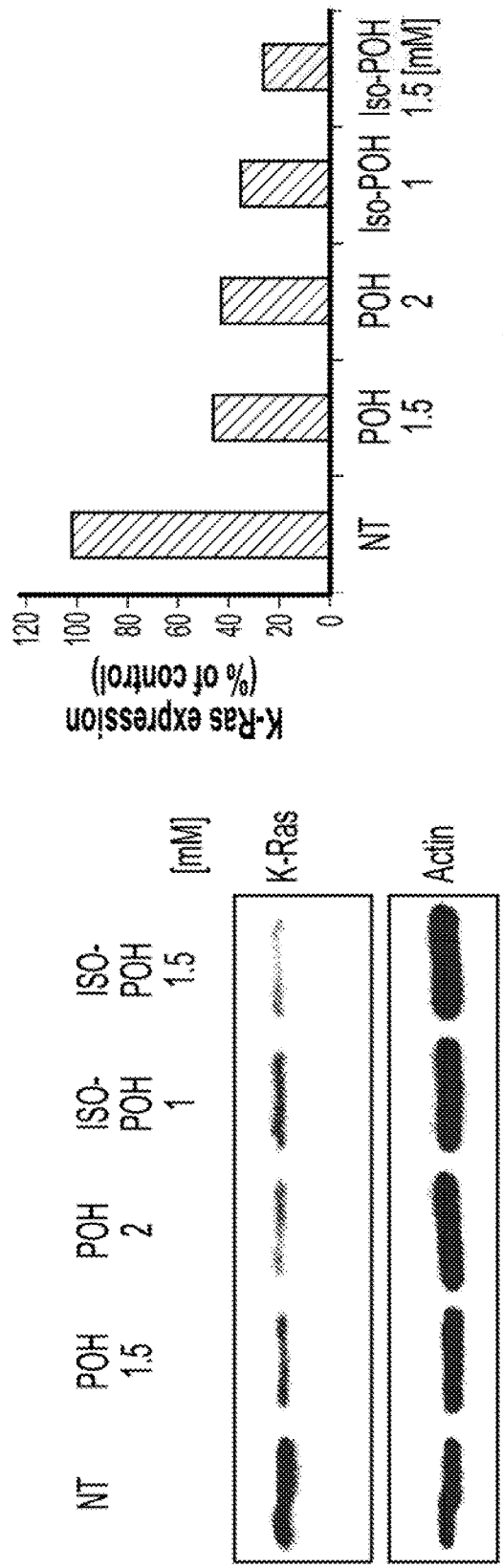
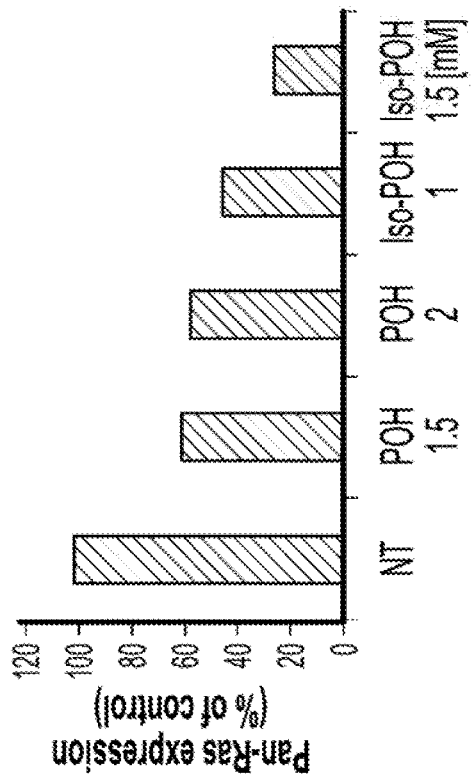
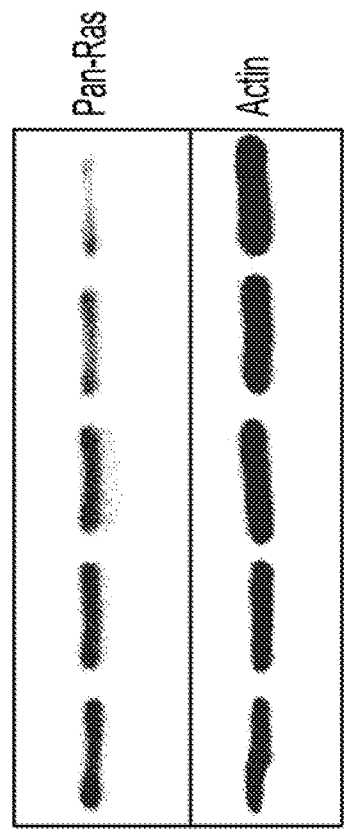
FIG. 21A
FIG. 21B
FIG. 21C

NF1-GM23312 : Tumor derived cell line from chest

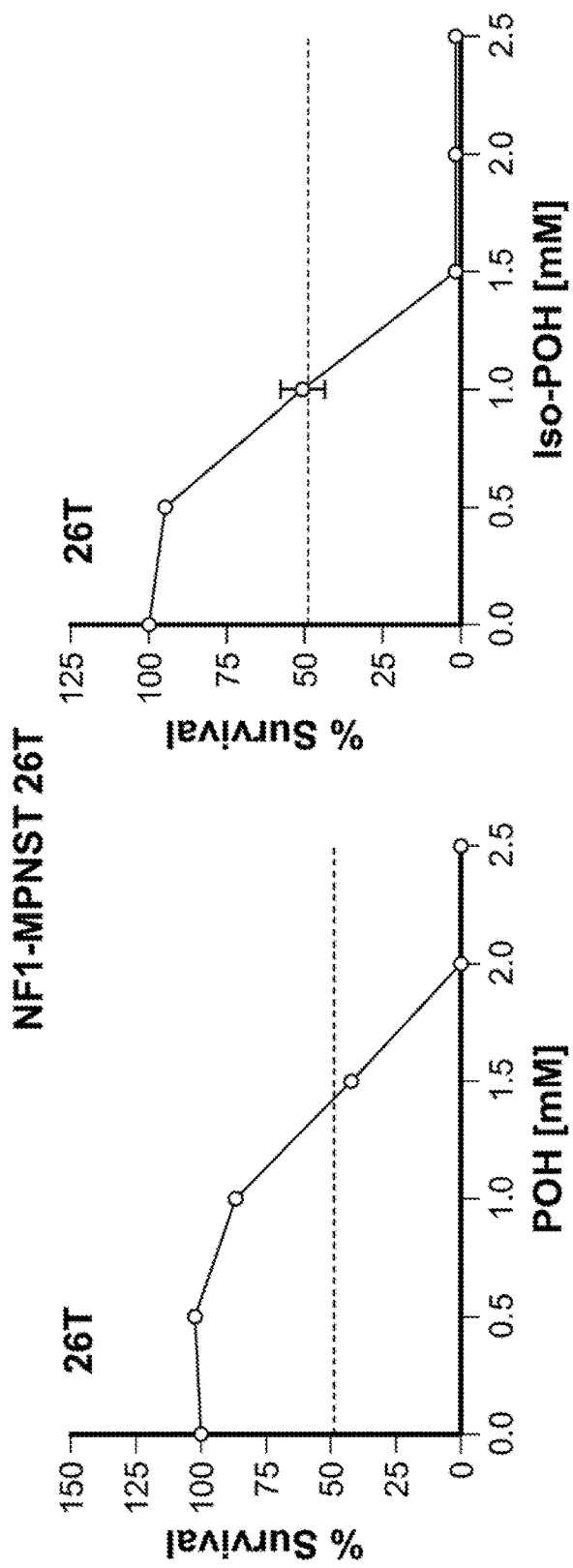
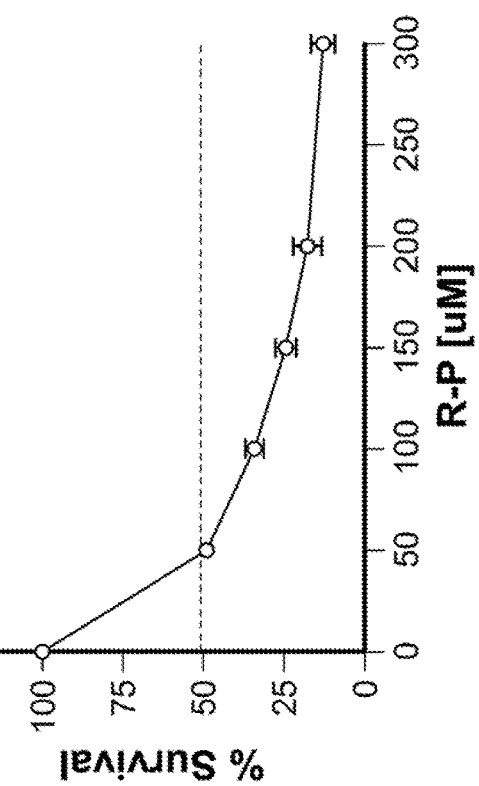

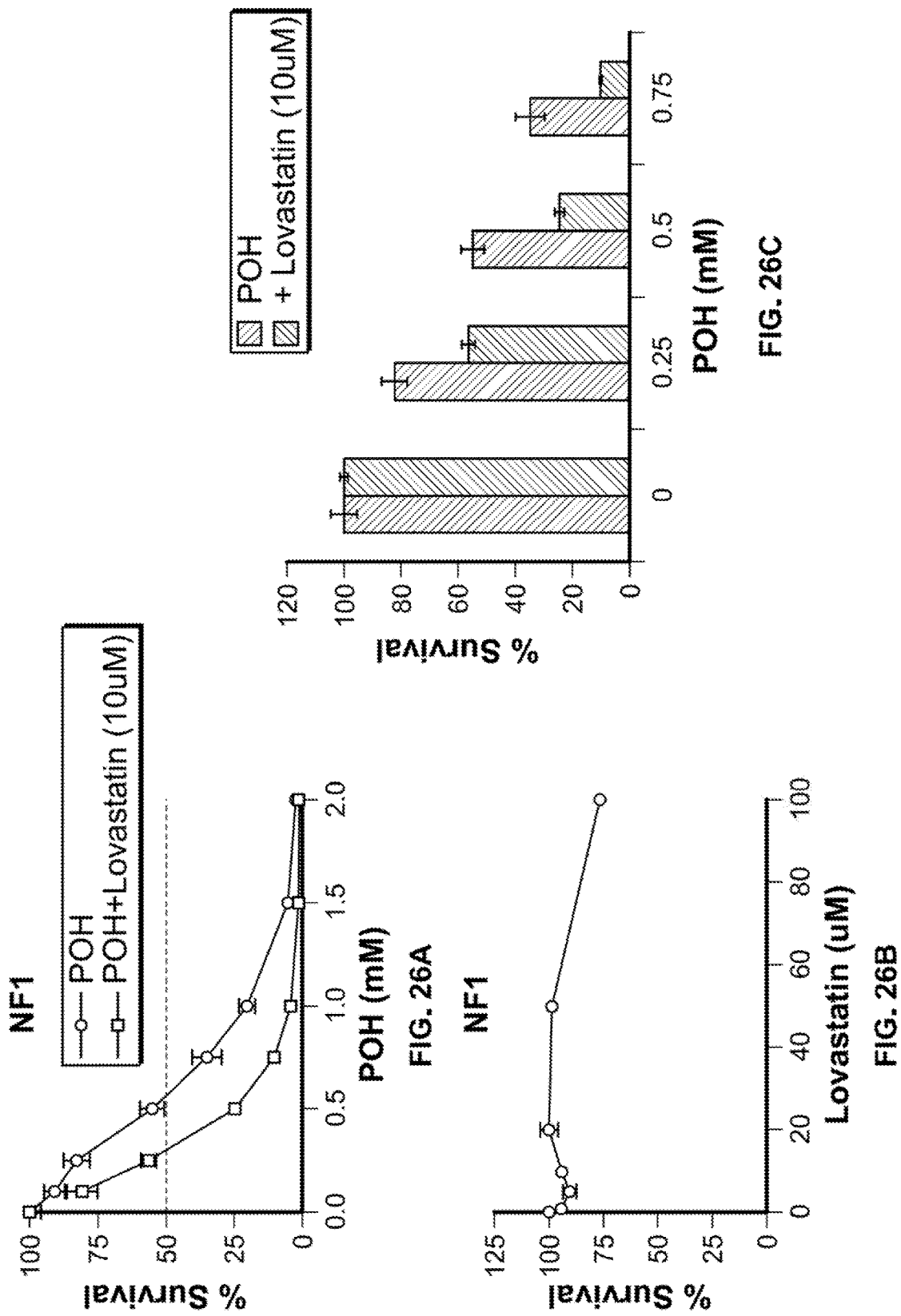

METHODS OF TREATING NEUROFIBROMATOSIS WITH PERILLYL ALCOHOL

FIELD OF THE INVENTION

The present invention relates to methods of treating neurofibromatosis by the administration of perillyl alcohol (POH), iso-perillyl alcohol, or POH derivatives.

BACKGROUND OF THE INVENTION

Neurofibromatosis type 1 ("NF-1") is a tumor disorder that is caused by the mutation of a gene on chromosome 17 that is responsible for controlling cell division. NF-1 causes tumors along the nervous system and can grow anywhere on the body. Common symptoms of NF-1 include brownish-red spots in the colored part of the eye called Lisch nodules, benign skin tumors called neurofibromas, and larger benign tumors of nerves called plexiform neurofibromas, scoliosis (curvature of the spine), learning disabilities, vision disorders, mental disabilities, multiple café au lait (TCL, name of specifics spots) spots and epilepsy. NF-1 was formerly known as von Recklinghausen disease. There is no cure for the disorder itself. Instead, patients with neurofibromatosis are monitored by a team of specialists to manage symptoms and/or complications.

Malignant gliomas, the most common form of central nervous system (CNS) cancers, is currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359: 492-507, 2008. Stupp et al. Radiotherapy plus concomitant and adjuvant temozolomide for glioblastoma. *New England J Med.* 352: 987-996, 2005.

The poor response of tumors, including malignant gliomas, to various types of chemotherapeutic agents are often due to intrinsic drug resistance. Additionally, acquired resistance of initially well-responding tumors and unwanted side effects are other problems that frequently thwart long-term treatment using chemotherapeutic agents. Hence, various analogues of chemotherapeutic agents have been prepared in an effort to overcome these problems. The analogues include novel therapeutic agents which are hybrid molecules of at least two existing therapeutic agents. For example, cisplatin has been conjugated with Pt-(II) complexes with cytotoxic codrugs, or conjugated with bioactive shuttle components such as porphyrins, bile acids, hormones, or modulators that expedite the transmembrane transport or the drug accumulation within the cell. (6-Aminomethylnicotinate) dichloridoplatinum(II) complexes esterified with terpene alcohols were tested on a panel of human tumor cell lines. The terpenyl moieties in these complexes appeared to fulfill a transmembrane shuttle function and increased the rate and extent of the uptake of these conjugates into various tumor cell lines. Schobert et al. Monoterpenes as Drug Shuttles: Cytotoxic (6-minomethylnicotinate) dichloridoplatinum(II) Complexes with Potential To Overcome Cisplatin Resistance. *J. Med. Chem.* 2007, 50, 1288-1293.

Perillyl alcohol (POH), a mutually occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. *Environ Health Perspect.* 1997 June; 105 (Suppl 4): 977-979. Hybrid molecules containing both perillyl alcohol and retinoids were prepared to increase apoptosis-inducing activity. Das et al. Design and synthesis of potential new apoptosts agents: hybrid compounds containing perillyl alcohol and new constrained retinoids. *Tetrahedron Letters* 2010, 51, 1462-1466.

There is still a need to prepare perillyl alcohol derivatives including perillyl alcohol conjugated with other therapeutic agents, and use this material in the treatment of cancers such as malignant gliomas, as well as other brain disorders such as Parkinson's and Alzheimer's disease. Perillyl alcohol derivatives may be administered alone or in combination with other treatment methods including radiation, standard chemotherapy, and surgery. The administration can also be through various routes including intranasal, oral, oral-tracheal for pulmonary delivery, and transdermal.

SUMMARY

The present disclosure provides for a method of treating neurofibromatosis in a subject (suffering from neurofibromatosis). In certain embodiments, the method comprises administering to the subject a therapeutically effective amount of perillyl alcohol (POH) or an iso-perillyl alcohol (iso-POH), or a combination thereof. In certain embodiments, the method comprises administering to the subject a therapeutically effective amount of a carbamate of perillyl alcohol (a perillyl alcohol carbamate), a carbamate of an iso-perillyl alcohol (an iso-perillyl alcohol carbamate), or a combination thereof.

The present disclosure provides for a method of inhibiting or decreasing Ras level and/or activity in a cell. In certain embodiments, the method comprises administering to the cell a therapeutically effective amount of perillyl alcohol (POH) or an iso-perillyl alcohol (iso-POH), or a combination thereof. In certain embodiments, the method comprises administering to the cell a therapeutically effective amount of a carbamate of perillyl alcohol (a perillyl alcohol carbamate), a carbamate of an iso-perillyl alcohol (an iso-perillyl alcohol carbamate), or a combination thereof.

The present disclosure provides for a method of inhibiting or decreasing Ras level and/or activity in a subject. In certain embodiments, the method comprises administering to the subject a therapeutically effective amount of perillyl alcohol (POH) or an iso-perillyl alcohol (iso-POH), or a combination thereof. In certain embodiments, the method comprises administering to the subject a therapeutically effective amount of a carbamate of perillyl alcohol (a perillyl alcohol carbamate), a carbamate of an iso-perillyl alcohol (an iso-perillyl alcohol carbamate), or a combination thereof.

In certain embodiments, the method further composes administering temozolomide or rolipram.

In certain embodiments, the method further comprises administering a statin.

Non-limiting examples of statin include atorvastatin, fluvastatin, lovastatin, pitavastatin, pravastatin, simvastatin and rosuvastatin.

In certain embodiments, the method further comprises administering prostratin.

In certain embodiments, the administration is by inhalation, intranasally, orally, intravenously, subcutaneously or intramuscularly.

Non-limiting examples of isoperillyl alcohol include (4-isopropylidene cyclohex-1-enyl)methanol, (4-isopropyl cyclohexa-1,3-dienyl)methanol, (4-isopropyl cyclohexa-1,4-dienyl)methanol, (4-isopropylphenyl)methanol and (4-isopropenylphenyl)methanol.

In certain embodiments, the perillyl alcohol carbamate is perillyl alcohol conjugated with temozolomide or rolipram. In certain embodiments, the perillyl alcohol carbamate is 3-methyl 4-oxo-3,4-dihydroimidazo[5,1-d][1,2,3,5]tetrazine-8-carbonyl[[)]]-carbamic acid-4-isopropenyl cyclohex-1-enylmethyl ester. In certain embodiments, the perillyl alcohol carbamate is 4-(3-cyclopentyloxy-4-methoxy phenyl)-2-oxo-pyrrolidine-1-carboxylic acid 4-isopropenyl cyclohex-1-enylmethyl ester.

POH carbamates encompassed by the present disclosure include, but are not limited to, 4-bis-N,N'-4-isopropenyl cyclohex-1-enylmethyloxy carbonyl [5-(2,5-dimethyl phenyl)-3-trifluoromethyl pyrazol-1-yl] benzenesulfonamide, 4-(3-cyclopentyloxy-4-methoxy phenyl)-2-oxo-pyrrolidine-1-carboxylic acid 4-isopropenyl cyclohex-1-enylmethyl ester, and (3-methyl 4-oxo-3,4-dihydroimidazo[5,1-d][1,2,3,5]tetrazine-8-carbonyl)carbamic acid-4-isopropenyl cyclohex-1-enylmethyl ester.

Iso-POH carbamates encompassed by the present invention include, but are not limited to, (3-Methyl 4-oxo-3,4-dihydroimidazo[5,1-d][1,2,3,5]tetrazine-8-carbonyl)-carbamic acid-4-isopropylidene cyclohex-1-enylmethyl ester, 4-(3-Cyclopentyloxy-4-methoxyphenyl)-2-oxo-pyrrolidine-1-carboxylic acid 4-isopropylidene cyclohex-1-enylmethyl ester, 4-(Bis-N,N'-4-isopropylidene cyclohex-1-enylmethyloxy carbonyl [5-(2,5-dimethyl phenyl)-3-trifluoromethyl pyrazol-1-yl]benzenesulfonamide.

The present disclosure further provides for a pharmaceutical composition comprising a perillyl alcohol carbamate. The perillyl alcohol carbamate may be perillyl alcohol conjugated with a therapeutic agent, such as a chemotherapeutic agent. The chemotherapeutic agents that may be used in the present invention include a DNA alkylating agent, a topoisomerase inhibitor, an endoplasmic reticulum stress inducing agent, a platinum compound, an antimetabolite, an enzyme inhibitor, and a receptor antagonist. In certain embodiments, the therapeutic agents are dimethyl celocoxib (DMC), temozolomide (TMZ) or rolipram. The perillyl alcohol carbamates may be 4-Bis-N,N'-4-isopropenyl cyclohex-1-enylmethyloxy carbonyl [5-(2,5-dimethyl phenyl)-3-trifluoromethyl pyrazol-1-yl] benzenesulfonamide, 4-(3-cyclopentyloxy-4-methoxy phenyl)-2-oxo-pyrrolidine-1-carboxylic acid 4-isopropenyl cyclohex-1-enylmethyl ester, and 3-methyl 4-oxo-3,4-dihydroimidazo[5,1-d][1,2,3,5]tetrazine-8-carbonyl)-carbamic acid-4-isopropenyl cyclohex-1-enylmethyl ester.

The pharmaceutical compositions of the present disclosure may be administered before, during or after radiation. The pharmaceutical compositions may be administered before, during or after the administration of a chemotherapeutic agent. The routes of administration of the pharmaceutical compositions include inhalation, intranasal, oral, intravenous, subcutaneous or intramuscular administration.

The disclosure further provides for a method for treating a disease in a mammal, comprising the step of delivering to the mammal a therapeutically effective amount of a perillyl alcohol carbamate. The method may further comprise the step of treating the mammal with radiation, and/or further comprise the step of delivering to the mammal a chemotherapeutic agent. The diseases treated may be cancer, including a tumor of the nervous system, such as a glioblastoma. The routes of administration of the perillyl alcohol carbamate include inhalation, intranasal, oral, intravenous, subcutaneous or intramuscular administration.

BRIEF DESCRIPTION OF THE DRAWINGS

FIG. 9A shows the images of subcutaneous U-87 gliomas in nude mice treated with butyryl-POH, purified (S)-perillyl alcohol having a purity greater than 98.5% ("Purified POH"), POH purchased from Sigma chemicals ("Sigma"), or phosphate buffered saline ("PBS"; negative control). FIG. 9B shows average tumor growth over time (total time period of 60 days).

FIG. 20A: cytotoxicity of POH on NF1 cells; FIG. 20B: cytotoxicity of RP-POH on NF1 cells; FIG. 20C: cytotoxicity of POH on Panel cells.

FIGS. 21A-21C show results from Ras Binding Domain (RBD) Pulldown Assays in lysates of Panel cells with or without treatments of POH and iso-POH at different concentrations. FIG. 21A is Western blots showing the results from RBD Pulldown Assays in lysates of Panel cells with or without treatments of POH and iso-POH. FIG. 21B shows bar graphs of the K-Ras levels of the Western blots. FIG. 21C shows bar graphs of the Pan-Ras levels of the Western blots.

FIGS. 23A-23C show the cytotoxicity of POH (FIG. 23A), iso-POH (FIG. 23B) and RP-POH (FIG. 23C, R-P) on NF1-MPNST 26T cells.

FIG. 25C are bar graphs showing the cytotoxicity of POH, and POH+ prostratin on NF1-MPNST 26T cells.

FIGS. 26A-26C show the cytotoxicity of POH, POH in combination with lovastatin (FIG. 26A), and lovastatin (FIG. 26B) on NF1-MPNST 26T cells. FIG. 25C are bar graphs showing the cytotoxicity of POH, and POH prostratin on NF1-MPNST 26T cells.

DETAILED DESCRIPTION

Figure 1:
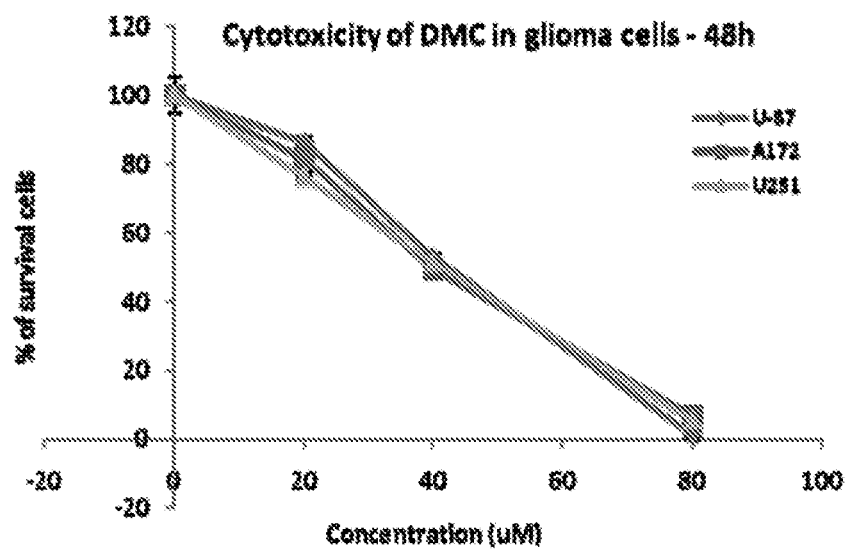
FIG. 1 shows the results of the MTT cytotoxicity assays demonstrating the efficacy of dimethyl celecoxib (DMC) in killing U87, A172 and U251 human glioma cells.

The present invention provides methods of inhibiting Ras expression, or of treating neurofibromatosis by administering POH or iso-POH to a mammal in need of such treatment. In some embodiments, the POH or iso-POH is administered alone with rolipram ("RP"). In some embodiments, a statin is also administered. Statins include atorvastatin, fluvastatin, lovastatin, pitavastatin, pravastatin, simvastatin and rosuvastatin.

The POH or iso-POH may be administered with rolipram or a statin, or with both. Such administration may be by co-administration of distinct drug products, each containing only one of said POH, iso-POH, rolipram and/or statin. Alternatively, said POH iso-POH rolipram and/or statin may be administered in a fixed dose combination drug product. Alternatively, the desired combination of drug substances may be dosed as a conjugate with POH or iso-POH, with or without other drug products.

The present methods and compounds can be used to treat neurofibromatosis. Neurofibromatosis may include three types, neurofibromatosis type 1 (NF1), neurofibromatosis type 2 (NF2), and schwannomatosis. In certain embodiments, NF1 and NF2 are inherited disorders and both encompass mutations which predispose individuals to multiple tumors of the central or peripheral nervous system, and occasionally to other malignancies. In certain embodiments, major tumor types associated with NF1 and NF2 involve glial cells (e.g. Schwann cells and astrocytes). In certain embodiments, the tumors of neurofibromatosis are neurofibromas (tumors of the peripheral nerves), and/or tumors of Schwann cells.

Neurofibromatosis Type 2

In certain embodiments, neurofibromatosis type 2 (NF2) is characterized by multiple tumors on the cranial and spinal nerves. In certain embodiments, individuals with NF2 are at a high risk for developing brain tumors, in particular tumors on both the seventh and eighth cranial nerves, such as bilateral vestibular schwannomas, a type of tumor which occurs on these nerves. In certain embodiments, hearing loss, ringing in the ears, and problems with balance are symptoms frequently associated with NF2. Schwannomas are tumors consisting of nerve sheath cells or Schwann cells (SCs). In certain embodiments, NF2 involves bilateral vestibular schwannomas, also known as acoustic neuromas, as well as spinal schwannomas and schwannomas of the peripheral nerves. In addition to schwannomas, individuals with NF2 may develop other types of tumors emanating from the nerves, meningeal envelopes brain and spinal cord. In certain embodiments, the tumor is meningioma, ependymomas and/or astrocytomas. In certain embodiments, NF2 patients may have an increased risk for developing mesotheliomas.

In certain embodiments, NF2 results from a mutation or a deletion of the NF2 gene (Sainz et al. 1994, Hum. Mol. Genet. 3: 885-891; Ruttledge et al., 1994, Nat. Genet. 6: 180-184; Rubio et al., 1994, Cancer Res. 54: 45-47; Huynh et al., 1997, J. Neuropathol Exp. Neurol. 56: 382-390). The NF2 gene is a tumor suppressor gene that encodes a protein, Merlin. Merlin belongs to the ezrin, radixin, and moesin (ERM) family of proteins (Trofatter et al., Cell. 75: 826).

Over-expression of Merlin can block both cell proliferation and oncogene-induced transformation (Lutchman and Rouleau, 1995, Cancer Res. 55(11): 2270-2274; Tikoo et al., 1994, J. Biol. Chem. 269(38): 23387-23390). Indeed, Merlin can negatively regulate cyclin D1 levels (Xiao et al., 2002, J. Biol. Chem. 277: 883-886) and loss of Merlin results in overexpression of cyclin D1 (Lallemand et al., 2003, Genes Dev. 17: 1090-1100). However, given its predominant localization to the membrane and cytoskeleton interface. Merlin is not likely to directly control the cell cycle machinery.

Several lines of evidence suggest that Merlin can regulate receptor tyrosine kinase activity, trafficking, and degradation. Merlin has been shown to interact directly with the focal adhesion component paxillin in a complex that contains integrin-β1 and Erb82 (Fernandez-Valle et al., 2002, Nat. Genet. 31(4): 354-362), HGF receptor substrate (HRS) (Scoles et al., 2002, Hum. Mol. Genet. 11(25): 3179-3189; Gutmann et al., 2001, Hum. Mol. Genet. 10(8): 825-834; Soles et al., 2000, Hum. Mol. Genet. 9(11): 1567-1574), and platelet derived growth factor receptor (PDGFR) indirectly through interaction with a PDZ-containing adaptor protein EBP50/NHE-RF (Maudsley et al., 2000, Mol. Cell. Biol. 20(22): 8352-8363; Murthy et al., 1998, J. Biol. Chem. 273(3): 1273-1276). Neuregulin growth factors (EGF family of growth factors), VEGF, and HGF are important mitogens for Schwann cells (SCs) (Krasnoselsky et al., 1994, J. Neurosci. 14:7284-7290; DeClue et al., 2000, J. Clin. Invest. 105(9):1233-1241; Caye-Thomasen et al., 2005, *Otol. Neurotol.* 26(1):98-101). Neuregulin/ErbB pathways are constitutively activated in human NF2 vestibular schwannomas and inhibitors of these pathways (e.g. antibody against neuregulin and Iressa) block proliferation of NF2-deficient schwannoma cells (Stonecypher et al., 2006, J. Neuropath. Exp. Neurol. 65:162-175; Hansen et al., 2006, Glia 53:593-600). Recent evidence from *Drosophila* indicates that Merlin can regulate abundance/turnover of many signaling and adhesion receptors such as Notch, the EGF receptor, Patched, Smoothened, E-cadherin, and Fat. Loss of merlin results in accumulation of these cell surface receptors and activation of the associated signaling pathways (e.g., the EGFR pathway and the Wingless pathway) (Maitra et al., 2000, *Curr. Biol.* 16(7):702-709).

In addition to cell surface receptors. Merlin has been shown to interact with downstream components of various signaling pathways, including Rac-PAK (p21-activated kinase) pathway. Rac is a member of the Rho family of small GTPases, which organize the actin cytoskeleton and control many cellular processes such as cell prohibition transformation, and cell motility (Etienne-Manneville and Hall, 2002, Nature. 420(6916):629-635; Sahai and Marshall, 2002, Nat. Rev. Cancer 2(2): 133-142). PAK can phosphorylate 5518 of Merlin (Xiao et al., 2002, J. Biol. Chem 277: 883-886; Kissel et al., 2002, J. Biol. Chem. 277(12): 10394-10399) which leads to conformational change and loss of growth-suppressing activity (Shaw et al., 1998, J. Biol. Chem. 273(13): 7757-7764; Shaw et al., 2001, Dev. Cell. 1(1): 63-72). Merlin can also act as a negative regulator of Rac-PAK signaling (Shaw et al., 2001, Dev. Cell. 1:63-72; Kassil et al., 2003, Mol. Cell. 12:841-849; Lallemand et al., 2003, Genes Dev. 17: 1090-1100; Hirokawa et al., 2004, Cancer J. 10: 20-26). Loss of Merlin results in the inappropriate phosphorylation and activation of PAK. Over-expression of Merlin inhibits PAK activation and blocks Rac-induced transformation. (Shaw et al., 2001, Dev. Cell 1(1): 63-72; Kissil et al., 2003, Mol. Cell. 12(4):841-849). Preliminary evidence indicates that loss of Merlin also leads to activation of the Ras/Raf/Mek/Erk pathway and PI3K-Akt pathway (Rangwala et al., 2005, *J. Biol. Chem.* 280(12): 11790-11797). A recent study from *Drosophilia* has proposed that Merlin and a related protein expanded function upstream of the Hippo signaling pathway to regulate cell proliferation and apoptosis (Hamaratoglu et al., 2006, Nat. cell biol. 8:27-36; Willecke et al., 2006, Curr Biol. 16(21): 2090-2100). The link between Merlin and growth factor receptor signaling indicates that growth factor receptors may play direct roles in NF2-associated tumor formation and progression. However, possible involvement of Merlin with multiple signaling pathways presents a challenge in developing drugs for the treatment of NF2.

Neurofibromatosis Type I

NF1 affects the human nervous system (Sorensen S A Mulvihill J J, Nielsen A, Ann N Y Acad Sci 1986; 486:30-7.). In certain embodiments, NF1 is an autosomal dominantly inherited genetic disorder with frequent germline deletion or loss-of-function mutations of the NF1 gene, and is caused by mutation in the NF1 gene, which encodes Neurofibromin, a tumor suppressor. Neurofibromin shares a region of similarity with the p120RasGAP protein, therefore functioning as a negative regulator of the Ras pathway.

In certain embodiments, the signs of NF1 include café-au-lait macules, skin freckling, skeletal defects, learning disability, Lisch nodules, dermal and plexiform neurofibromas (most common), benign tumors of the brain or other organs (e.g. optic pathway astrocytomas, optic neuromas, optic gliomas, cerebral astrocytomas, cerebral gliomas, ganglioneuromas, ependymomas, pheochromocytomas and ganglioneuromas), and malignant neoplasms (e.g. rhabdomyosarcomas, neurofibrosarcomas or malignant peripheral nerve sheath tumors (MPNST) or malignant schwannomas) (Korf B R. J Child Neurol 2002; 17(8):573-7; discussion 602-4, 46-51.) Children affected by NF1 also have increased risk for developing a rare form of leukemia-juvenile myelomonocytic leukemia (JMML) (Stiller C A, Chessells J M, Fitchett M. Br J Cancer 1994; 70(5):969-72.). Dermal neurofibromas, subdermal neurofibromas, plexiform neurofibromas and MPNSTs are primarily derived from Schwann cells or their progenitors. Optic gliomas and astrocytomas are derived from astrocytes, Pheochromocytomas are derived from neural crest components (as are neurofibromas and MPNSTs).

In certain embodiments, the typical characteristic of NF1 is the neurofibroma, of which there are clinically and histologically distinct types. These tumors may cause disfigurement, chronic pain and pruritus. Certain patients may develop some of the same disfiguring symptoms that are associated with Elephant Man's disease, a separate disorder originally thought to be NF1. Plexiform neurofibromas may be congenital and are present in a subpopulation of patients with NF1. They affect long portions of nerves and infiltrate the nerve and surrounding tissue, resulting in disfiguration and neuralgic complications. In certain embodiments, plexiform neurofibromas transform to malignant peripheral nerve-sheath tumors, which have a significant mortality rate.

The Nf1 gene was identified in 1990 (Wallace et al. 1990 *Science* 249:181-186; Cawthon et al. 1990 *Cell* 62:193-201) and its gene product, neurofibromin, has a catalytic domain related to the GTPase-activating protein (GAP) domain of p120RasGAP (Marchuk et al., 1991 *Genomics* 11:931-940; Gutmann et al., 1991. *Proc. Natl. Acad. Sci. U.S.A.* 88: 9658-9662; DeClue et al., 1991. *Proc. Natl. Acad. Sci. U.S.A.* 88:9914-9918; Martin et al., 1990, *Cell* 63:843-849; Xu et al., 1990. *Cell* 63: 835-841; Xu et al., 1990. *Cell* 62: 599-608). Loss of Nf1 in human neurofibromas, MPNSTs, leukemias, and tumor-derived cell lines results in the elevation of Ras-GTP levels and activation of Ras-Raf-Mek-Erk2 and other MAP kinase pathways (Guha et al., 1996 *Oncogene* 12: 507-513; Bollag et al., 1996. *Nat. Genet.* 12:144-148; Basu et al. 1992. *Nature* 356: 713-715; DeClue et al., 1992 *Cell* 69:265-273). For example, Ras-GTP levels from a few NF1 MPNST-derived cell lines ST88-14, 88-3 and 90-8 are much higher compared to other cell lines with normal neurofibromin. These cell lines also have activated downstream MAP kinase pathways. In addition, cell proliferation and soft agar growth of ST88-14 can be inhibited by injection of an antibody against Ras and expression of the GAP domain of neurofibromin, respectively.

The present invention also provides for a derivative of monoterpene or sesquiterpene, such as a perillyl alcohol derivative. The present invention also provides for a pharmaceutical composition comprising a derivative of monoterpene or sesquiterpene, such as a perillyl alcohol derivative. For example, the perillyl alcohol derivative may be a perillyl alcohol carbamate. The perillyl alcohol derivative may be perillyl alcohol conjugated with a therapeutic agent such as a chemotherapeutic agent. The monoterpene (or sesquiterpene) derivative may be formulated into a pharmaceutical composition, where the monoterpene (or sesquiterpene) derivative is present in amounts ranging from about 0.01% (w/w) to about 100% (w/w), from about 0.1% (w/w) to about 80% (w/w), front about 1% (w/w) to about 70% (w/w), from about 10% (w/w) to about 60% (w/w), or from about 0.1% (w/w) to about 20% (w/w). The present compositions can be administered alone, or may be co-administered together with radiation or another agent (e.g., a chemotherapeutic agent), to treat a disease such as cancer. Treatments may be sequential, with the monoterpene (or sesquiterpene) derivative being administered before or after the administration of other agents. For example, a perillyl alcohol carbamate may be used to sensitize a cancer patient to radiation or chemotherapy. Alternatively, agents may be administered concurrently. The route of administration may vary, and can include inhalation, intranasal, oral, transdermal, Intravenous, subcutaneous or intramuscular injection. The present invention also provides for a method of treating a disease such as cancer, comprising the step of delivering to a patient a therapeutically effective amount of a derivative of monoterpene (or sesquiterpene).

The present invention provides for methods of treating a disease such as cancer using an isoperillyl alcohol or a derivative of an isoperillyl alcohol. Routes of administration include inhalation, intranasal oral, transdermal intravenous, subcutaneous and intramuscular injection.

In the present methods, a patient is administered a therapeutically effective amount of an isomer or analog of monoterpene or sesquiterpene, such as an isoperillyl alcohol. The present invention also provides for a method of treating a disease comprising the step of administering to a patient a therapeutically effective amount of a derivative of an isomer or analog of monoterpene or sesquiterpene, such as an isoperillyl alcohol carbamate. The derivative may be an isoperillyl alcohol conjugated with a therapeutic agent such as a chemotherapeutic agent.

For example, the isomer or analog of monoterpene or sesquiterpene can be an isoperillyl alcohol (iso-POH). Isoperillyl alcohols include any isomers or analogs of perillyl alcohol. In one embodiment, the isoperillyl alcohol is (4-isopropylidene cyclohex-1-enyl)methanol. Other examples of isoperillyl alcohol include, but are not limited to, (4-isopropyl cyclohexa-1,3-dienyl)methanol, (4-isopropyl cyclohexa-1,4-dienyl)methanol, 4-isopropylphenyl)methanol and (4-isopropenylphenyl)methanol.

An exemplary isoperillyl alcohol, (4-isopropylidene cyclohex-1-enyl)methanol, is shown below:

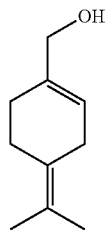

The compounds of the present invention may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. The present invention also provides methods of treating CNS (central nervous system) disorders, including, without limitation, primary degenerative neurological disorders such as Alzheimer's, Parkinson's, psychological disorders, psychosis and depression.

Also encompassed by the present invention is a derivative of an isomer or analog of monoterpene or sesquiterpene such as an isoperillyl alcohol derivative. For example, the isoperillyl alcohol derivative may be an isoperillyl alcohol carbamate, ester, or ether. The derivative of an isomer or analog of monoterpene or sesquiterpene may be an isomer or analog of monoterpene or sesquiterpene conjugated with a therapeutic agent such as a chemotherapeutic agent. The isoperillyl alcohol derivative may be isoperillyl alcohol conjugated with a therapeutic agent such as a chemotherapeutic agent.

The compounds of the present invention thus include both isomers or analogs of monoterpene or sesquiterpene, and derivatives of an isomer or analog of monoterpene or sesquiterpene. The isomer or analog of monoterpene or sesquiterpene (or the derivative of an isomer or analog of monoterpene or sesquiterpene), may be formulated into a pharmaceutical composition, where the isomer or analog of monoterpene or sesquiterpene (or the derivative of an isomer or analog of monoterpene or sesquiterpene), is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w). The present compositions can be administered alone, or may be co-administered together with radiation or another agent (e.g., a chemotherapeutic agent), to treat a disease such as cancer. Treatments may be sequential, with isomer or analog of monoterpene or sesquiterpene (or the derivative of an isomer or analog of monoterpene or sesquiterpene) being administered before or after the administration of other agents. For example, an isoperillyl alcohol (or an isoperillyl alcohol carbamate, ester, or ether) may be used to sensitize a cancer patient to radiation or chemotherapy. Alternatively, agents may be administered concurrently. The route of administration may vary, and can include, inhalation, intranasal, oral, transdermal, intravenous, subcutaneous or intramuscular injection.

The compositions of the present invention may contain one or more types of isomers or analogs of monoterpene or sesquiterpene (or the derivatives of isomers or analogs of monoterpene or sesquiterpene).

The compositions of the present invention may contain one or more types of derivatives of monoterpene (or sesquiterpene).

Monoterpenes include terpenes that consist of two isoprene units. Monoterpenes may be linear (acyclic) or contain rings. Derivatives of monoterpenoids are also encompassed by the present invention. Monoterpenoids may be produced by biochemical modifications such as oxidation or rearrangement of monoterpenes. Examples of monoterpenes and monoterpenoids include, perillyl alcohol (S)–)) and (R(+)), ocimene, myrcene, geraniol, citral, citronelloi, citronellal, linalool, pinene, terpineol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvacrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol geranial, citral a, neral, citral b, citronellal, etc.), monocyclic monoterpenes (e.g., limonene, terpinene phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g., tricyclene). See *Encyclopedia of Chemical Technology*, Fourth Edition, Volume 23, page 834-835.

Sesquiterpenes of the present invention include terpenes that consist of three isoprene units. Sesquiterpenes may be linear (acyclic) or contain rings. Derivatives of sesquiterpenoids are also encompassed by the present invention. Sesquiterpenoids may be produced by biochemical modifications such as oxidation or rearrangement of sesquiterpenes. Examples of sesquiterpenes include farnesol, farnesal, farnesylic acid and nerolidol.

The derivatives of monoterpene (or sesquiterpene) include, but are not limited to, carbamates, esters, ethers, alcohols and aldehydes of the monoterpene for sesquiterpene). Monoterpene (or sesquiterpene) alcohols may be derivatized to carbamates, esters, ethers, aldehydes or acids.

The derivatives of isomers or analogs of monoterpene or sesquiterpene include, but are not limited to, carbamates, esters, ethers, alcohols and aldehydes of the monoterpene (or sesquiterpene). Alcohols may be derivatized to carbamates, esters, ethers, aldehydes or acids.

Carbamate refers to a class of chemical compounds sharing the functional group

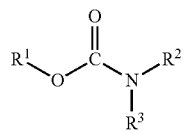

based on a carbonyl group flanked by an oxygen and a nitrogen. $R^1$, $R^2$ and $R^3$ can be a group such as alkyl, aryl, etc., which can be substituted. The R groups on the nitrogen and the oxygen may form a ring. $R^1$—OH may be a monoterpene, e.g., POH, or iso-POH. The $R^2$—N—$R^3$ moiety may be a therapeutic agent.

Carbamates may be synthesized by reacting isocyanate and alcohol or by reacting chloroformate with amine. Carbamates may be synthesized by reactions making use of phosgene or phosgene equivalents. For example, carbamates may be synthesized by reacting phosgene gas, diphosgene or a solid phosgene precursor such as triphosgene with two amines or an amine and an alcohol. Carbamates (also known as urethanes) can also be made from reaction of a urea intermediate with an alcohol. Dimethyl carbonate and diphenyl carbonate are also used for making carbamates. Alternatively, carbamates may be synthesized through the reaction of alcohol and or amine precursors with an ester-substituted diaryl carbonate, such as bismethylsalicylcarbonate (BMSC). U.S. Patent Publication No. 20100113819.

Carbamates may be synthesized by the following approach:

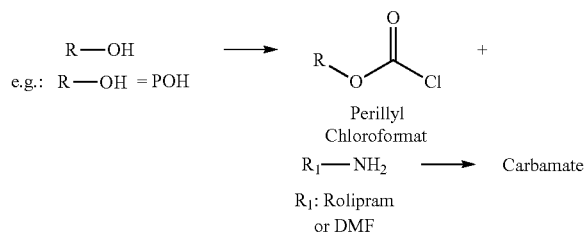

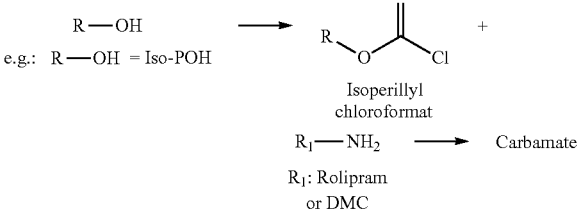

Suitable reaction solvents include, but are not limited to, tetrahydrofuran, dichloromethane, dichloroethane, acetone, and diisopropyl ether. The reaction may be performed at a temperature ranging from about −70° C. to about 80° C., or from about −65° C. to about 50° C. The molar ratio of perillyl chloroformate (or isoperillyl chloroformate) to the substrate R—$NH_2$ may range from about 1:1 to about 2:1, from about 1:1 to about 1.5:1, from about 2:1 to about 1:1, or from about 1.05:1 to about 1.1:1. Suitable bases include, but are not limited to, organic bases, such as triethylamine, potassium carbonate, N,N'-diisopropylethylamine, butyl lithium, and potassium-t-butoxide.

Alternatively, carbamates may be synthesized by the following approach:

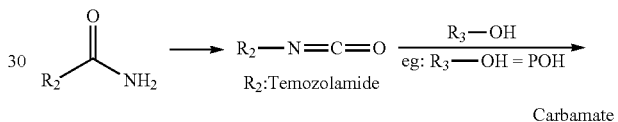

R3-OH may be, e.g., POH or iso-POH.

Suitable reaction solvents include, but are not limited to, dichloromethane, dichloroethane, toluene, diisopropyl ether, and tetrahydrofuran. The reaction may be performed at a temperature ranging from about 25° C. to about 110° C., or from about 30° C. to about 80° C., or about 50° C. The molar ratio of perillyl alcohol (or isoperillyl alcohol) to the substrate R—N═C═O may range from about 1:1 to about 2:1, from about 1:1 to about 1.5:1, from about 2:1 to about 1:1, or from about 1.05:1 to about 1.1:1.

Esters of the monoterpene (or sesquiterpene) alcohols (or esters of the alcohols of the isomers or analogs of monoterpene or sesquiterpene) can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid, and any therapeutic agent bearing at least one carboxylic acid functional group. Examples of esters of the alcohols include, but are not limited to, carboxylic acid esters (such as benzoate esters, fatty acid esters (e.g., palmitate ester, linoleate ester, stearate ester, butyryl ester and oleate ester), acetates, propionates (or propanoates), and formates), phosphates, sulfates, and carbamates (e.g., N,N-dimethylaminocarbonyl).

A specific example of a monoterpene that may be used in the present invention is perillyl alcohol. The derivatives of perillyl alcohol include, perillyl alcohol carbamates, perillyl alcohol esters, perillic aldehydes, dihydroperillic acid, perillic acid, perillic aldehyde derivatives, dihydroperillic acid esters and perillic acid esters. The derivatives of perillyl alcohol may also include its oxidative and nucleophilic/electrophilic addition derivatives. U.S. Patent Publication No. 20090031455. U.S. Pat. Nos. 6,131,324 and 3,957,856. Many examples of derivatives of perillyl alcohol are reported in the chemistry literature (see Appendix A: CAS Scifinder search output file, retrieved Jan. 25, 2010).

The derivatives of isoperillyl alcohol include isoperillyl alcohol carbamates, isoperillyl alcohol esters, isoperillic aldehydes, isoperillic acid, isoperillic aldehyde derivatives, and isoperillic acid esters. The derivatives of isoperillyl alcohol may also include its oxidative and nucleophilic/electrophilic addition derivatives. Few examples of derivatives of isoperillyl alcohol are reported in the chemistry literature. See U.S. Pat. No. 5,994,598 and Japanese Patent No. 07048264A.

In certain embodiments, a POH carbamate (or an iso-POH carbamate) is synthesized by a process comprising the step of reacting a first reactant of perillyl chloroformate (or isoperillyl chloroformate) with a second reactant such as dimethyl celocoxib (DMC), temozolomide (TMZ) and rolipram. The reaction may be carried out in the presence of tetrahydrofuran and a base such as n-butyl lithium. Perillyl chloroformate (or isoperillyl chloroformate) may be made by reacting POH (or iso-POH) with phosgene. For example, POH (or iso-POH) conjugated with temozolomide through a carbamate bond may be synthesized by reacting temozolomide with oxalyl chloride followed by reaction with perillyl alcohol (or iso-POH). The reaction may be carried out in the presence of 1,2-dichloroethane.

POH carbamates encompassed by the present disclosure include, but not limited to, 4-bis-N,N'-4-isopropenyl cyclohex-1-enylmethyloxy carbonyl [5-(2,5-dimethyl phenyl)-3-trifluoromethyl pyrazol-1-yl] benzenesulfonamide, 4-(3-cyclopentyloxy-4-methoxy phenyl)-2-oxo-pyrrolidine-1-carboxylic acid 4-isopropenyl cyclohex-1-enylmethyl ester, and (3-methyl 4-oxo-3,4-dihydroimidazo[5,1-d][1,2,3,5]tetrazine-8-carbonyl)carbamic acid-4-isopropenyl cyclohex-1-enylmethyl ester. The details of the chemical reactions generating these compounds are described in the Examples below.

Iso-POH carbamates encompassed by the present invention include, but are not limited to, (3-Methyl 4-oxo-3,4-dihydroimidazo[5,1-d][1,2,3,5]tetrazine-8-carbonyl)-carbamic acid-4-isopropylidene cyclohex-1-enylmethyl ester, 4-(3-Cyclopentyloxy-4-methoxyphenyl)-2-oxo-pyrrolidine-1-carboxylic acid 4-isopropylidene cyclohex-1-enylmethyl ester, 4-(Bis-N,N'-4-isopropylidene cyclohex-1-enylmethyloxy carbonyl [5-(2,5-dimethyl phenyl)-3-trifluoromethyl pyrazol-1-yl] benzenesulfonamide. The details of the chemical reactions generating these compounds are described in the Examples below.

In certain embodiments, perillyl alcohol derivatives may be perillyl alcohol fatty acid esters, such as palmitoyl ester of POH and linoleoyl ester of POH, the chemical structures of which are shown below.

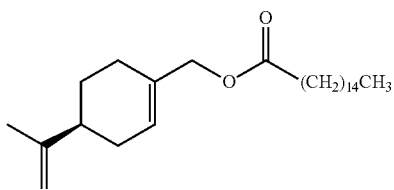

Hexadecanoic acid 4-isopropenyl-cyclohex-1-enylmethyl ester (Palmitoyl ester of POH)

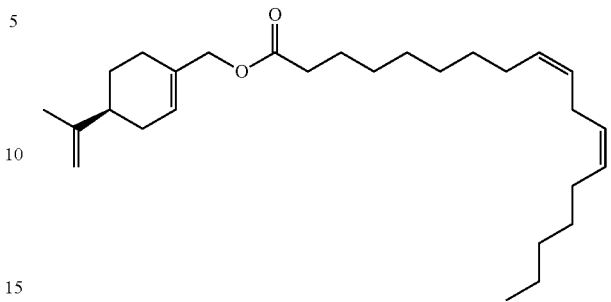

Octadeca-9,12-dienoic acid 4-isopropenyl-cyclohex-1-enylmethyl ester (Linoleoyl ester of POH)

In certain embodiments, iso-perillyl alcohol derivatives may be isoperillyl alcohol fatty acid esters, such as palmitoyl ester of iso-POH and linoleoyl ester of iso-POH.

The monoterpene (or sesquiterpene) derivative may be a monoterpene (or sesquiterpene) conjugated with a therapeutic agent. A monoterpene (or sesquiterpene) conjugate encompassed by the present invention is a molecule having a monoterpene (or sesquiterpene) covalently bound via a chemical linking group to a therapeutic agent. The molar ratio of the monoterpene (or sesquiterpene) to the therapeutic agent in the monoterpene (or sesquiterpene) conjugate may be 1:1, 1:2, 1:3, 1:4, 2:1, 3:1, 4:1, or any other suitable molar ratios. The monoterpene (or sesquiterpene) and the therapeutic agent may be covalently linked through carbamate, ester, ether bonds, or any other suitable chemical functional groups. When the monoterpene (or sesquiterpene) and the therapeutic agent are conjugated through a carbamate bond, the therapeutic agent may be any agent bearing at least one carboxylic acid functional group, or any agent bearing at least one amine functional group. In a specific example, a perillyl alcohol conjugate is perillyl alcohol covalently bound via a chemical linking group to a chemotherapeutic agent.

The derivative of an isomer or analog of monoterpene or sesquiterpene may be an isomer or analog of monoterpene or sesquiterpene conjugated with a therapeutic agent. A conjugate encompassed by the present invention is a molecule having an isomer or analog of monoterpene or sesquiterpene covalently bound via a chemical linking group to a therapeutic agent. The molar ratio of the isomer or analog of monoterpene or sesquiterpene to the therapeutic agent in the conjugate may be 1:1, 1:2, 1:3, 1:4, 2:1, 3:1, 4:1, or any other suitable molar ratios. The isomer or analog of monoterpene or sesquiterpene and the therapeutic agent may be covalently linked through carbamate, ester, ether bonds, or any other suitable chemical functional groups. When the isomer or analog of monoterpene or sesquiterpene and the therapeutic agent are conjugated through a carbamate bond, the therapeutic agent may be any agent bearing at least one carboxylic acid functional group, or any agent bearing at least one amine functional group. In a specific example, an isoperillyl alcohol conjugate is isoperillyl alcohol covalently bound via a chemical linking group to a chemotherapeutic agent.

According to the present invention, the therapeutic agents that may be conjugated with monoterpene or sesquiterpene (or an isomer or analog of monoterpene or sesquiterpene) include, but are not limited to, chemotherapeutic agents, therapeutic agents for treatment of CNS disorders (including, without limitation, primary degenerative neurological disorders such as Alzheimer's, Parkinson's, multiple sclerosis, Attention-Deficit Hyperactivity Disorder or ADHD, psychological disorders, psychosis and depression), immunotherapeutic agents, angiogenesis inhibitors, and anti-hypertensive agents. Anti-cancer agents that may be conjugated with monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention is co-administration, admixtures, and coformulations of POH, or iso-POH, and at least one other therapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide (TMZ); Altretamine and Mitobronitol.

Non-limiting examples of Topoisomerase I inhibitors include Campothecin derivatives including SN-38, APC, NPC, campothecin, topotecan, exatecan mesylate, 9-nitro-camptothecin, 9-aminocamptothecin, lurtotecan, rubitecan, silatecan, gimatecan, diflomotecan, extatecan, BN-80927, DX-8951f, and MAG-CPT as described in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-125, Crow et al. (1994) *J. Med. Chem.* 37(19):31913194, and Crespi et al. (1986) *Biochem. Biophys. Res. Commun.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo [e]pyrimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Amthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cispiatin, Nedaplatin, Oxaliplatin, Triplatin tetranitrate, Satraplatin, Aroplatin, Lobaplatin, and JM-216. (see McKeage et al. (1997) *J. Clin. Oncol.* 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. This therapy includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from 23 the National Comprehensive Cancer Network's web site, nccn.org, last accessed on May 27, 2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecetabine (Xeloda), S-1 (MBMS-247016, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The (Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); ber-abl (Imatinib, Nilotinib, Dasatinib); Src (Bosutinib) and Janus kinase 2 (Lestaurtinib).

"Lapatinib" (Tykerb®) is an dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to, Zactima (ZD6474), Iressa (gefitinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SUI 1248) and lefltmonomide (SU101).

PTK/ZK is a tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR-Flk-1) and VEGFR-3 (Flt-4). The chemical names of PTK/ZK are 1-[4-Chloroanilino]-4-[4-pyridylmethyl] phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTX787/ZK 222584, CGP-79787, DE-00268, PTK-787, PTK787A, VEGFR-TK inhibitor, ZK 222584 and ZK.

Chemotherapeutic agents that can be used in admixtures and/or coformulations and/or conjugated with monoterpene or sesquiterpene (or an isomer or analog of monoterpene or sesquiterpene) may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

The monoterpene or sesquiterpene (or an isomer or analog of monoterpene or sesquiterpene) may be conjugated and/or used in admixtures and/or coformulations with angiogenesis inhibitors. Examples of angiogenesis inhibitors include, but are not limited to, angiostatin, angiozyme, antithrombin III, AG3340, VEGF inhibitors, batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloracetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IMS862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2,2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin. VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angtogenesis and may also be conjugated and/or used in admixtures and/or coformulations with monoterpene or sesquiterpene (or an isomer or analog of monoterpene or sesquiterpene) include agents that modulate or inhibit the coagulation and fibrinolysis systems, including, but not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Non-limiting examples of the anti-hypertensive agents include angiotensin converting enzyme inhibitors (e.g., captopril, enalapril, delapril etc.), angiotensin II antagonists (e.g., candesartan cilexetil, candesartan, losartan (or Cozaar), losartan potassium, eprosartan, valsartan (or Diovan), termisartan, irbesartan, tasosartan, olmesartan, olmesartan medoxomil etc.), calcium antagonists (e.g., manidipine, nifedipine, amlodipine (or Amlodin), efonidipine, nicardipine etc.), diuretics, renin inhibitor (e.g., aliskiren etc.), aldosterone antagonists (e.g., spironolactone, eplerenone etc.), beta-blockers (e.g., metoprolol (or Toporol), atenolol, propranolol, carvedilol, pindolol etc.), vasodilators (e.g., nitrate, soluble guanylate cyclase stimulator or activator, prostacyclin etc.), angiotensin vaccine, clonidine and the like. U.S. Patent Publication No. 20100113780.

Other therapeutic agents that may be conjugated (or an isomer or analog of monoterpene or sesquiterpene) with monoterpene (or sesquiterpene) include, but are not limited to, Sertraline (Zoloft), Topiramate (Topamax), Duloxetine (Cymbalta), Sumatriptan (Imitrex), Pregabalin (Lyrica), Lamotrigine (Lamictal), Valaciclovir (Valtrex), Tamsulosin (Flomax), Zidovudine (Combivir), Lamivudine (Combivir), Efavirenz (Sustiva), Abacavir (Epzicom), Lopinavir (Kaletra), Pioglitazone (Actos), Desloratidine (Clarinex), Cetiriz ine (Zyrtec), Pentoprazole (Protonix), Lansoprazole (Prevacid), Rebeprazole (Aciphex), Moxifloxacin (Avelox), Meloxicam (Mobic), Dorzolamide (Truspot), Diclofenac (Voltaren), Enlapril (Vasotec), Montelukast (Singulair), Sildenafil (Viagra), Carvedilol (Coreg), Ramipril (Delix).

Table 1 lists pharmaceutical agents that can be conjugated with monoterpene or sesquiterpene (an isomer or analog of monoterpene or sesquiterpene), including structure of the pharmaceutical agent and the preferred derivative for conjugation.

TABLE 1

| Brand Name | Generic Name | Activity | Structure | Preferred Derivative |
|---|---|---|---|---|
| Zoloft | Sertraline | Depression | 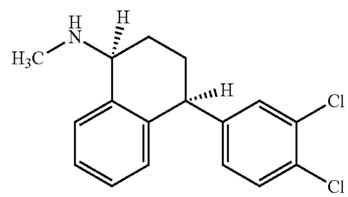 [SMILES: CN[C@H]1CC[C@@H](c2ccc(Cl)c(Cl)c2)c2ccccc21] | Carbamate |
| Topamax | Topiramate | Seizures | 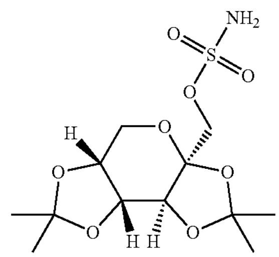 | Carbamate |
| Cymbalta | Duloxetine | Depression | 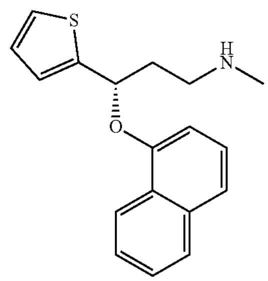 [SMILES: CNCC[C@H](Oc1cccc2ccccc12)c1cccs1] | Carbamate |
| Imitrex | Sumatriptan | Migraine | 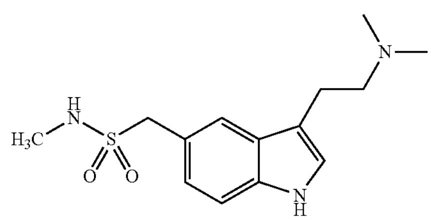 | Carbamate |
| Lyrica | Pregabalin | Neuropathic pain | 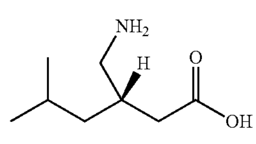 | Carbamate or Ester |
| Lamictal | Lamotrigine | Seizures | 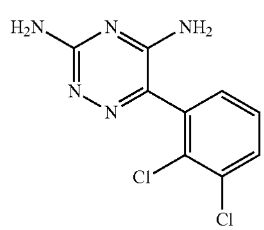 [SMILES: Nc1nnc(-c2cccc(Cl)c2Cl)c(N)n1] | Carbamate |

TABLE 1-continued

| Brand Name | Generic Name | Activity | Structure | Preferred Derivative |
|---|---|---|---|---|
| Valtrex | Valaciclovir | Herpes | 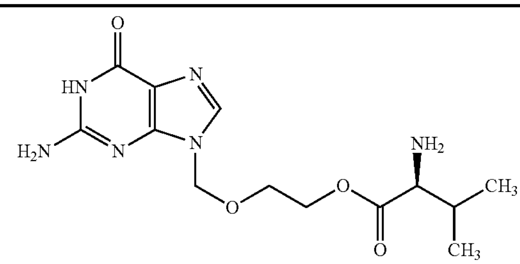 | Carbamate |
| Tarceva | Erlotinib | Non-small cell lung cancer | 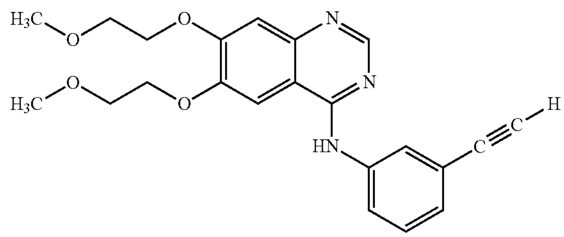 [SMILES: C#Cc1cccc(Nc2ncnc3cc(OCCOC)c(OCCOC)cc23)c1] | Carbamate |
| Flomax | Tamsulosin | Benign prostatic Cancer | 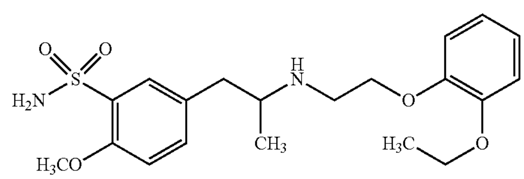 [SMILES: CCOc1ccccc1OCCNC(C)Cc1ccc(OC)c(S(N)(=O)=O)c1] | Carbamate |
| Gleevec | Imatinib | Leukemia | 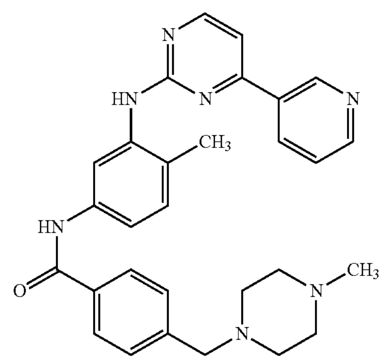 [SMILES: Cc1ccc(NC(=O)c2ccc(CN3CCN(C)CC3)cc2)cc1Nc1nccc(-c2cccnc2)n1] | Carbamate |
| Combivir | Zidovudine | HIV infection | | Carbamate |
| Combivir | Lamivudine | HIV infection | | Carbonate |

TABLE 1-continued

| Brand Name | Generic Name | Activity | Structure | Preferred Derivative |
|---|---|---|---|---|
| Sustiva | Efavirenz | HIV infection | 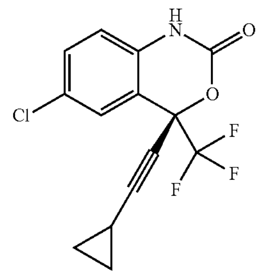 [SMILES: O=C1Nc2ccc(Cl)cc2[C@@](C#CC2CC2)(C(F)(F)F)O1] | Carbamate |
| Epzicom | Abacavir | HIV infection | 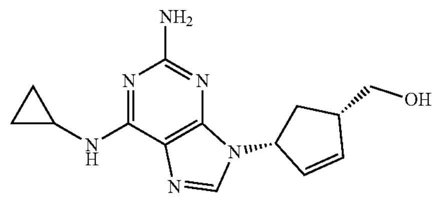 [SMILES: Nc1nc(NC2CC2)c2ncn([C@H]3C=C[C@@H](CO)C3)c2n1] | Carbamate |
| Kaletra | Lopinavir | HIV infection | 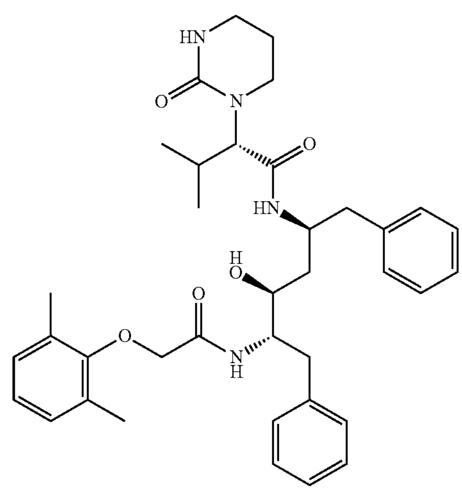 [SMILES: Cc1cccc(C)c1OCC(=O)N[C@@H](Cc1ccccc1)[C@@H](O)C[C@H](Cc1ccccc1)NC(=O)[C@H](C(C)C)N1CCCNC1=O] | Carbamate |
| Actos | Pioglitazone | Type-2 diabetes | 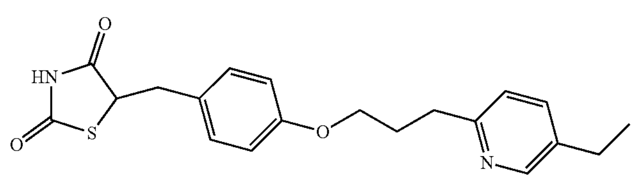 [SMILES: CCc1ccc(CCCOc2ccc(CC3SC(=O)NC3=O)cc2)nc1] | Carbamate |
| Clarinex | Desloratidine | Allergic rhinitis | 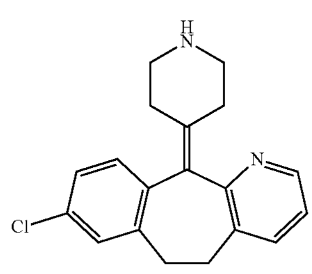 [SMILES: Clc1ccc2c(c1)CCc1cccnc1C2=C1CCNCC1] | Carbamate |

TABLE 1-continued

| Brand Name | Generic Name | Activity | Structure | Preferred Derivative |
|---|---|---|---|---|
| Zyrtec | Cetirizine | Allergic | 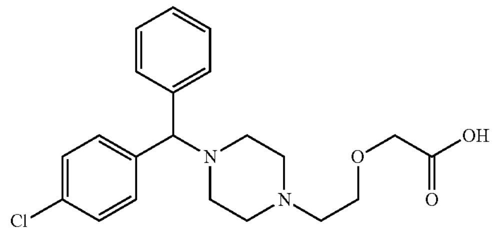 [SMILES: O=C(O)COCCN1CCN(C(c2ccccc2)c2ccc(Cl)cc2)CC1] | Ester |
| Protonix | Pentoprazole | Gastrointestinal | 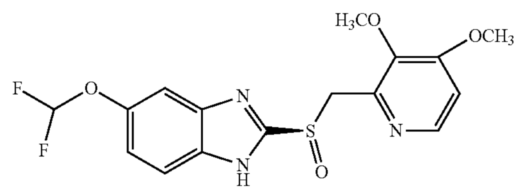 [SMILES: COc1ccnc(C[S@@](=O)c2nc3cc(OC(F)F)ccc3[nH]2)c1OC] | Carbamate |
| Prevacid | Lansoprazole | Gastrointestinal | 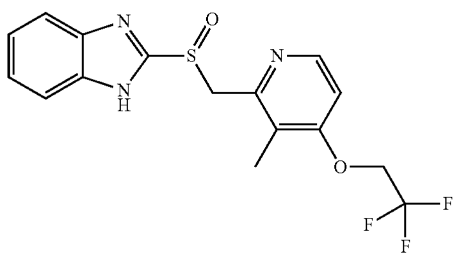 [SMILES: Cc1c(OCC(F)(F)F)ccnc1CS(=O)c1nc2ccccc2[nH]1] | Carbamate |
| Aciphex | Rebeprazole | Gastrointestinal | 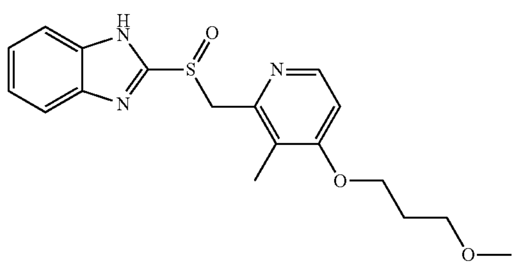 [SMILES: COCCCOc1ccnc(CS(=O)c2nc3ccccc3[nH]2)c1C] | Carbamate |
| Diovan | Valsartan | Hypertension | 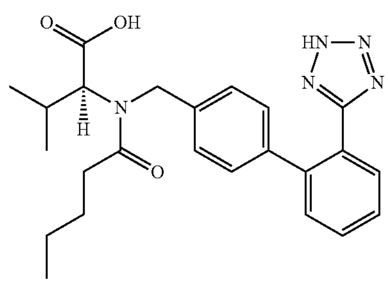 [SMILES: CCCCC(=O)N(Cc1ccc(-c2ccccc2-c2nn[nH]n2)cc1)[C@H](C(=O)O)C(C)C] | Carbamate |
| Cozaar | Losartan | Hypertension | 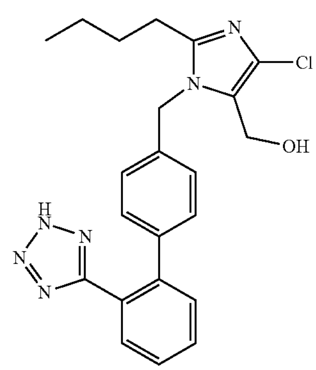 [SMILES: CCCCc1nc(Cl)c(CO)n1Cc1ccc(-c2ccccc2-c2nn[nH]n2)cc1] | Carbamate |

TABLE 1-continued

| Brand Name | Generic Name | Activity | Structure | Preferred Derivative |
|---|---|---|---|---|
| Avelox | Moxifloxacin | Bacterial infection | 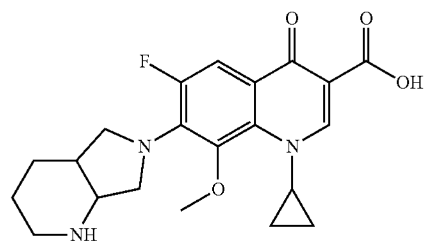 [SMILES: COc1c(N2CC3CCCNC3C2)c(F)cc2c(=O)c(C(=O)O)cn(C3CC3)c12] | Carbamate or Ester |
| Mobic | Meloxicam | Osteoarthritis | 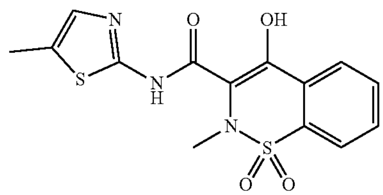 [SMILES: Cc1cnc(NC(=O)C2=C(O)c3ccccc3S(=O)(=O)N2C)s1] | Carbamate |
| Truspot | Dorzolamide | Intraocular pressure | 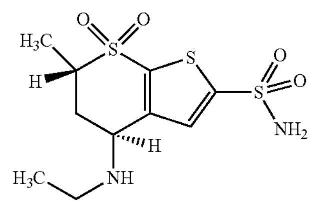 [SMILES: CCN[C@H]1C[C@H](C)S(=O)(=O)c2sc(S(N)(=O)=O)cc21] | Carbamate |
| Voltaren | Diclofenac | Osteoarthritis & rheumatoid arthritis | 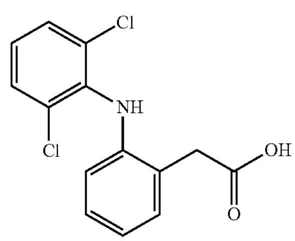 [SMILES: O=C(O)Cc1ccccc1Nc1c(Cl)cccc1Cl] | Carbamate or Ester |
| Vasotec | Enlapril | Hypertension | 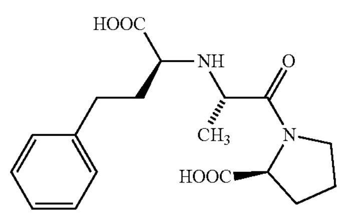 [SMILES: C[C@H](N[C@@H](CCc1ccccc1)C(=O)O)C(=O)N1CCC[C@H]1C(=O)O] | Carbamate or Ester |
| Singulair | Montelukast | Asthma | 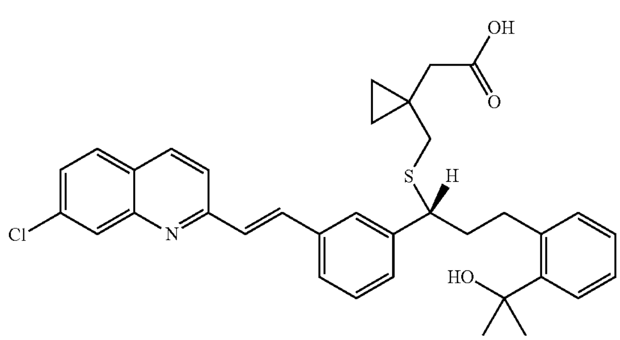 [SMILES: CC(C)(O)c1ccccc1CC[C@@H](SCC1(CC(=O)O)CC1)c1cccc(/C=C/c2ccc3ccc(Cl)cc3n2)c1] | Ester |

TABLE 1-continued

| Brand Name | Generic Name | Activity | Structure | Preferred Derivative |
|---|---|---|---|---|
| Amlodin | Amlodipine | Hypertension | 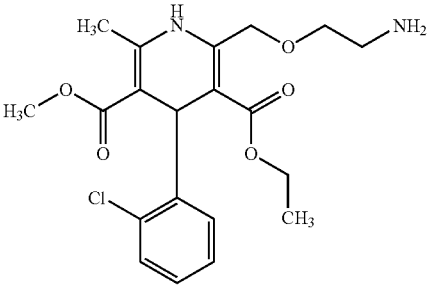 [SMILES: CCOC(=O)C1=C(COCCN)NC(C)=C(C(=O)OC)C1c1ccccc1Cl] | Carbamate |
| Toporol | Metoprolol | Hypertension | 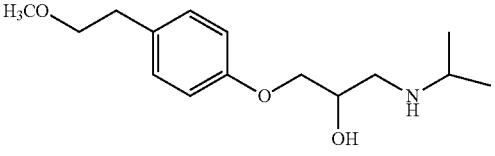 [SMILES: COCCc1ccc(OCC(O)CNC(C)C)cc1] | Carbamate |
| Viagra | Sildenafil | Erectile dysfunction | 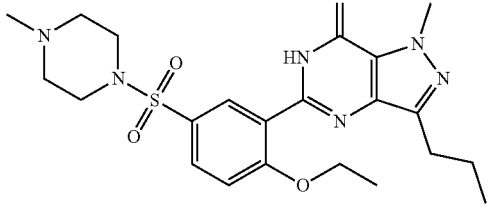 | Carbamate |
| Coreg | Carvedilol | Hypertension | 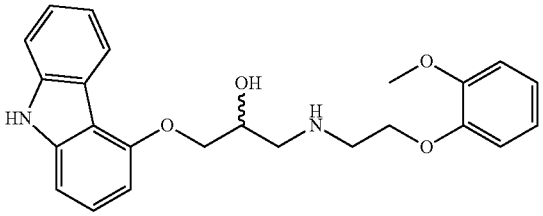 [SMILES: COc1ccccc1OCCNCC(O)COc1cccc2[nH]c3ccccc3c12] | Carbamate |
| Delix | Ramipril | Hypertension | 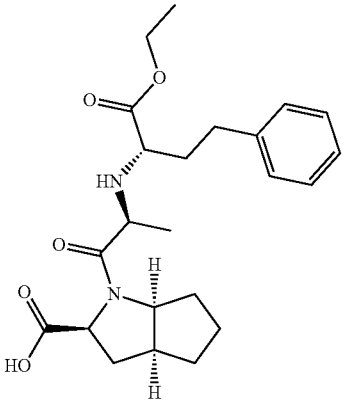 [SMILES: CCOC(=O)[C@H](CCc1ccccc1)N[C@@H](C)C(=O)N1[C@H](C(=O)O)C[C@@H]2CCC[C@@H]21] | Carbamate or Ester |
| Sinemet (Parcopa, Atamet) | L-DOPA | Neurological disorders | 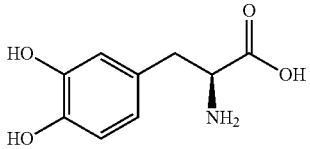 [SMILES: N[C@@H](Cc1ccc(O)c(O)c1)C(=O)O] | |

By way of example, an L-DOPA iso-POH conjugate is shown below:

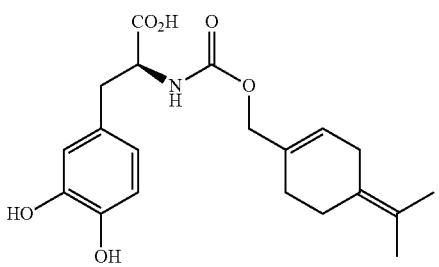 [SMILES: CC(C)=C1CC=C(COC(=O)N[C@@H](Cc2ccc(O)c(O)c2)C(=O)O)CC1]

The purity of the monoterpene or sesquiterpene or its derivatives (an isomer or analog of monoterpene or sesquiterpene, or its derivatives) may be assayed by gas chromatography (GC) or high pressure liquid chromatography (HPLC). Other techniques for assaying the purity of monoterpene (or sesquiterpene) derivatives and for determining the presence of impurities include, but are not limited to nuclear magnetic resonance (NMR) spectroscopy, mass spectrometry (MS), GC-MS, infrared spectroscopy (IR), and thin layer chromatography (TLC). Chiral purity can be assessed by chiral GC or measurement of optical rotation.

The monoterpene or sesquiterpene or its derivatives (an isomer or analog of monoterpene or sesquiterpene, or its derivatives) may be purified by methods such as crystallization, or by separating the monoterpene or sesquiterpene or its derivatives (an isomer or analog of monoterpene or sesquiterpene, or its derivatives) from impurities according to the unique physicochemical properties (e.g., solubility or polarity) of the derivative. Accordingly, the monoterpene or sesquiterpene or its derivatives (an isomer or analog of monoterpene or sesquiterpene, or its derivatives) can be separated by suitable separation techniques known in the art, such as preparative chromatography, (fractional) distillation, or (fractional) crystallization.

The invention also provides for methods of using monoterpene or sesquiterpene or its derivatives (an isomer or analog of monoterpene or sesquiterpene, or its derivatives) to treat a disease, such as cancer or other nervous system disorders. The present compound may be administered alone, or in combination with radiation, surgery or chemotherapeutic agents. The present compound may also be co-administered with antiviral agents, anti-inflammatory agents or antibiotics. The agents may be administered concurrently or sequentially. The present compound can be administered before, during or after the administration of the other active agent(s).

The present compound may be used in combination with radiation therapy. In one embodiment, the present disclosure provides for a method of treating tumor cells, such as malignant glioma cells, with radiation, where the cells are treated with an effective amount of the present compound, and then exposed to radiation. Treatment by the present compound may be before, during and/or after radiation. For example, the present compound may be administered continuously beginning one week prior to the initiation of radiotherapy and continued for two weeks after the completion of radiotherapy. U.S. Pat. Nos. 5,587,402 and 5,602,184.

In one embodiment, the present invention provides for a method of treating tumor cells, such as malignant glioma cells, with chemotherapy, where the cells are treated with an effective amount of the present compound, and then exposed to chemotherapy. Treatment by the present compound may be before, during and/or after chemotherapy.

The compounds and methods of the present invention may be used to inhibit the Ras protein. The Ras family is a protein family of small GTPases that are involved in cellular signal transduction. Activation of Ras signaling causes cell growth, differentiation and survival. Mutations in ras genes can permanently activate it and cause inappropriate transmission inside the cell even in the absence of extracellular signals. Because these signals result in cell growth and division, deregulated Ras signaling can ultimately lead to oncogenesis and cancer. Activating mutations in Ras are found in 20-25% of all human tumors and up to 90% in specific tumor types. Goodsell D S (1999). Downward J., "The molecular perspective: the ras oncogene". Oncologist 4 (3): 263-4. (January 2003). "Targeting RAS signalling pathways in cancer therapy". Nat. Rev. Cancer 3 (1): 11-22. Ras family members include, but are not limited to, HRAS; KRAS; NRAS; DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; and RRAS. Wennerberg K, Rossman K L, Der C J (March 2005). "The Ras superfamily at a glance". J. Cell. Sci. 118 (Pt 5): 843-6.

The present compound may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the the present compound include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkins's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present methods and compounds may be used to treat CNS disorders, including, without limitation, primary degenerative neurological disorders such as Alzheimer's, Parkinson's, psychological disorders, psychosis and depression. Treatment may consist of the use of the present compound alone or in combination with current medications used in the treatment of Parkinson's, Alzheimer's, or psychological disorders.

The present invention also provides a method of improving immunomodulatory therapy responses comprising the steps of exposing cells to an effective amount of the present compound, before or during immunomodulatory treatment. Preferred immunomodulatory agents are cytokines, such interleukins, lymphokines, monokines, interfereons and chemokines.

The present composition may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of compound of the present disclosure may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. In certain embodiments, the composition is administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of the monoterpene (or sesquiterpene) derivative to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

This invention also provides the compositions as described above for intranasal administration. As such, the compositions can further comprise a permeation enhancer. Southall et al. *Developments in Nasal Drug Delivery,* 2000. The monoterpene (or sesquiterpene) derivative may be administered intranasally in a liquid form such as a solution, an emulsion, a suspension, drops, or in a solid form such as a powder, gel or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Wash.) can be used in this invention (http://www.kurvtech.com). The compounds of the present invention may also be delivered through a tube, a catheter, a syringe, a packtail, a pledget, a nasal tampon or by submucosal infusion. U.S. Patent Publication Nos. 20000326275, 20090201894, 20090281522 and 20090317377.

The present compound can be formulated as aerosols using standard procedures. The compound may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The present compound may be delivered to the nasal cavity as a powder in a form such as microspheres delivered by a nasal insufflator. The present compound may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxy methyl or hydroxylpropyl).

The composition containing the present compound can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 µm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568, 480 and 6,123,068, and WO 97/12687. The monoterpenes (or sesquiterpenes) can be formulated for use in a nebulizer device as an aqueous solution or as a liquid suspension.

DPI devices typically administer a therapeutic agent in the form of a free-flowing powder that can be dispersed in a patient's air-stream during inspiration. DPI devices which use an external energy source may also be used in the present invention. In order to achieve a free-flowing powder, the therapeutic agent can be formulated with a suitable excipient (e.g., lactose). A dry powder formulation can be made, for example, by combining dry lactose having a particle size between about 1 µm and 100 µm with micronized particles of the monoterpenes (or sesquiterpenes) and dry blending. Alternatively, the monoterpene can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,534,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 09/53901, WO 00/61108, WO 99/55319 and WO 00/30614.

The present compound may be encapsulted in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The present compound may also be used alone or in combination with other chemotherapeutic agents via topical application for the treatment of localized cancers such as breast cancer or melanomas. The present compound may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197, 934; 6,056,950; 5,800,807; 5,776,445; 5,698,219; 5,521, 222; 5,403,841; 5,077,033; 4,882; 150; and 4,738,851.

The present compound can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The invention also provides a method for inhibiting the growth of a cell in vitro, ex vivo or in vivo, where a cell, such as a cancer cell, is contacted with an effective amount of the compound as described herein.

Pathological cells or tissue such as hyperproliferative cells or tissue may be treated by contacting the cells or tissue with an effective amount of a composition of this disclosure.

The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis from a systemic cancer, lung cancer, prostate cancer, breast cancer, hematopoietic cancer or ovarian cancer. The cells can be from a vertebrate, preferably a mammal, more preferably a human. U.S. Patent Publication No. 2004/0087651. Balassiano et al. (2002) *Intern J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of the present composition can be determined using methods well known in the art. For example, the cytoxicity of the present monoterpene (or sesquiterpene) and/or the therapeutic agents may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, winch can be read spectrometrically. *J. of immunological Methods* 65: 55 63, 1983. The cytoxicity of the present monoterpene (or sesquiterpene) derivative and/or the therapeutic agents may be studied by colony formation assay. Functional assays for inhibition of VEGF secretion and IL-8 secretion may be performed via ELISA. Cell cycle block by the present monoterpene (or sesquiterpene) derivative and/or the therapeutic agents may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

The following are examples of the present invention and are not to be construed as limiting.

EXAMPLES

Example 1

Synthesis of Dimethyl Celecoxib bisPOH Carbamate (4-bis-N,N'-4-isopropenyl cyclohex-1-enylmethyloxy carbonyl [5-(2,5-dimethyl phenyl)-3-trifluoromethyl pyrazol-1-yl]benzenesulfonamide)

The reaction scheme is the following:

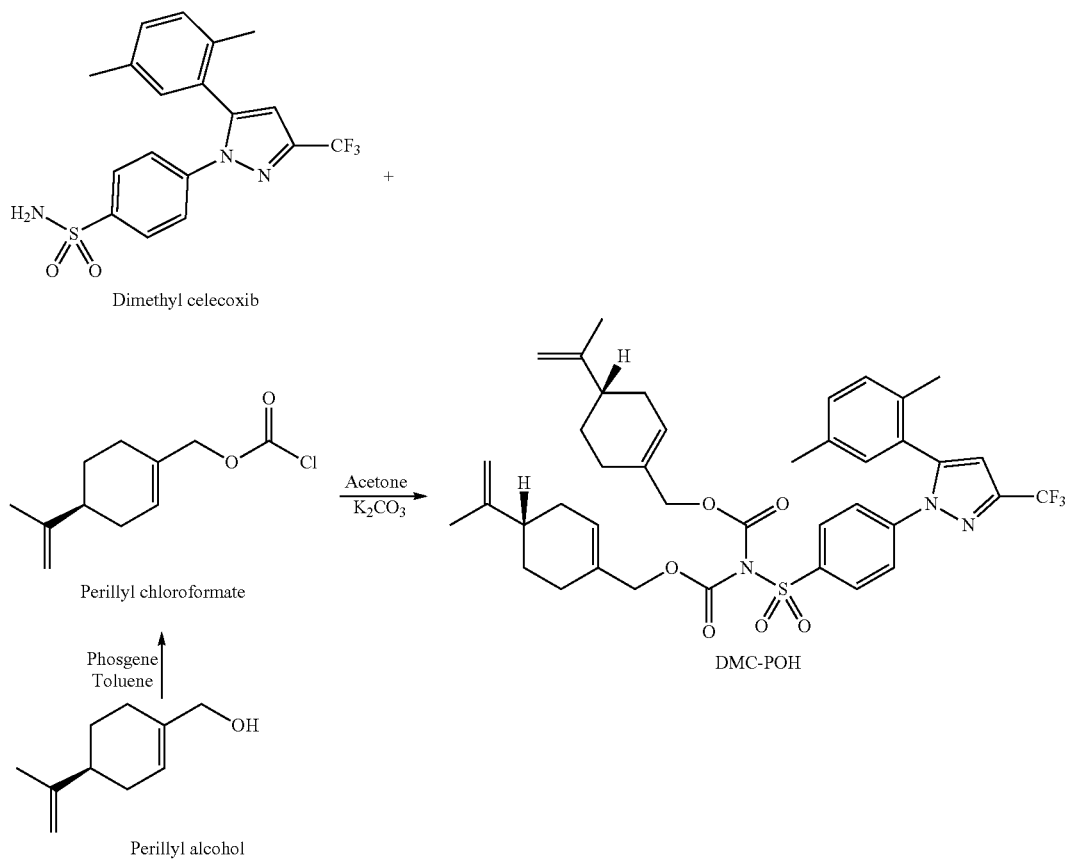

Phosgene (20% in toluene, 13 ml, 26.2 mmol) was added to a mixture of perrilyl alcohol (2.0 grams, 13.1 mmol) and potassium carbonate (5.4 grams, 39.1 mmol) in dry toluene (30 mL) over a period of 30 minutes while maintaining the temperature between 10° C. to 15° C. The reaction mixture was allowed to warm to room temperature and stirred for 8.0 hours under $N_2$. The reaction mixture was quenched with water (30 mL) and the organic layer was separated. The aqueous layer was extracted with toluene (20 mL) and the combined organic layer was washed with water (50 mL×2), brine (15%, 30 mL) and dried over sodium sulfate (20 grams). The filtered organic layer was concentrated under vacuum to give perillyl chloroformate as an oil. Weight: 2.5 grams; Yield: 89%. $^1$H-NMR (400 MHz, CDCl$_3$): δ 1.5 (m, 1H), 1.7 (s, 3H), 1.8 (m, 1H), 2.0 (m, 1H), 2.2 (m, 4H), 4.7 (dd, 4H); 5.87 (m, 1H).

Perillyl chloroformate (0.11 grams, 0.55 mmol) was added slowly to a mixture of dimethyl celecoxib (0.2 grams, 0.50 mmol) and potassium carbonate (0.13 grams, 1.0 mmol) in dry acetone (10 mL) over a period of 5 minutes nudes N$_2$. The reaction mixture was heated to reflux and maintained for 3 hours. Since TLC analysis indicated the presence of dimethyl celecoxib (>60%), another 1.0 equivalent of perillyl chloroformate was added and refluxed for an additional 5 hours. The reaction mixture was cooled and acetone was concentrated under vacuum to give a residue.

The resulting residue was suspended in water (15 mL) and extracted with ethyl acetate (3×15 mL). The combined organic layer was washed with water (20 mL) followed by brine (15%, 20 mL) and dried over sodium sulfate. The filtered organic layer was concentrated under vacuum to give a residue which was purified by column chromatography [column dimensions: diameter: 1.5 cm, height: 10 cm, silica: 230-400 mesh] and eluted with hexanes (100 mL) followed by a mixture of hexanes/ethyl acetate (95:5, 100 mL). The hexane/ethyl acetate fractions were combined and concentrated under vacuum to give a gummy mass.

The product POH carbamate exhibited a weight of 120 mg and a yield of 31%. $^1$H-NMR (400 MHz, CDCl$_3$): δ 0.9 (m, 2H), 1.4 (m, 2H), 1.7 (m, 7H*), 1.95 (m, 8H*), 2.1 (m, 4H), 2.3 (s, 3H), 4.4 (d, 2H), 4.7 (dd, 2H), 5.6 (br d, 2H), 6.6 (s, 1H), 7.0 (br s, 1H), 7.12 (d, 1H), 7.19 (d, 1H), 7.4 (d, 2H), 7.85 (d, 2H); MS, m/e: 751.8 (M$^+$3%), 574.3 (100%), 530.5 (45%), 396 (6%). * N.B. further 2H overlapping from presumed impurity discounted in NMR integration.

Example 2

In Vitro Cytotoxicity Studies of Dimethyl Celecoxib bisPOH Carbamate (POH-DMC)

First cytotoxicity assays were carried out after cells were treated with dimethyl-celecoxib (DMC) alone. FIG. 1 shows the results of the MTT cytotoxicity assays performed on human malignant glioma cells U87, A172 and U251 with DMC alone.

Figure 2:
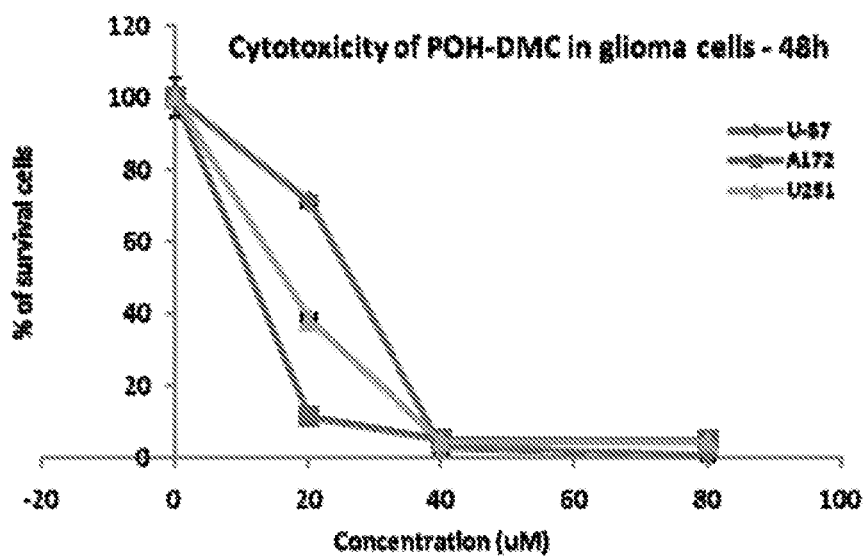
FIG. 2 shows the results of the MTT cytotoxicity assays demonstrating the efficacy of the POH-DMC conjugate in killing U87, A172 and U251 human glioma cells according to the present invention.

Then US87, A172 and U251 cells were treated with dimethyl celecoxib bisPOH carbamate (POH-DMC) (e.g., synthesized by the method in Example 1), and the MTT cytotoxicity assays performed (FIG. 2). The results suggest that POH carbamate POH-DMC exhibited much better cytotoxicity than DMC alone.

Example 3

Synthesis of Temozolomide POH Carbamate (3-methyl 4-oxo-3,4-dihydroimidazo[5,1-d][1,2,3,5] tetraxine-8-carbonyl)-carbamic acid-4-isopropenyl cyclohex-1-enylmethyl Ester)

The reaction scheme is the following:

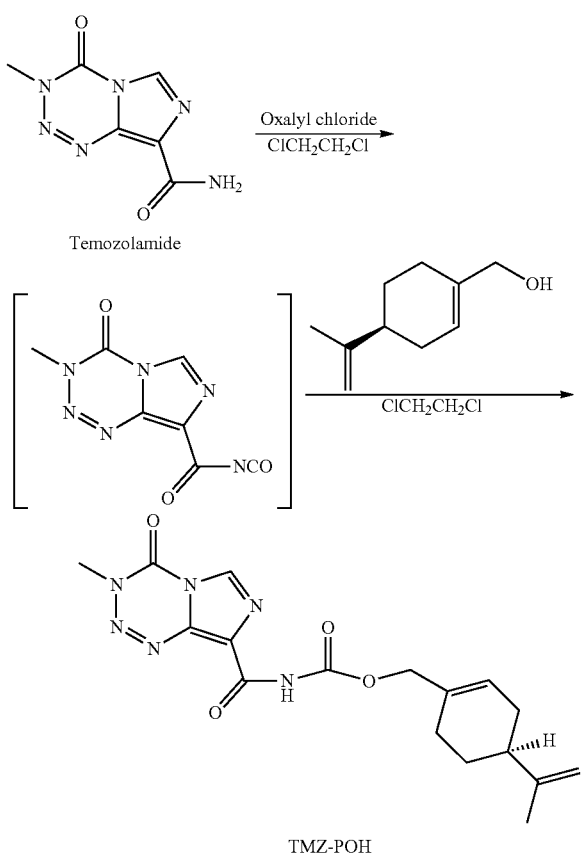

Oxalyl chloride (0.13 grams, 1.0 mmol) was added slowly to a mixture of temozolomide (OChem Incorporation, 0.1 grams, 0.5 mmol) in 1,2-dichloroethane (10 mL) over a period of 2 minutes while maintaining the temperature at 10° C. under N$_2$. The reaction mixture was allowed to warm to room temperature and then heated to reflux for 3 hours. The excess of oxalyl chloride and 1,2-dichloroethane were removed by concentration under vacuum. The resulting residue was re-dissolved in 1,2-dichlorethane (15 mL) and the reaction mixture was cooled to 10° C. under N$_2$. A solution of perillyl alcohol (0.086 grams, 0.56 mmol) in 1,2-dichloroethane (3 mL) was added over a period of 5 minutes. The reaction mixture was allowed to warm to room temperature and stirred for 14 hours. 1,2-dichloroethane was concentrated under vacuum to give a residue, which was triturated with hexanes. The resulting yellow solid was filtered and washed with hexanes. Weight: 170 mg; Yield: 89%. $^1$H-NMR (400 MHz, CDCl$_3$): δ 1.4-2.2 (m, 10H), 4.06 (s, 3H), 4.6-4.8 (m, 4H), 5.88 (br s, 1H), 8.42 (s, 1H), 9.31 (br s, 1H); MS, no molecular ion peak was observed. m/e: 314 (100%), 286.5 (17%), 136 (12%).

Alternatively, temozolomide POH carbamate was synthesized according to the following procedure. Oxalyl chloride (0.13 grams, 1.0 mmol) was added slowly to a mixture of temozolomide (OChem Incorporation, 0.1 grams, 0.5 mmol) in 1,2-dichloroethane (10 mL) over a period of 2 minutes while maintaining the temperature at 10° C. under N₂. The reaction mixture was allowed to warm to room temperature and then heated to reflux for 3 hours. The excess of oxalyl chloride and 1,2-dichloroethane were removed by concentration under vacuum. The resulting residue was re-dissolved in 1,2-dichlorethane (15 mL) and the reaction mixture was cooled to 10° C. under N₂. A solution of perillyl alcohol (0.086 grams, 0.56 mmol) in 1,2-dichloroethane (3 mL) was added over a period of 5 minutes. The reaction mixture was allowed to warm to room temperature and stirred for 14 hours. 1,2-Dichloroethane was concentrated under vacuum to give a residue, which was purified by a short silica-plug column (column dimensions: diameter: 2 cm, height: 3 cm, silica: 230-400 mesh) and eluted with a mixture of hexanes/ethyl acetate (1:1, 100 mL). The hexane/ethyl acetate fractions were combined and concentrated under vacuum to give a white solid residue which was triturated with heptanes and filtered to obtain a white solid. Weight: 170 mg; Yield: 89%. ¹H-NMR (400 MHz, CDCl3): 1.4-2.2 (m, 10H), 4.06 (s, 3H), 4.6-4.8 (m, 4H), 5.88 (br s, 1H), 8.42 (s, 1H), 9.31 (br s, 1H); MS, no molecular ion peak was obsened, m/e: 314 (100%), 286.5 (17%), 136 (12%).

Example 4

In Vitro Cytotoxicity Studies of Temozolomide POH Carbamate (POH-TMZ)

Figure 3:
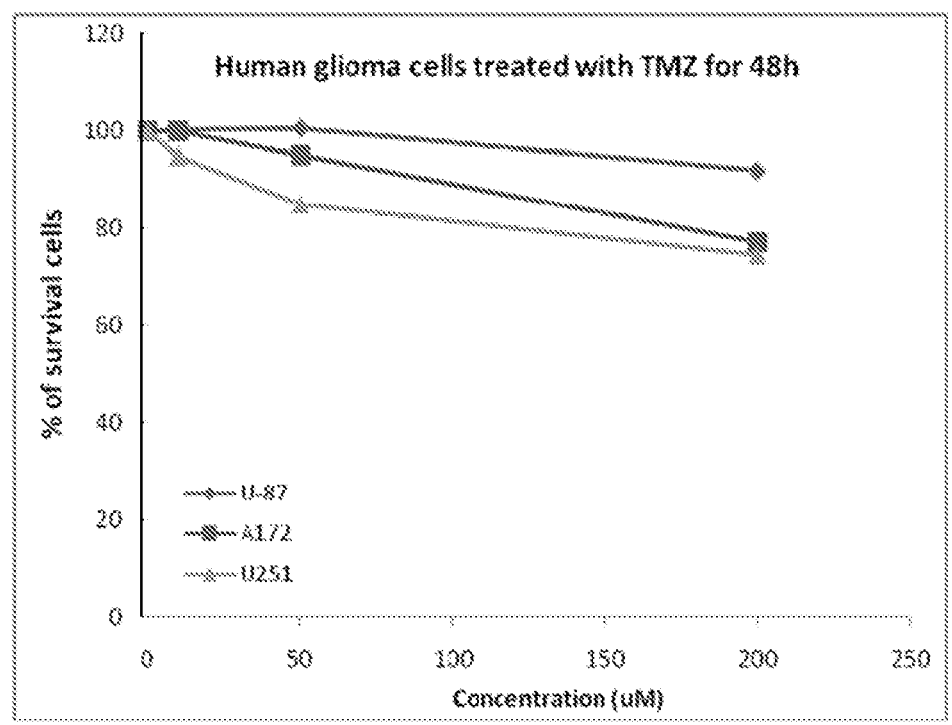
FIG. 3 shows the results of the MTT cytotoxicity assays demonstrating the efficacy of temozolomide (TMZ) in killing U87, A172 and U251 human glioma cells.

First cytotoxicity assays were carried out after cells were treated with temozolomide (TMZ) alone, the standard alkylating agent used in the treatment of malignant gliomas. FIG. 3 shows the results of the MTT cytotoxicity assays performed on human malignant glioma cells U87, A172 and U251 with TMZ alone. Increasing concentrations of TMZ had minimal cytotoxicity towards the cell lines tested.

Figure 4:
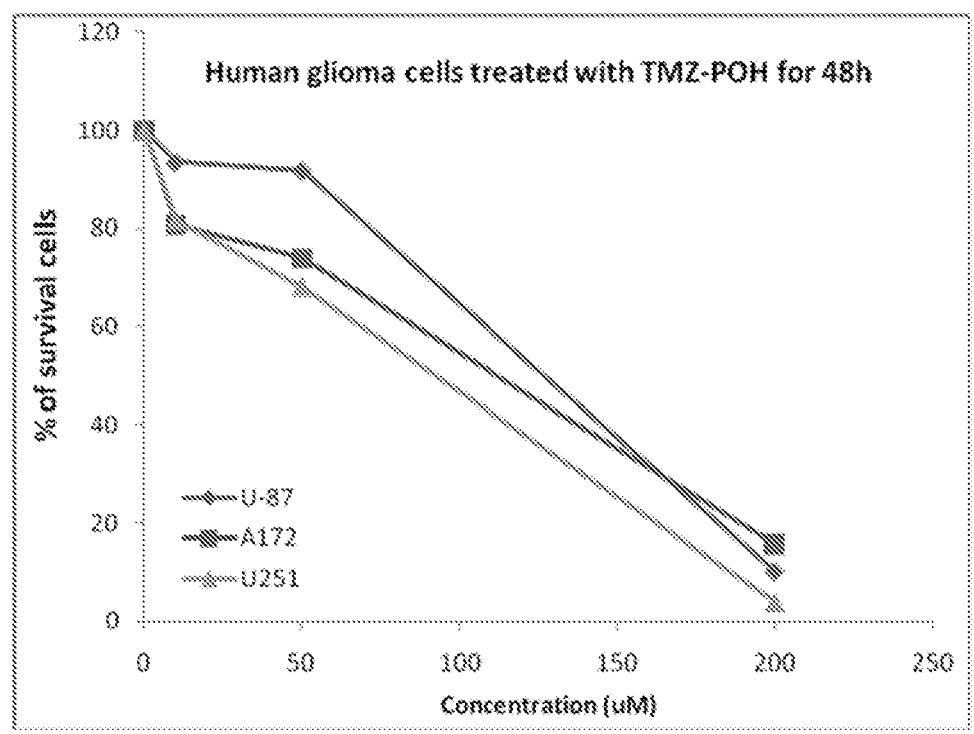
FIG. 4 shows the results of the MTT cytotoxicity assays demonstrating the efficacy of the POH-TMZ conjugate in killing U87. A172, and U251 human glioma cells according to the present invention.

The TMZ-resistant glioma cell lines U87, A172 and U251 cells were treated with temozolomide POH carbamate (POH-TMZ) (e.g., synthesized by the method in Example 3). The MTT assay results (FIG. 4) showed that POH carbamate POH-TMZ exhibited substantially higher kill rates of the various human glioma cells compared to TMZ alone.

Example 5

Synthesis of Rolipram POH Carbamate (4-(3-cyclopentyloxy-4-methoxy phenyl)-2-oxo-pyrrolidine-1-carboxylic Acid 4-isopropenyl cyclohex-1-enylmethyl Ester)

The reaction scheme is the following:

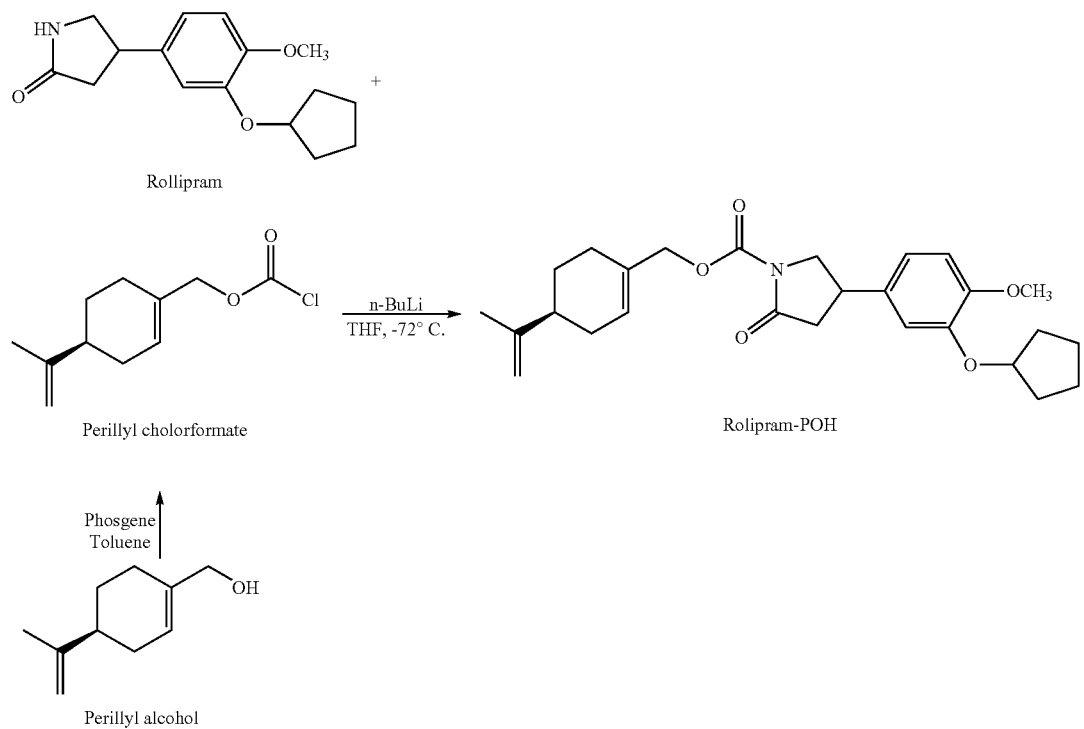

Phosgene (20% in toluene, 13 ml, 26.2 mmol) was added to a mixture of perillyl alcohol (2.0 grams, 13.1 mmol) and potassium carbonate (5.4 grams, 39.1 mmol) in dry toluene (30 mL) over a period of 30 minutes while maintaining the temperature between 10° C. to 15° C. The reaction mixture was allowed to warm to room temperature and stirred for 8.0 hours under N₂. The reaction mixture was quenched with water (30 mL) and the organic layer separated. The aqueous layer was extracted with toluene 20 mL) and the combined organic layer washed with water (50 mL×2), brine (15%, 30 mL) and dried over sodium sulfate (20 grams). The filtered organic layer was concentrated under vacuum to give perillyl chloroformate as an oil. Weight: 2.5 grams; Yield: 89%, ¹H-NMR (400 MHz, CDCl₃): δ 1.15 (m, 1H). 1.7 (s, 3H), 1.8 (m, 1H), 2.0 (m, 1H), 2.2 (m, 4H), 4.7 (dd, 4H); 5.87 (m, 1H).

Butyl lithium (2.5 M, 0.18 mL, 0.45 mmol) was added to a solution of rolipram (G L synthesis, Inc., 0.1 grams, 0.36 mmol) in dry THF at −72° C. over a period of 5 minutes under $N_2$. After the reaction mixture was stirred for 1.0 hours at −72° C., perillyl chloroformate (dissolved in 4 mL THF) was added over a period of 15 minutes while maintaining the temperature at −72° C. The reaction mixture was stirred for 2.5 hours and quenched with saturated ammonium chloride (5 mL). The reaction mixture was allowed to warm to room temperature and extracted with ethyl acetate (2×15 mL). The combined organic layer was washed with water (15 mL), brine (15%, 15 mL), and then dried over sodium sulfate. The filtered organic layer was concentrated to give an oil which was purified by column chromatography [column dimensions: diameter: 1.5 cm, height: 10 cm, silica: 230-400 mesh] and eluted with a mixture of 8% ethyl acetate/hexanes (100 mL) followed by 12% ethyl acetate/hexanes (100 mL). The 12% ethyl acetate/hexanes fractions were combined and concentrated under vacuum to yield a gummy solid. Weight: 142 mg; Yield: 86%. $^1$H-NMR (400 MHz, $CDCl_3$): δ 1.5 (m, 1H), 1.6 (m, 2H), 1.7 (s, 3H), 1.9 (m, 6H), 2.2 (m, 5H), 2.7 (m, 1H), 2.9 (m, 1H), 3.5 (m, 1H), 3.7 (m, 1H), 3.8 (s, 3H), 4.2 (m, 1H), 4.7 (m, 6H), 5.8 (br s, 1H), 6.8 (m, 3H); MS, m/e: 452.1 ($M^{+1}$ 53%), 274.1 (100%), 206.0 (55%).

Example 6

In Vitro Cytotoxicity Studies of Rolipram POH Carbamate (POH-Rolipram)

Figure 5:
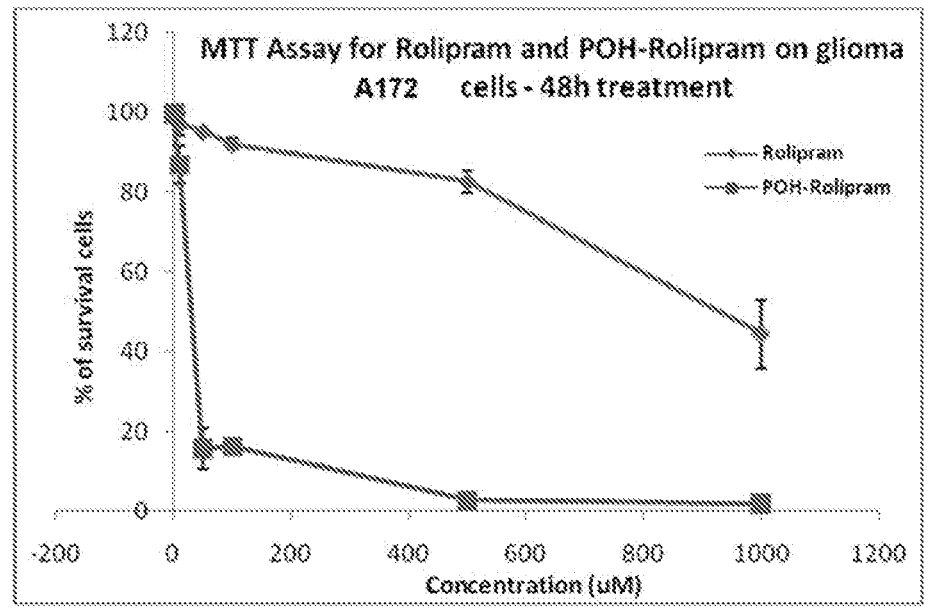
FIG. 5 shows the results of the MTT cytotoxicity assays demonstrating the efficacy of the POH-Rolipram conjugate and Rolipram in killing A172 human glioma cells.
Figure 6:
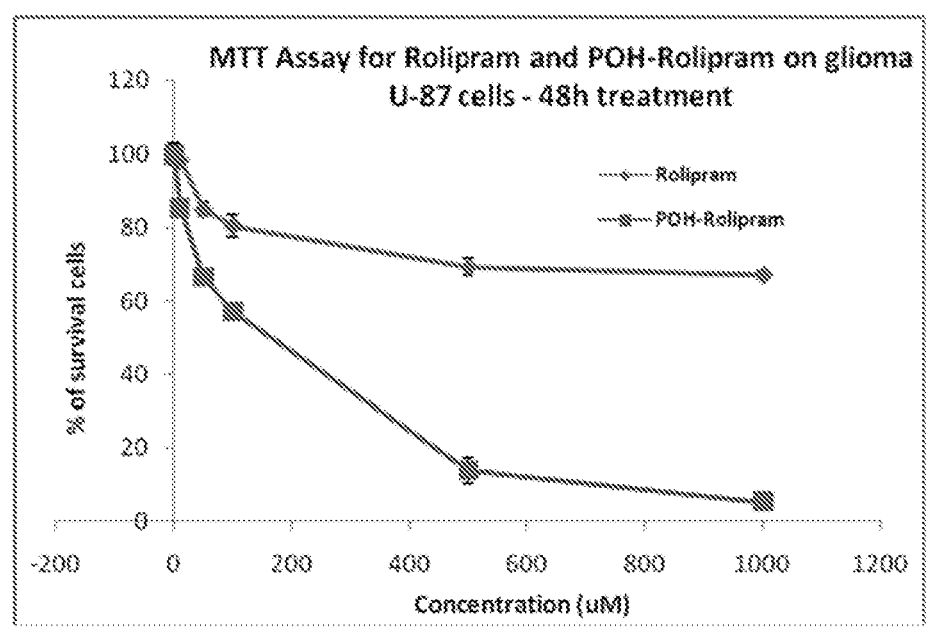
FIG. 6 shows the results of the MTT cytotoxicity assays demonstrating the efficacy of the POH-Rolipram conjugate and Rolipram in killing U87 human glioma cells.
Figure 7:
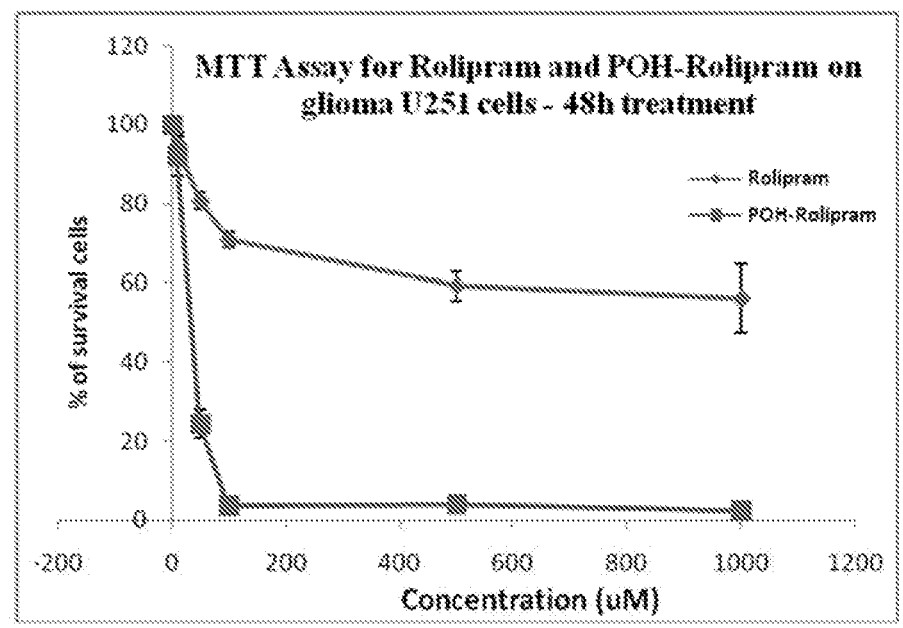
FIG. 7 shows the results of the MTT cytotoxicity assays demonstrating the efficacy of the POH-Rolipram conjugate and Rolipram in killing U251 human glioma cells.
Figure 8:
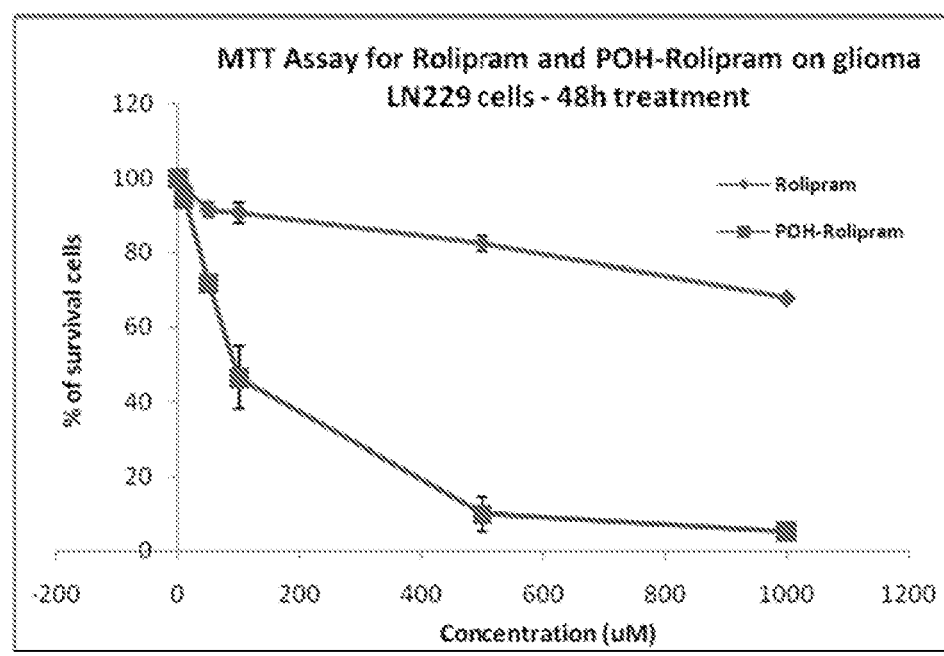
FIG. 8 shows the results of the MTT cytotoxicity assays demonstrating the efficacy of the POH-Rolipram conjugate and Rolipram in killing L229 human glioma cells.

To compare the cytotoxicity of Rolipram POH Carbamate (POH-Rolipram) (e.g., synthesized by the method in Example 5) with rolipram, a type IV phosphodiesterase inducing differentiation and apoptosis in glioma cells, A172, U87, U251 and LN229 human glioma cells were treated with either POH-Rolipram or rolipram for 48 hours. The MTT assay results are shown in FIGS. 5 to 8. POH-Rolipram exhibited substantially higher kill rates compared to rolipram alone for each of the several different human glioma cell types. FIG. 5 shows the MTT assay for increasing concentrations of rolipram and POH-rolipram for A-172 cells. Rolipram alone demonstrates an IC50 of approximately 1000 uM (1 mM). In the presence of POH-rolipram, IC50 is achieved at concentrations as low as 50 uM. FIG. 6 shows the MTT assay for increasing concentrations of rolipram with U-87 cells. IC50 is not met at 1000 uM. On the other hand, IC50 is achieved at 180 uM with POH-rolipram. FIG. 7 shows that IC50 for rolipram alone for U251 cells is achieved at 170 uM; plateau cytotoxicity is reached at 60%. POH-rolipram achieves IC50 at 50 uM, with almost 100% cytoxicity at 100 uM. FIG. 8 shows that IC50 for rolipram alone for LN229 cells is not achieved even at 100 uM. On the other hand, IC50 for POH-rolipram is achieved at 100 uM, with almost 100% cytoxicity at 10 uM.

Example 7

In Vivo Tumor Growth Inhibition by POH Fatty Acid Derivatives

Figure 9A:
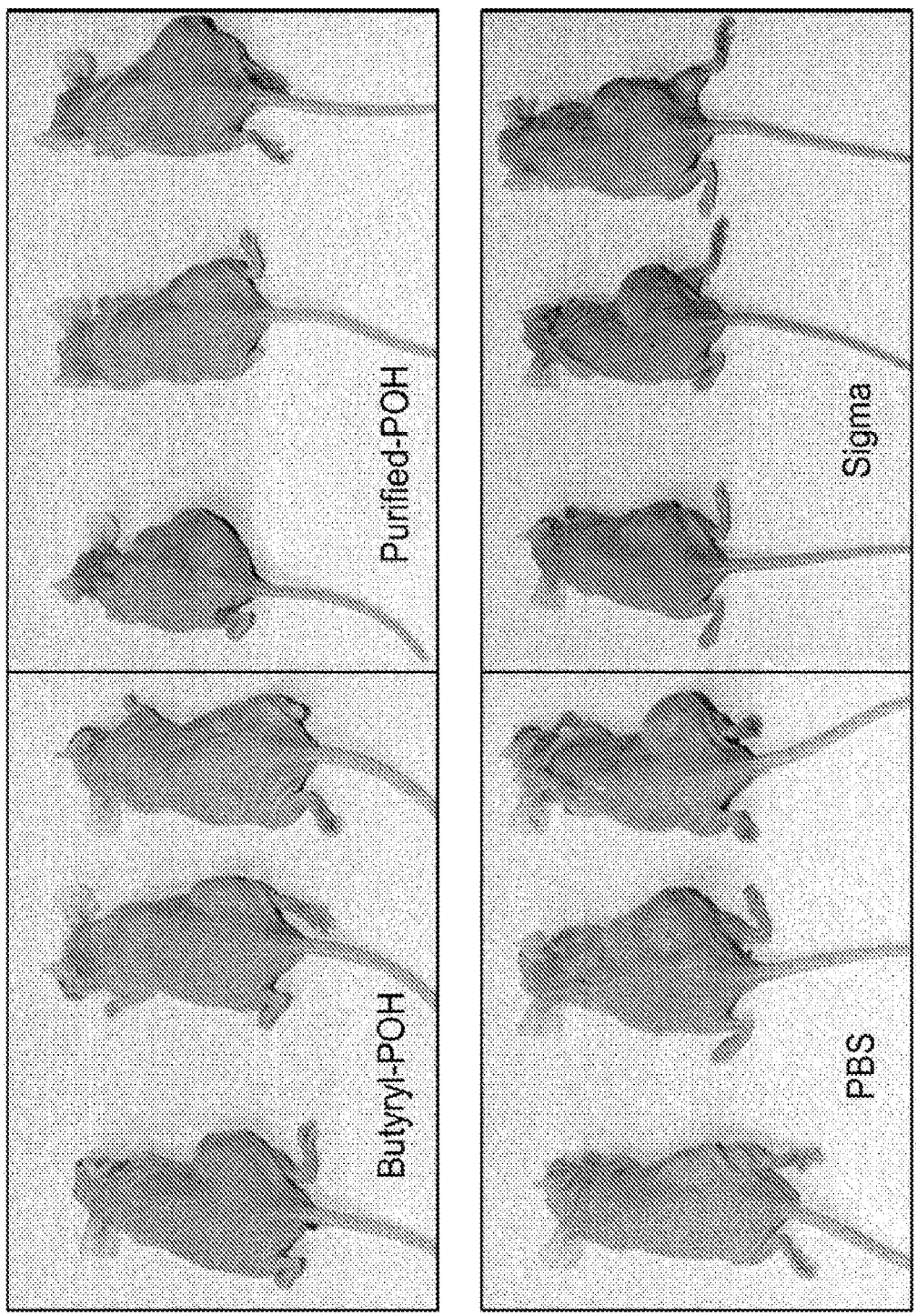
FIGS. 9A and 9B show the inhibition of tumor growth by butyryl-POH in mouse models.
Figure 9B:
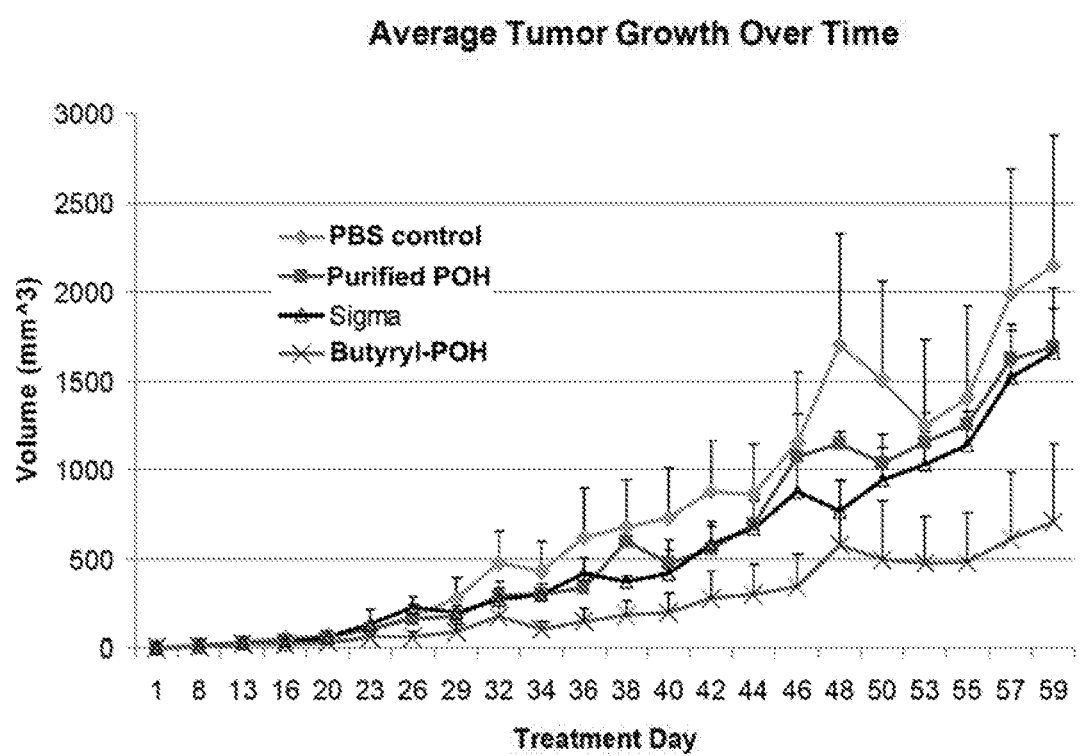

Inhibition of tumor growth by butyryl-POH was studied in a nude mouse subcutaneous glioma model. Mice were injected with U-87 glioma cells (500,000 cells/injection) and allowed to form a palpable nodule over two weeks. Once palpable nodule was formed, the mice were treated with local application of various compounds as indicated in FIGS. 9A and 9B via a Q-tip (1 cc/application/day) over a period of 8 weeks. FIG. 9A shows the images of subcutaneous U-87 gliomas in nude mice treated with butyryl-POH, purified (S)-perillyl alcohol having a purity greater than 98.5% ("purified POH"), POH purchased from Sigma chemicals, or phosphate buffered saline (PBS; negative control). FIG. 9B shows average tumor growth over time (total time period of 60 days). Butyryl-POH demonstrated the greatest inhibition of tumor growth, followed by purified POH and Sigma POH.

Example 8

Figure 10:
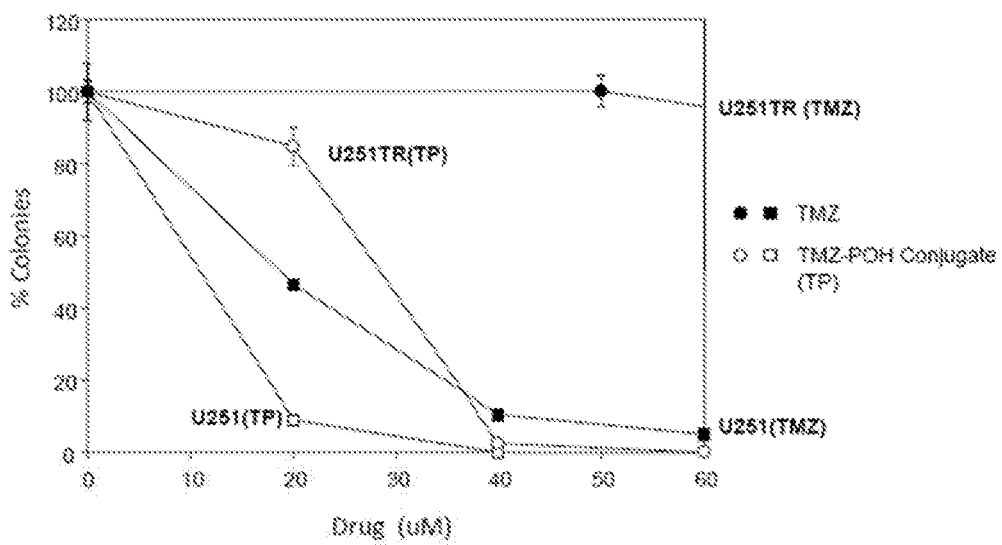
FIG. 10 shows the results of a Colony forming Assay (CFA) demonstrating the cytotoxic effect of TMZ and TMZ-POH on TMZ sensitive (U251) and TMZ resistant (U251TR) U251 cells.

In Vitro Cytotoxicity Studies of Temozolomide (TMZ) and Temozolomide POH Carbamate (POH-TMZ) on TMZ Sensitive and Resistant Glioma Cells Colony forming assays were carried out after cells were treated with TMZ alone, POH alone, and the TMZ-POH conjugate. The colony forming assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 10 shows the results of the colony forming assays performed on TMZ sensitive (U251) and TMZ resistant (U251IR) U251 cells with TMZ or TMZ-POH. TMZ demonstrated cytotoxicity towards TMZ sensitive U251 cells, but had minimal cytotoxicity towards TMZ resistant U251 cells. TMZ-POH demonstrated cytotoxicity towards both TMZ sensitive and TMZ resistant U251 cells.

Figure 11:
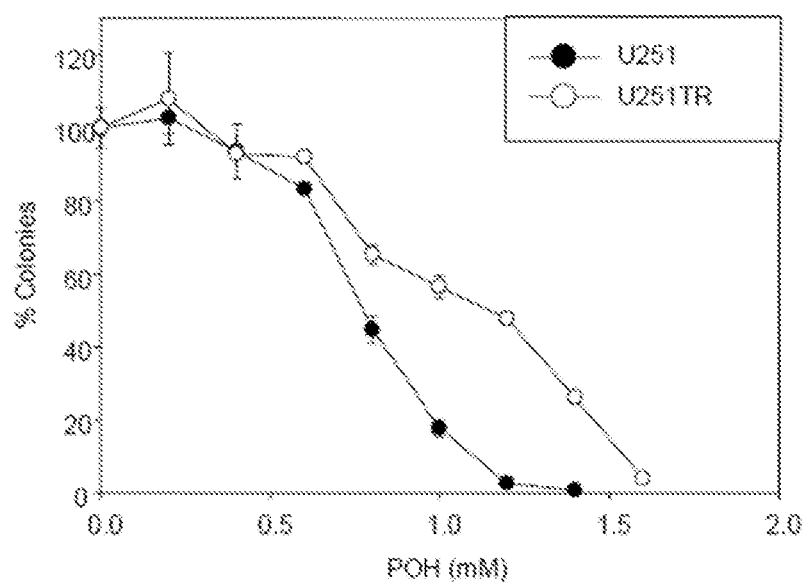
FIG. 11 shows the results of a Colony forming Assay (CFA) demonstrating the cytotoxic effect of POH on TMZ sensitive (U251) and TMZ resistant (U251TR) U251 cells.

FIG. 11 shows the results of the colony forming assays performed on TMZ sensitive (U251) and TMZ resistant (U251TR) U251 cells with POH. POH demonstrated cytotoxicity towards both TMZ sensitive and TMZ resistant U251 cells. POH-TMZ (FIG. 10) exhibited substantially greater potency compared to POH alone (FIG. 11) in the colony forming assays.

Example 9

Figure 12:
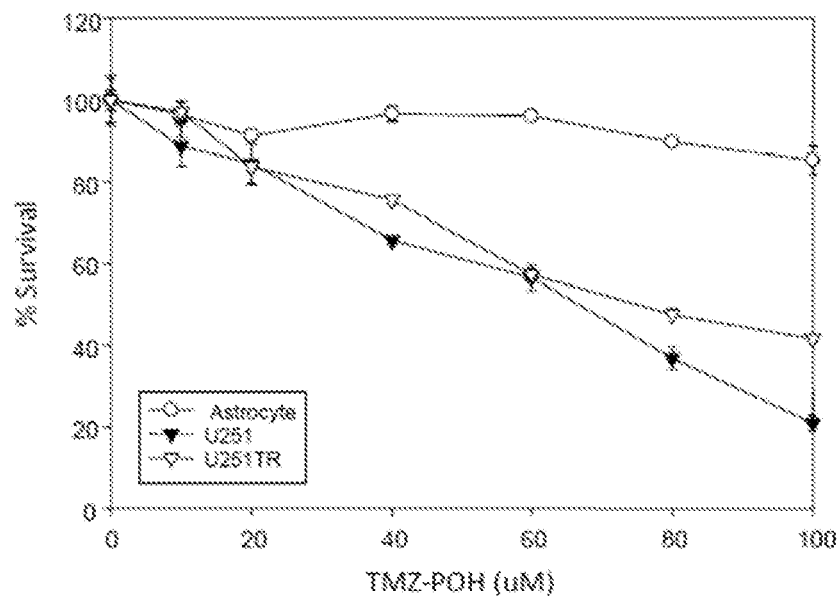
FIG. 12 shows the results of the MTT cytotoxicity assays demonstrating the efficacy of the POH-TMZ conjugate in killing U251 cells, U251TR cells, and normal astrocytes.

In Vitro Cytotoxicity Studies of Temozolomide POH Carbamate (POH-TMZ) on U251 Cells, U251TR Cells, and Normal Astrocytes MTT cytotoxicity assays were carried out after cells were treated with the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 12 shows the results of the MTT cytotoxicity assays performed on TMZ sensitive cells (U251), TMZ resistant cells (U251TR) and normal astrocytes. TMZ-POH demonstrated cytotoxicity towards both TMZ sensitive and TMZ resistant U251 cells, but not towards normal astrocytes.

Example 10

Figure 13:
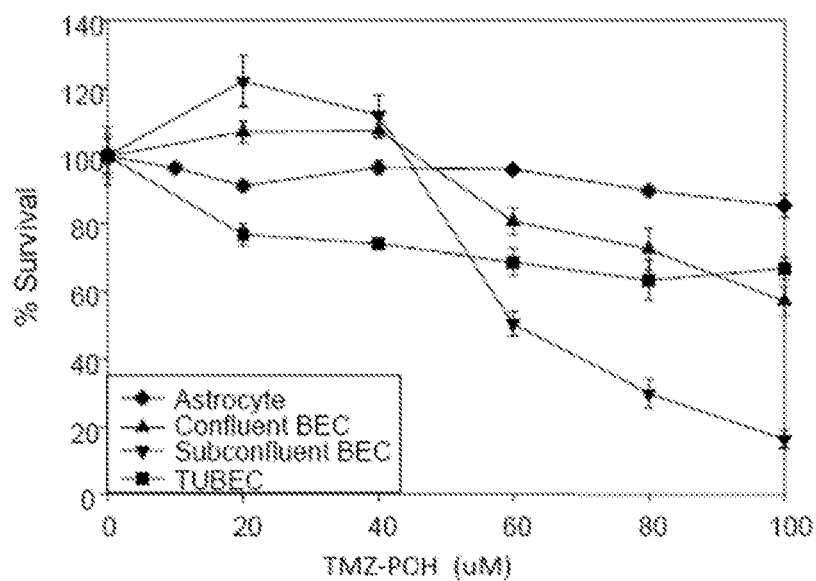
FIG. 13 shows the results of the MTT cytotoxicity assays demonstrating the efficacy of the POH-TMZ conjugate in killing normal astrocytes, brain endothelial cells (BEC; confluent and subconfluent), and tumor brain endothelial cells (TuBEC).

In Vitro Cytotoxicity Studies of Temozolomide POH Carbamate (POH-TMZ) on BEG, TuBEC, and Normal Astrocytes MTT cytotoxicity assays were carried out after cells were treated with the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2)100-8 FIG. 13 shows the results of the MTT cytotoxicity assays performed on normal astrocytes, brain endothelial cells (BEC; confluent and subconfluent), and tumor brain endothelial cells (TuBEC). TMZ-POH did not induce significant cytotoxicity on normal astrocytes, confluent BEC, or TuBEC. Mild to moderate cytotoxicity was demonstrated in subcontinent BEC at high concentrations of TMZ-POH.

Example 11

Figure 14:
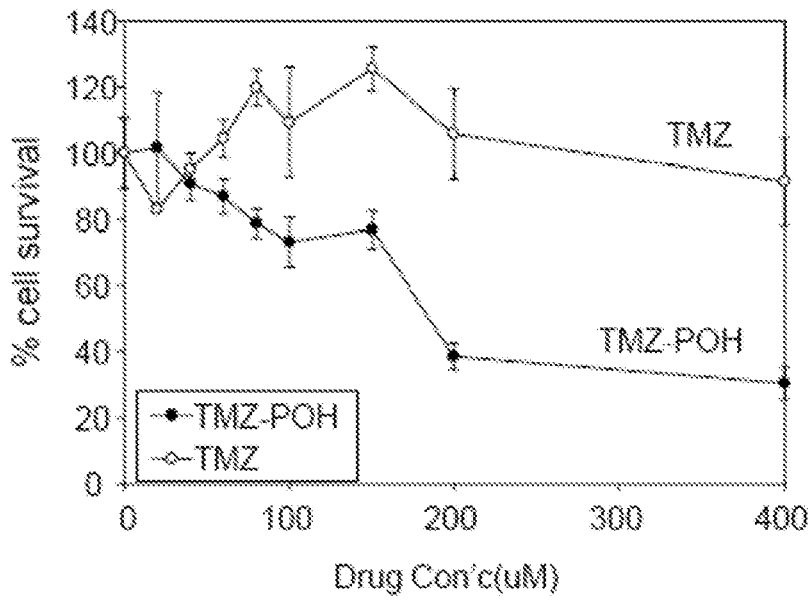
FIG. 14 shows the results of the MTT cytotoxicity assays demonstrating the efficacy of TMZ and the POH-TMZ conjugate in killing USC-04 glioma cancer stem cells.
Figure 15:
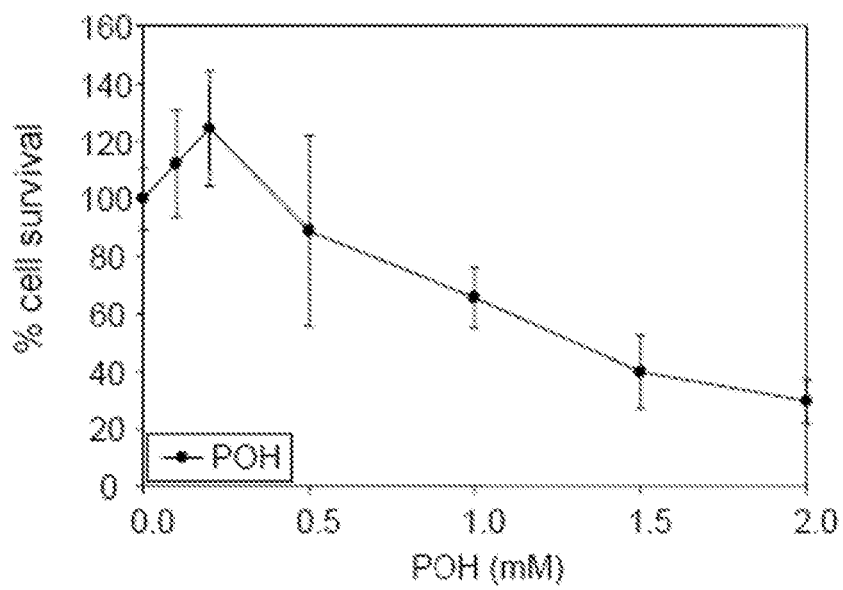
FIG. 15 shows the results of the MTT cytotoxicity assays demonstrating the efficacy of POH in killing USC-04 glioma cancer stem cells.

In Vitro Cytotoxicity Studies of Temozolomide (TMZ) and Temozolomide POH Carbamate (POH-TMZ) on USC-04 Glioma Cancer Stem Cells MTT cytotoxicity assays were carried out after cells were treated with the TMZ alone, POH alone, or the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 14 shows the results of the MTT cytotoxicity assays performed on USC-04 glioma cancer stem cells. TMZ did not induce significant cytotoxicity with increasing concentrations (0-400 uM). TMZ-POH demonstrated evidence of cytotoxicity with IC50 at 150 uM. FIG. 15 shows the results of the MTT cytotoxicity assays performed on USC-04 glioma cancer stem cells treated with POH. POH demonstrated cytotoxicity on USC-04 with increasing concentrations (0-2 mM).

Example 12

Figure 16:
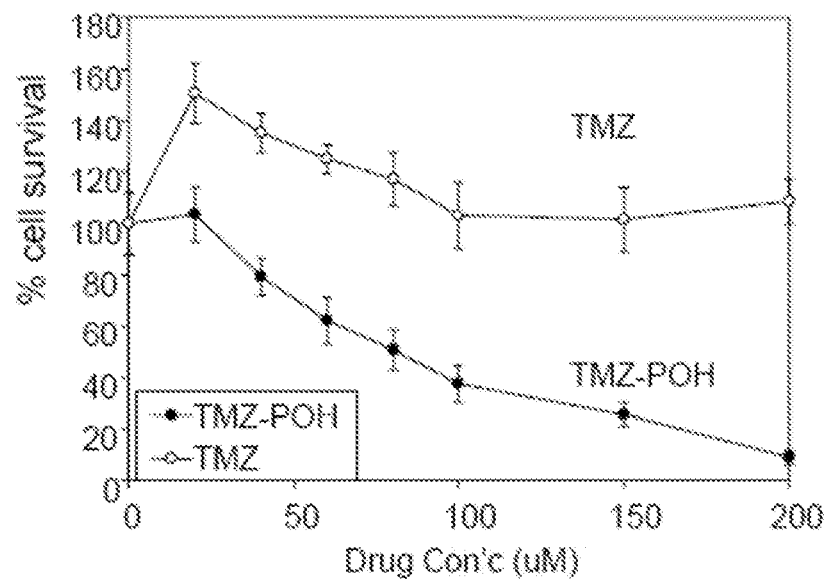
FIG. 16 shows the results of the MTT cytotoxicity assays demonstrating the efficacy of TMZ and the POH-TMZ conjugate in killing USC-02 glioma cancer stem cells.
Figure 17:
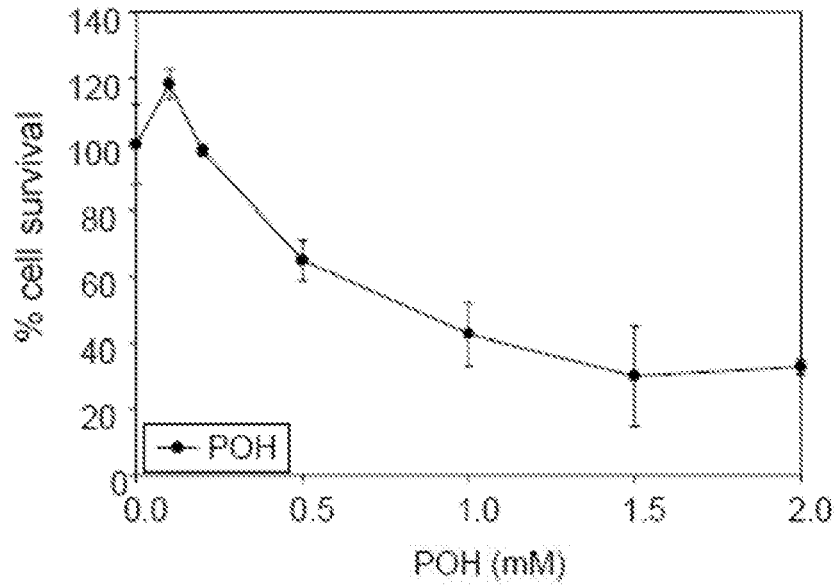
FIG. 17 shows the results of the MTT cytotoxicity assays demonstrating the efficacy of POH in killing USC-02 glioma cancer stem cells.

In Vitro Cytotoxicity Studies of Temozolomide (TMZ) and Temozolomide POH Carbamate (POH-TMZ) on USC-02 Glioma Cancer Stem Cells MTT cytotoxicity assays were carried out after cells were treated with the TMZ alone, POH alone, or the TMZ-POH conjugate. The MTT cytotoxicity assays were carried out as described in Chen T C, et al Green tea epigallocatechin gallate enhances therapeutic efficacy of temozolomide in orthotopic mouse glioblastoma models. *Cancer Lett.* 2011 Mar. 28; 302(2):100-8. FIG. 16 shows the results of the MTT cytotoxicity assays performed on USC-02 glioma cancer stem cells. TMZ did not induce significant cytotoxicity with increasing concentrations (0-400 uM). TMZ-POH demonstrated evidence of cytotoxicity with IC50 at 60 uM. FIG. 17 shows the results of the MTT cytotoxicity assays performed on USC-02 glioma cancer stem cells treated with POH. POH demonstrated cytotoxicity on USC-02 with increasing concentrations (0-2 mM).

Example 13

Figure 18:
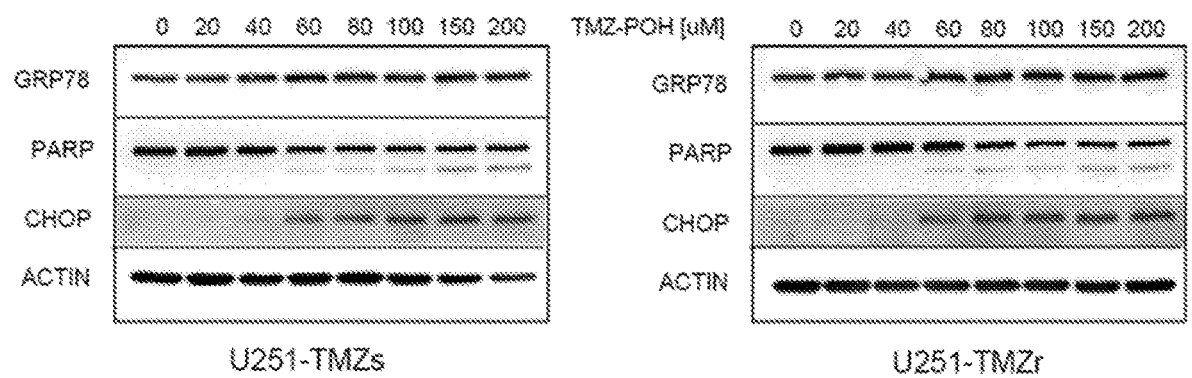
FIG. 18 shows a western blot demonstrating that TMZ-POH induces ER stress (ERS) in TMZ sensitive ("U251-TMZs") and resistant ("U251-TMZr") U251 glioma cells.

In Vitro Studies of ER Stress by Temozolomide POH Carbamate (POH-TMZ) on TMZ Sensitive and Resistant Glioma Cells Western blots were performed after TMZ sensitive and resistant glioma cells were treated with the TMZ-POH conjugate for 18 hr. FIG. 18 shows a western blot demonstrating that TMZ-POH induces ER stress (EPS) in TMZ sensitive and resistant U251 glioma cells. Activation of the proapoptic protein CHOP was shown at concentrations as low as 60 uM of TMZ-POH.

Example 14

Synthesis of Iso-POH

The reaction scheme is the following:

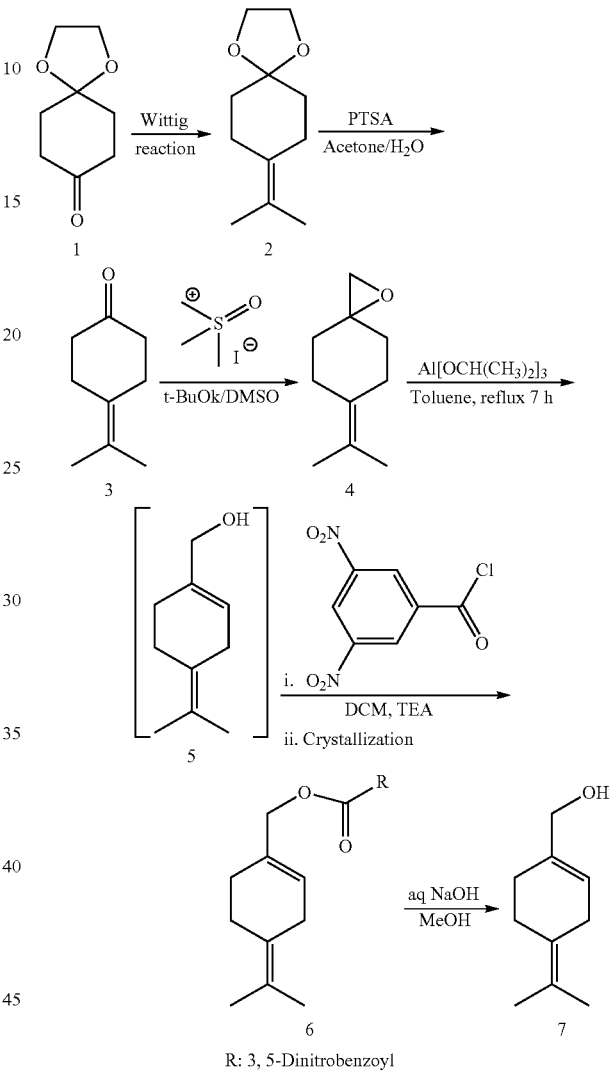

R: 3, 5-Dinitrobenzoyl

Preparation of 4-isopropylidene-1,4-dioxa-spiro[4,5] decane (2)

Isopropyltriphenylphosphonium iodide (83.02 g, 192 mmol) was added to NaH (60%, in mineral oil, 8.38 g, 192 mmol) in dry dimethyl sulfoxide (120 mL) at room temperature under a nitrogen atmosphere. The reaction mixture was slowly heated to 50° C. over a period of 15 min and maintained at 50° C. until the reaction mass became a red color (approximately 30 min). A solution of 1,4-cyclohexanedione monoethylene ketal (1, 30 g, 192 mmol) in dry dimethyl sulfoxide was added over a period of 45 min while keeping the temperature below 50° C. and the reaction was maintained at 50° C. for 16 h. The reaction mixture was cooled to room temperature, quenched with cold water (150 ml), and extracted with ethyl acetate (2×160 mL). The combined organic layer was washed with water (2×200 mL), followed by brine (10%, 250 mL) and dried over sodium sulfate. The filtered organic layer was concentrated to give a solid which was triturated with hexanes (300 mL) and the precipitated triphenylphosphine oxide was filtered off. The hexane layer was concentrated to give an oil which was purified by column chromatography. [Column dimensions dia: 6.0 cm, height: 12 cm, silica: 200 mesh, eluted hexanes (1.0 L) followed by hexane: ethyl acetate (97:3, 2.0 L)] The hexane: ethyl acetate fractions were combined and concentrated under vacuum to give an oil. Weight: 23.36 g. Weight yield: 66.7%. $^1$H-NMR (400 MHz, CDCl$_3$): δ 1.61-1.63 (t, 4H), 1.64 (s, 6H), 2.29 (m, 4H), 3.97 (s, 4H), MS (APCI method): No molecular ion peak was observed.

Preparation of 4-isopropylidene Cyclohexanone (3)

p-Toluenesulfonic acid (31.16 g, 164 mmol) was added to a solution of ketal (2, 23.0 g, 126 mmol) in acetone (2.3 L) and water (138 mL). The reaction mixture was heated to reflux and maintained at reflux for 3.5 h. The mixture was cooled to room temperature, treated with saturated sodium bicarbonate (60 ml) and concentrated under vacuum. The resulting oily residue was extracted with ethyl acetate (2×130 mL), washed with water (100 mL), then brine (100 mL), and dried over sodium sulfate. The filtered organic layer was concentrated under vacuum to give an oil. Weight: 16 g. Weight yield: 92%. $^1$H-NMR (400 MHz, CDCl$_3$): δ 1.69 (s, 6H), 2.35 (t, 4H), 2.50 (t, 4H). MS (APCI method): No molecular ion peak was observed (Note: $^1$H-NMR showed the presence of ~2% of ketal 2 but used without purification).

Preparation of 4-isopropylidene-1-oxa-spiro[2,5] octane (4)

Potassium i-butoxide (3.3 g, 29.4 mmol) was added to a mixture of ketone (3, 2.5 g, 18.1 mmol) and trimethylsulfoxonium iodide (6.45 g, 29.4 mmol) in dry dimethyl sulfoxide (40 mL) under nitrogen atmosphere at room temperature. The mixture was stirred for 4.0 h at room temperature. The reaction was quenched by the addition of cold water (40 mL) and extracted with ethyl acetate (2×60 mL). The combined organic layer was washed with water (75 mL) followed by brine (75 mL) and dried over sodium sulfate. The filtered organic layer was concentrated under vacuum to give an oil. Weight: 2.13 g. Weight yield: 77%. $^1$H-NMR (400 MHz, CDCl$_3$): δ1.42-1.50 (m, 2H), 1.65 (s, 6H), 2.31 (t, 4H), 2.61 (s, 2H). MS (APCI method): No molecular ion peak was observed.

Preparation of 3,5-dinitrobenzoic acid 4-isopropylidene cyclohex-1-enylmethyl Ester (6)

Aluminum isopropoxide (5.93 g, 29.0 mmol) was added to a mixture of epoxide (4, 4.0 g, 26.2 mmol) in toluene (80 mL) and the mixture was heated to reflux for 7.0 h. The mixture was cooled to room temperature and quenched with saturated potassium sodium tartrate solution. The organic layer was separated, washed with water (40 mL), followed by brine (40 mL), and dried over sodium sulfate. The filtered organic layer was concentrated under vacuum to give crude isoperillyl alcohol (5) as an oil. Weight: 4.0 g, Weight yield: 100%, Purity: ~85-90% (by GC area percent, Actual yield ca: 85%).

Triethylamine (5.1 mL, 36.6 mmol) was added to a solution of crude isoperillyl alcohol (5, 4.0 g, 26.2 mmol) in dichloromethane (50 mL). After stirring for 15 min, 3,5-dinitrobenzoyl chloride (6.3 g, 27.5 mmol) was added over a period of 0.25 h. The reaction mixture was stirred for 3.0 h and quenched with water (30 mL). The organic layer was separated, washed with water (40 mL), and dried over sodium sulfate. The filtered organic layer was concentrated under vacuum to give a pale yellow solid (8.5 g), which was recrystallized from acetone to give pure ester 6 as a pale yellow solid. Mp: 138-140° C. (acetone). Weight: 5.7 g. Yield: 62% (from epoxide). $^1$H-NMR (400 MHz, CDCl$_3$): δ 1.68 (s, 3H), 1.71 (s, 3H), 2.18 (t, 2H), 2.40 (t, 2H), 2.87 (br s, 2H), 4.85 (s, 2H); 5.88 (s, 1H), 9.17 (t, 1H), 9.24 (s, 1H). MS (APCI method): m/e: 247.1 (5%), 149.07 (7%) 135.1 (100%), 107.1 (9%).

Preparation of Isoperillyl Alcohol (7)

Aqueous sodium hydroxide (1.43 g, 35.7 mmol, dissolved in 12.5 mL of water) was added to an ice-cold solution of 3,5-dinitrobenzoic acid 4-isopropylidene-cyclohex-1-enyl-methyl ester (6, 5.63 g, 16.2 mmol) in methanol (56 mL) over a period of 0.25 h. The reaction mixture was allowed to warm to room temperature and then stirred for 3.0 h. The methanol was concentrated under vacuum to a minimum stirring volume and the mixture was suspended in water (40 mL). The resulting mixture was extracted with ethyl acetate (2×50 mL). The organic layer was washed with water (2×50 mL), then brine (50 mL), and dried over sodium sulfate. The filtered organic layer was concentrated under vacuum to give pure isoperillyl alcohol as an oil. Weight: 2.35 g, Yield: 95%, Purity: 97% (by GC AUC). $^1$H-NMR (400 MHz, CDCl$_3$): δ 1.65 (s, 3H), 1.69 (s, 3H), 1.77 (bs, OH), 2.09 (m, 2H), 2.33 (t, 2H), 2.79 (br s, 2H); $^{13}$C-NMR: δ 20.38, 20.80, 26.95, 27.60, 29.86, 67.49, 122.88, 123.04, 127.92, 138.37. MS (APCI method): m/e: 152 (M+, 3.5%), 135.07 (100%), 107.12 (5%). However, the mass spectrum showed four small peaks (~5%) at M+: 207.06, 269.1, 287.09 & 301 which were not characterized.

Example 15

Alternative Synthesis of Iso-POH

The reaction scheme is the following:

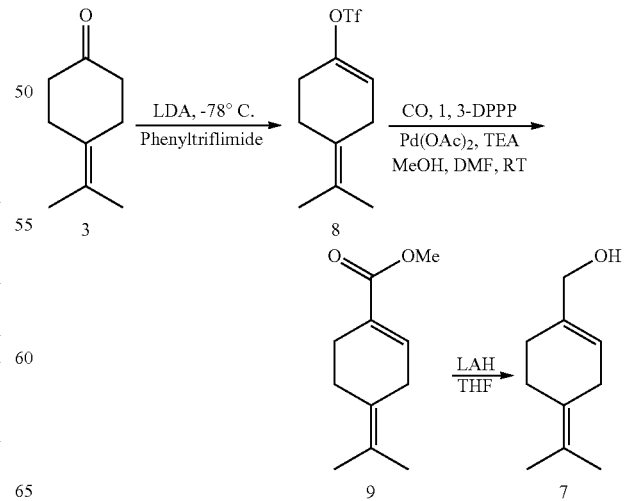

Preparation of trifluoromethanesulfonic Acid-4-isopropylidenecyclohex-1-enyl Ester (8)

2.5 M solution of n-Butyl lithium in hexanes (5.6 mL, 14.1 mmol) was added to a solution of diisopropylamine (1.98 mL, 14.1 mmol) in dry THF (30 mL) at −78° C. over a period of 0.5 hr. After stirring for 1.0 h at −78° C., a solution of ketone (3, 1.3 g, 9.4 mmol) in dry THF (10 mL) was added over a period of 10 min while maintaining the temperature below −78° C. The reaction mixture was stirred for 1.0 h at −78° C. A solution of phenyltriflimide (3.53 g, 9.86 mmol) in THF (15 mL) was added slowly while maintaining the temperature below −78° C. The reaction mixture was slowly warmed to 0° C., maintained for 2.0 h at 0° C. and then quenched with satd ammonium chloride solution. The separated organic layer was washed with water (15 mL), brine (15 mL) and dried over sodium sulfate. The filtered organic layer was concentrated under vacuum and the resulting residue was purified by column chromatography. [Column dimensions: dia: 6.0 cm, height: 12 cm, silica: 200 mesh, eluted with hexanes (200 mL)] The similar fractions were combined and concentrated under vacuum which gave an oil. Weight: 0.9 g. Weight yield: 38%. $^1$H-NMR (400 MHz, CDCl$_3$): δ 1.68 (s, 3H), 1.71 (s, 3H), 2.37 (m, 2H), 2.46 (m, 2H), 2.91 (m, 2H), 5.73 (m, 1H). MS (APCI method): No molecular ion peak was observed.

Note-1: $^1$H-NMR indicated the presence of aromatic peaks (~5%) between δ 7.42-7.57 which were attributed to the by-product trifluoro-N-phenylmethanesulfonamide.

Note-2: The compound 8 was also synthesized in low yield (28%) using triflic anhydride in the presence of 2,6-di-tert-butyl-4-methylpyridine as a base.

Preparation of 4-isopropylidene cyclohex-1-enecarboxylic Acid Methyl Ester (9)

To a solution of compound 8 (0.2 g, 0.74 mmol) in N'N-dimethylformamide (1.5 mL) was added methanol (1.0 mL), triethylamine (10.17 mL, 1.2 mmol), 1.3-bis(diphenylphosphino)propane (0.03 g, 0.07 mmol) and palladium acetate (0.04 g, 0.07 mmol). The reaction mixture was degassed and then stirred at room temperature under carbon monoxide (balloon pressure) for 5 h. The reaction mixture was diluted with ethyl acetate (15 mL) and washed with 0.5 N HCl (15 mL), brine (15 mL) and dried over sodium sulfate. The filtered organic layer was concentrated under vacuum and the resulting residue was purified by column chromatography. [Column dimensions: dia: 6.0 cm, height: 12 cm, silica: 200 mesh, eluted with hexanes (100 mL) followed by ethyl acetate:hexanes (2%, 150 mL)] The similar fractions were combined and concentrated under vacuum which gave an oil. While TLC analysis showed only a single spot, $^1$H-NMR and GC analysis indicated that the isolated material was a mixture of two primary components that co-eluted by TLC. Weight: 0.11 g. Weight yield: 82%. $^1$H-NMR (400 MHz, CDCl$_3$) indicated the presence of peaks corresponding to the methyl ester (9) along with an unknown impurity. GC analysis confirmed that it is mainly a mixture of two compounds with a ratio of 3:1. MS (APCI method): m/e: 180 (M$^+$, 5%), 180.9 (M$^{+1}$, 100%). The other peaks (≤5%) at M+: 197.8, 247.0 & 274.0 were not characterized. The crude mixture was taken forward without purification.

Preparation of isoperillyl alcohol (7): Methyl ester (9, 11 g, 0.6 mmol) in dry THF (10 mL) was added to a cold solution of LAH (0.03 g, 0.78 mmol) in dry THF (10 mL) over a period of 2 min. The reaction mixture was slowly heated to reflux and maintained for 3.0 h. The mixture was cooled to 5° C. and quenched with satd sodium sulfate (1.5 mL). The precipitated lithium salts were filtered off and washed with hot ethyl acetate (20 mL). The filtrate was dried over sodium sulfate. The filtered organic layer was concentrated under vacuum which gave an oil. Weight: 74 mg. Weight yield: 79%. While TLC analysis showed only a single spot, $^1$H-NMR and GC analysis indicated that the isolated material was a mixture of two primary components that co-eluted by TLC. $^1$H-NMR (400 MHz, CDCl$_3$) indicated the presence of peaks corresponding to the isoperillyl alcohol (7) along with an unknown impurity. MS (APCI method): m/e: 153 (M$^{+1}$, 40%), 152 (M$^+$, 13%), 135.09 (M—OH). The other peaks at M+: 169.03 (10%), 255.20, (13%), 285.25 (15%), 287.19 (70%), 290 (68%), & 397.24 (15%) were not characterized. GC analysis confirmed the presence of isoperillyl alcohol (20.5%, (AUC)), compared with the iso-POH obtained from the epoxide route along with the unknown impurity (67.5%, (AUC)).

Example 16

Synthesis of Iso-POH Conjugated with Temozolamide (TMZ)

The reaction scheme is the following:

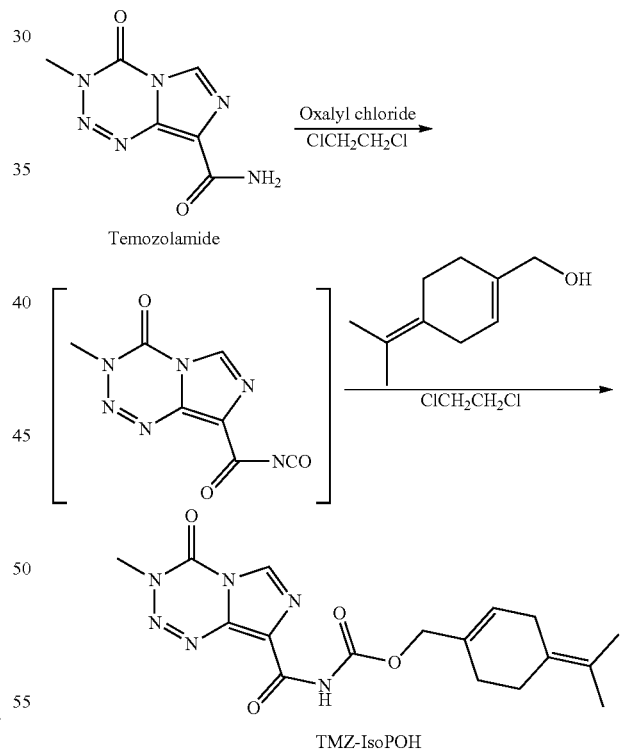

Preparation of (3-Methyl 4-oxo-3,4-dihydroimidazo [5,1-d][1,2,3,5]tetrazine-8-carbonyl)-carbamic Acid-4-isopropylidene cyclohex-1-enylmethyl Ester Oxalyl chloride (0.26 g, 2.0 mmol) will be added slowly to a mixture of Temozolamide (Source: OChem Incorporation, Lot #0711185A, 0.2 g, 1.0 mmol) in 1,2-dichloroethane (15 mL) over a period of 5 min while maintaining the temperature at 10° C. under $N_2$. The reaction mixture will be allowed to warm to room temperature and then heated to reflux for 2.5 h. The excess of oxalyl chloride and 1,2-dichloroethane will be removed by concentration under vacuum. The resulting residue will be redissolved in 1,2-dichloroethane (20 mL) and the reaction mixture cooled to 5° C. under $N_2$. A solution of isoperillyl alcohol (0.17 g, 1.12 mmol) in 1,2-dichloroethane (5 mL) will be added over a period of 10 min. The reaction mixture will be allowed to warm to room temperature and stirred for 12 h. 1,2-Dichloroethane will be concentrated under vacuum to give a residue which will be triturated with hexanes. The resulting pale yellow solid will be filtered and washed with hexanes.

Example 17

Synthesis of Iso-POH Conjugated with Rolipram

The reaction scheme is as follows.

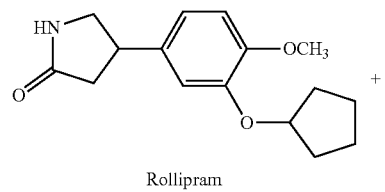

Rollipram

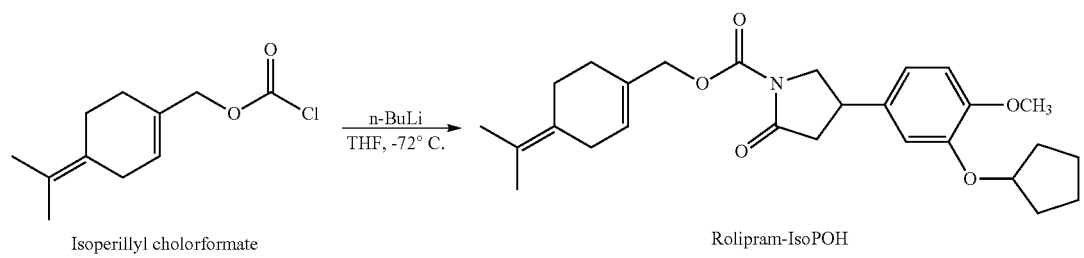

Isoperillyl cholorformate

Rolipram-IsoPOH

Phosgene
Toluene

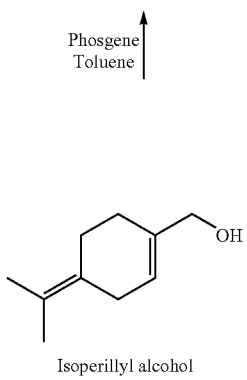

Isoperillyl alcohol

Preparation of 4-(3-Cyclopentyloxy-4-methoxyphenyl)-2-oxo-pyrrolidine-1-carboxylic Acid 4-isopropylidene cyclohex-1-enylmethyl Ester Phosgene (20% in toluene, 19.5 ml, 39.4 mmol) will be added to a mixture of isoperillyl alcohol (3.0 g, 19.7 mmol) and potassium carbonate (8.1 g, 58.6 mmol) in dry toluene (45 mL) over a period of 45 min while maintaining the temperature between 10-12° C. The reaction mixture will be allowed to warm to room temperature and stirred for 10 h under $N_2$. The reaction mixture will be quenched with water (40 mL) and the organic layer separated. The aqueous layer will be extracted with toluene (30 mL) and the combined organic layer washed with water (40 mL×2), brine (10%, 40 mL), and dried over sodium sulfate (25 g). The filtered organic layer will be concentrated under vacuum to give isoperillyl chloroformate as an oil.

Butyl lithium (2.5 M, 0.36 mL, 0.90 mmol) will be added to a solution of rolipram (Source: GL synthesis. Inc. Lot #GLS-SH-110809; 0.2 g, 0.72 mmol) in dry THF (8 mL) at −72° C. over a period of 10 min under $N_2$. After the reaction mixture being stirred for 1.0 h at −72° C., isoperillyl chloroformate (0.16 g, 0.76 mmol, dissolved in 4 mL THF) will be added over a period of 10 min while maintaining the temperature at −72° C. The reaction mixture will be stirred for 3 h and quenched with saturated ammonium chloride (10 mL). The reaction mixture will be allowed to warm to room temperature and extracted with ethyl acetate (2×20 mL). The combined organic layer will be washed with water (20 mL), brine (10%, 25 mL), and dried over sodium sulfate. The filtered organic layer will be concentrated to give an oil which will be purified by column chromatography [Column dimensions: dia: 1.5 cm, height: 15 cm, silica: 230-400 mesh] and eluted with a mixture of 5% ethyl acetate/hexanes (120 mL) followed by 10% ethyl acetate/hexanes (150 mL). The 10% ethyl acetate/hexanes fractions will be combined and concentrated under vacuum to give a gummy solid.

Example 18

Synthesis of Dimethyl Celecoxib bis iso-POH Carbamate Conjugate

The reaction scheme is as follows.

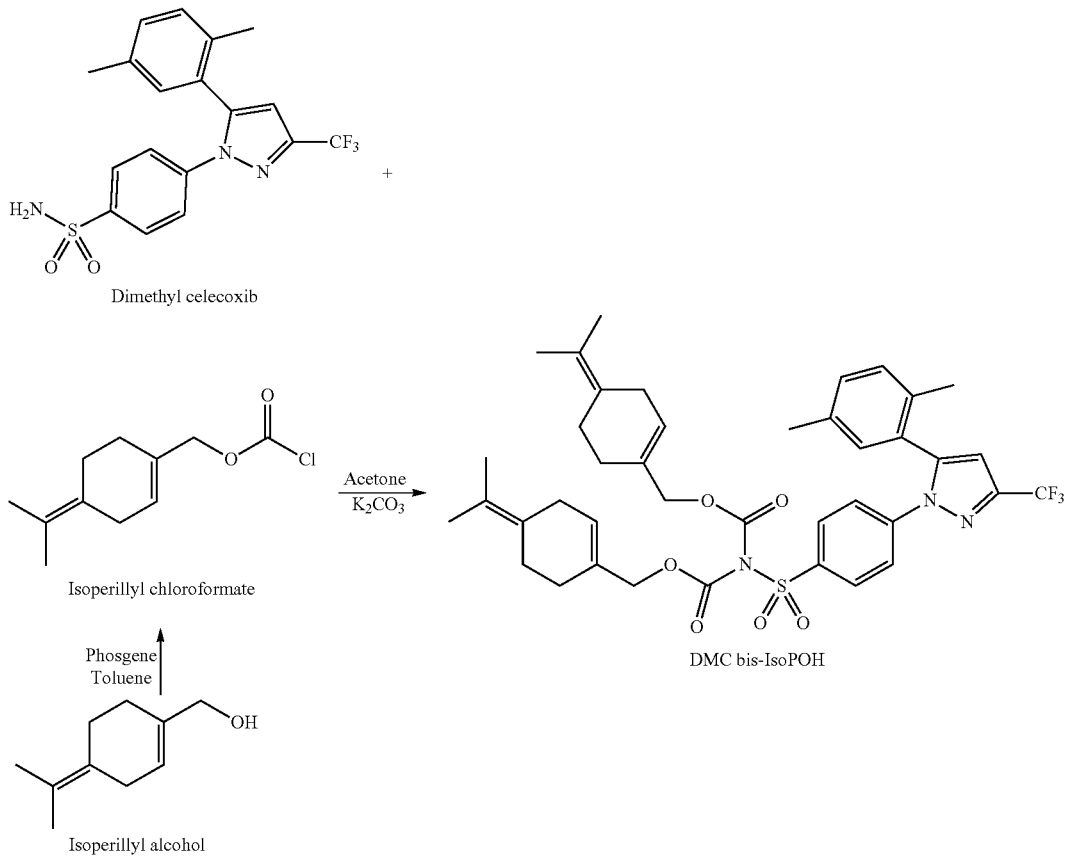

Preparation of 4-(Bis-N,N'-4-isopropylidene cylohex-1-enylmethyloxy carbonyl [5-(2,5-dimethyl phenyl)-3-trifluoromethyl pyrazol-1-yl] benzenesulfonamide Phosgene (20% in toluene, 19.5 ml, 39.4 mmol) will be added to a mixture of isoperillyl alcohol (3.0 g, 19.7 mmol) and potassium carbonate (8.1 g, 58.6 mmol) in dry toluene (45 mL) over a period of 45 min while maintaining the temperature between 10-12° C. The reaction mixture will be allowed to warm to room temperature and stirred for 10 h under $N_2$. The reaction mixture will be quenched with water (40 mL) and the organic layer separated. The aqueous layer will be extracted with toluene (30 mL) and the combined organic layer washed with water (40 mL×2), brine (10%, 40 mL), and dried over sodium sulfate (25 g). The filtered organic layer will be concentrated under vacuum to give isoperillyl chloroformate as an oil.

Isoperillyl chloroformate (0.22 g, 1.0 mmol) will be added slowly to a mixture of dimethyl celecoxib (0.2 g, 0.50 mmol) and potassium carbonate (0.14 g, 1.0 mmol) in dry acetone (25 mL) over a period of 5 min under $N_2$. The reaction mixture will be heated to reflux and maintained for 4 h. The reaction mixture will be cooled and the acetone concentrated under vacuum. The resulting residue will be suspended in water (25 mL) and extracted with ethyl acetate (3×20 mL). The combined organic layer will be washed with water (40 mL), followed by brine (10%, 30 mL), and dried over sodium sulfate. The filtered organic layer will be concentrated under vacuum to give a residue which will be purified by column chromatography [Column dimensions: dia: 1.5 cm, height: 15 cm, silica: 230-400 mesh] and elated with hexanes (100 mL) followed by a mixture of hexanes/ethyl acetate (95:5, 100 mL). The hexane/ethyl acetate fractions will be combined and concentrated under vacuum to give a gummy mass.

Example 19

The Ras Binding Domain (RBD) Pulldown Assay was performed to analyze the active-GTP bound Ras in cell lysates with or without treatments of POH at different concentrations.

NF1 (CRL-2884 cells, human Schwann cell NF1) or Pan1 cells were treated with or without POH for 24 hours, and cells were collected and lysed with lysis buffer.

Cleared lysate was assayed for protein concentration and protein-equalized supernatants were incubated with Raf-1-RBD agarose beads for 1 h at 4° C. Beads were washed four times in the lysis buffer. Bound proteins were dissolved by the addition of 50 μL of Laemmli loading buffer and boiled for 5 minutes. Samples were run on 12.5% SDS-PAGE gels. The amount of active-GTP-Ras in the bound fraction was analyzed by Western blotting by using specific antibody for pan-Ras, H-Ras and K-Ras.

Figure 19:
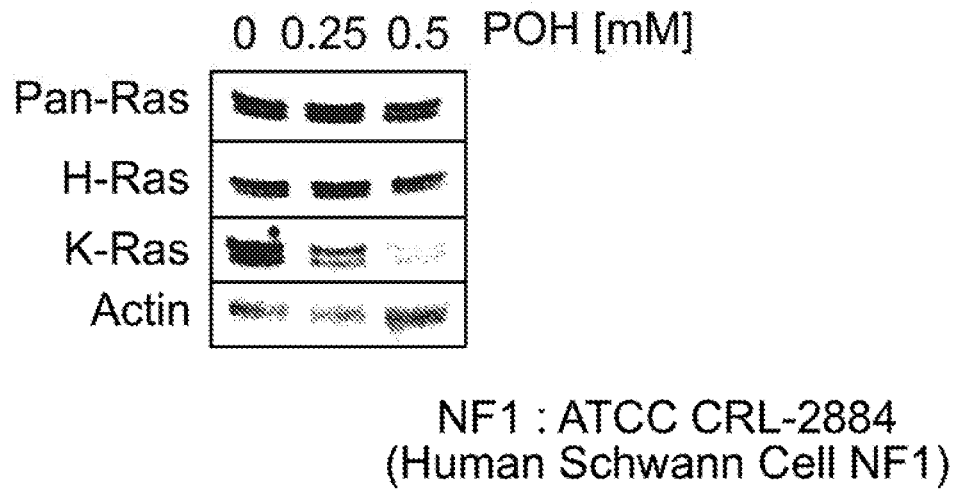
FIG. 19 shows Western blot results from Ras Binding Domain (RBD) Pulldown Assays in lysates of NF1 CRL-2884 cells with or without treatments of POH at different concentrations.

FIG. 19 shows Western blot results from Ras Binding Domain Pulldown Assays in lysates of NF1 CRL-2884 cells with or without treatments of POH at different concentrations. The results show that POH treatment can inhibit or decrease (active) Ras level and/or activity.

Example 20

Figure 20A:
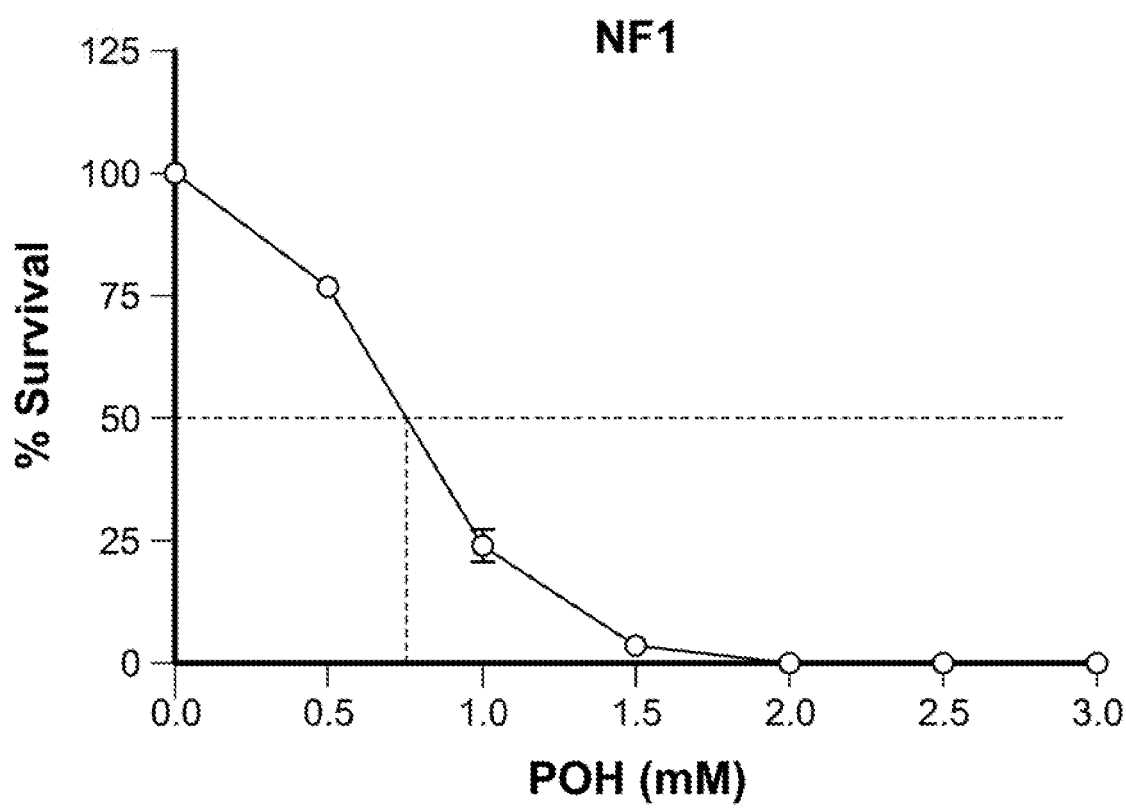
FIGS. 20A-20C show the cytotoxicity of POH and POH conjugated with rolipram (RP-POH) on NF1 CRL-2884 cells or Panel cells.
Figure 20B:
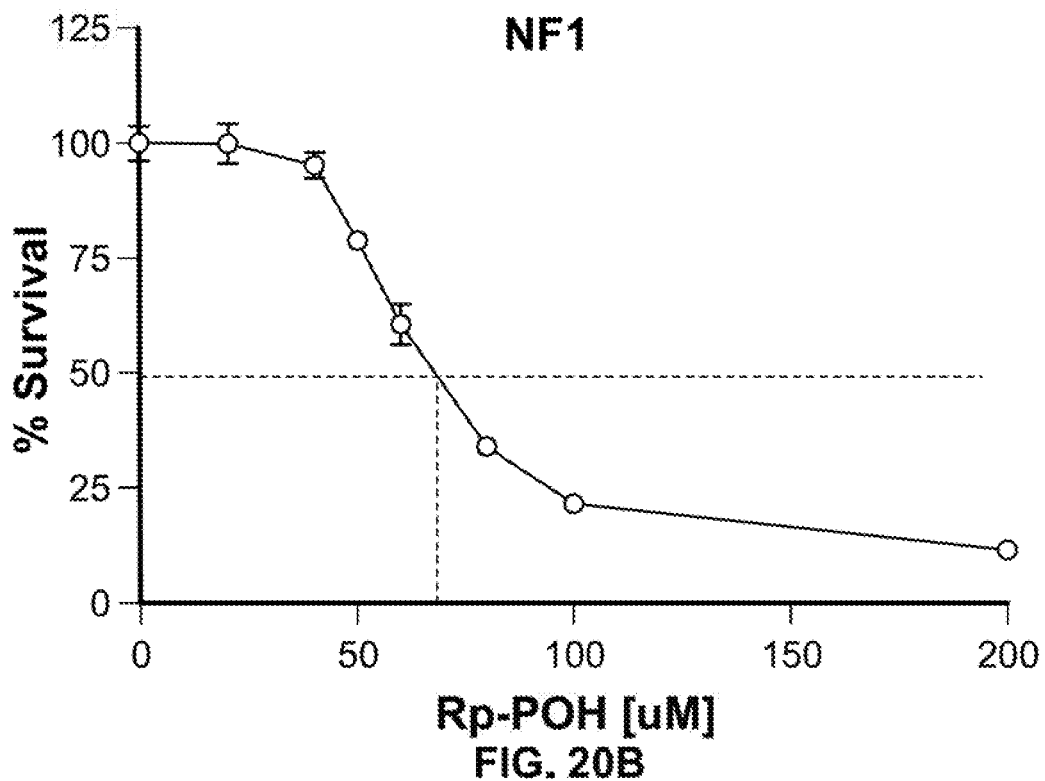
Figure 20C:
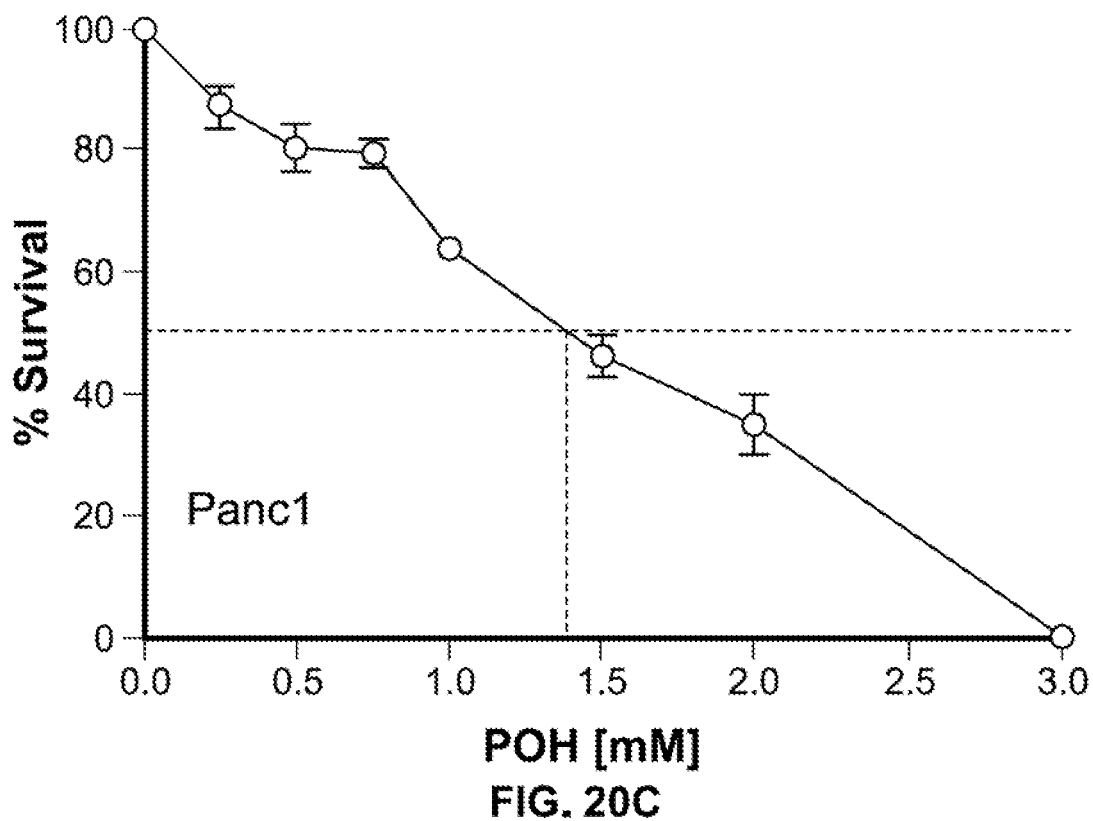

In Vitro Cytotoxicity Studies of Perillyl Alcohol and Rolipram-POH on Neurofibromatosis Cells Both POH and POH conjugated to rolipram (RP-POH) were cytotoxic for neurofibromatosis cells (FIGS. 20A-20C). Panel cells contain mutated K-Ras.

To analyze the viability of cells with drug treatments, NF1 (CRL-2884 cells) or Panc1 cells were seeded (5000 cells/well) in 96-well assay black plates with flat bottoms (Greiner, Germany). After 24 hours, drug was added to the cells at different concentrations, and incubated for 48 hours. The alamar blue assay was performed according to the manufacturer's protocol (Life Technology, Grand Island, N.Y.). Fluorescence was measured using an excitation wavelength of 540-570 nm (peak excitation is 570 nm), emission at 580-610 nm (peak emission is 585 nm). The average fluorescence values of the cell culture medium alone (back ground) were subtracted from the fluorescence values of experimental wells. Percent viability was calculated relative to untreated control cells. All experiments were performed in triplicate.

Example 21

The Ras Binding Domain (RBD) Pulldown Assay was performed to analyze the Active-GTP bound Ras in cell lysates with or without treatments of POH and Iso-POH at different concentrations.

Panc1 Cells were treated with or without POH or Iso-POH for 24 hr, and cells were collected and lysed with lysis buffer.

Cleared lysate was assayed for protein concentration and protein-equalized supernatants were incubated with Raf-1-RBD agarose beads for 1 h at 4° C. Beads were washed four times in the lysis buffer. Bound proteins were dissolved by the addition of 50 uL of Laemmli loading buffer and boiled for 5 minutes. Samples were run on 12.5% SDS-PAGE gels. The amount of active-GTP-Ras in the bound fraction was analyzed by Western blotting by using specific antibodies for K-Ras or Pan-Ras. FIG. 21A shows Western blot results from Ras Binding Domain Pulldown Assays in lysates of Panc1 cells with or without treatments of POH and iso-POH. FIGS. 21B and 21C are bar graphs quantifying the K-Ras level (FIG. 21B) and Pan-Ras level (FIG. 21C) from the Western blot results of the Ras Binding Domain Pulldown Assays in lysates of Panc1 cells with or without treatments of POH and iso-POH. All the blots were normalized to actin control and each protein expression was calculated as % of control.

The results show that POH or iso-POH treatment can inhibit or decrease (active) Ras level and/or activity.

Example 22

Figure 22A:
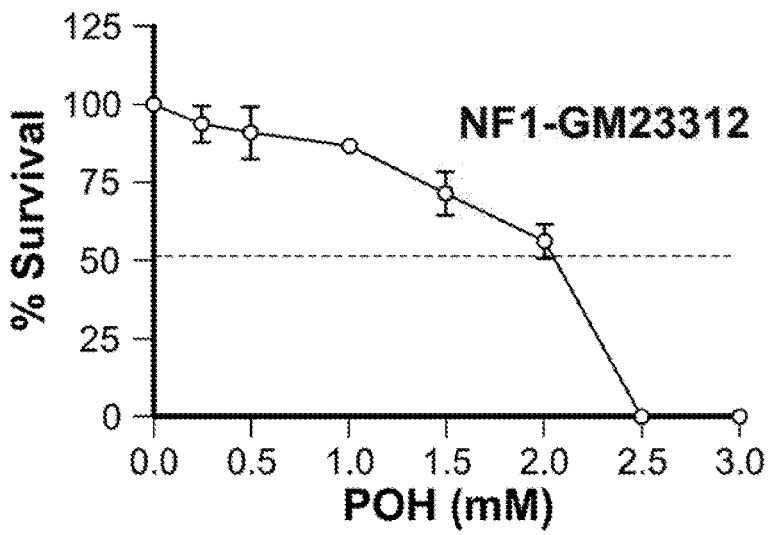
FIGS. 22A-22C show the cytotoxicity of POH (FIG. 22A), iso-POH (FIG. 22B) and RP-POH (FIG. 22C) on NF1-GM23312 cells.
Figure 22B:
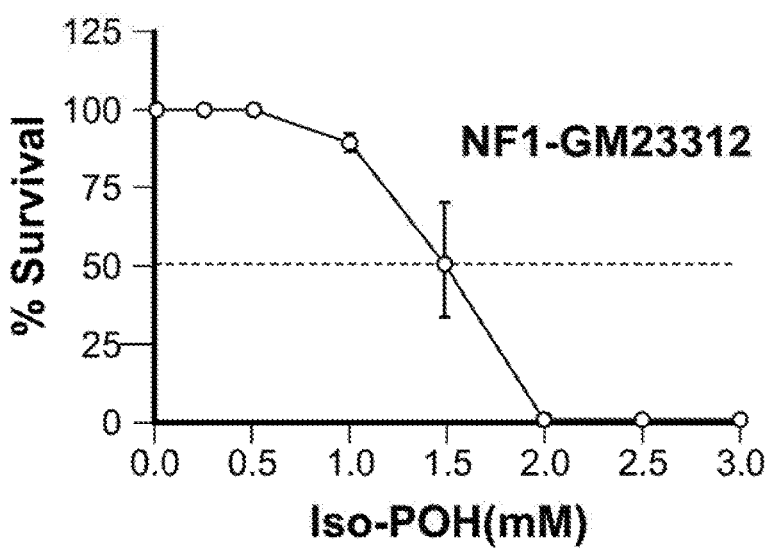
Figure 22C:
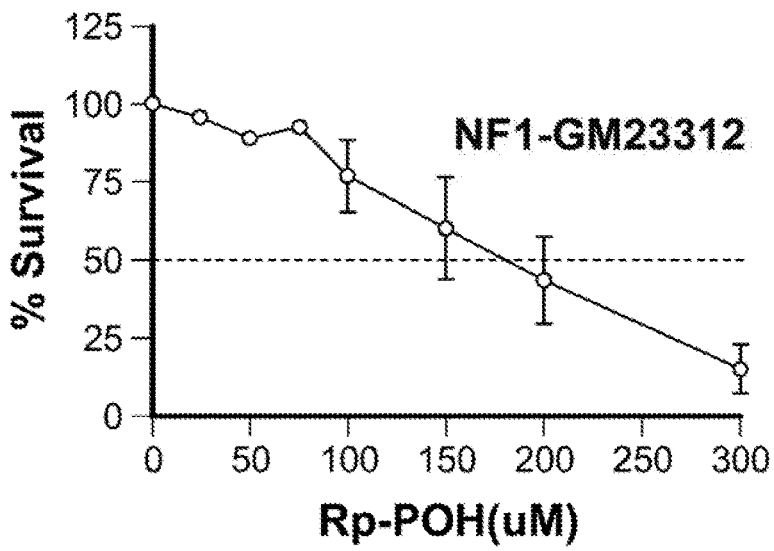

FIGS. 22A-22C show the cytotoxicity of POH, iso-POH and RP-POH (POH conjugated to rolipram) on NF1-GM23312 cells. GM23312 cells (Coriell Institute for Medical Research) are malignant peripheral nerve sheath tumor (MPNST) cells.

To analyze the viability of cells with drug treatments, NF1-GM23312 cells were seeded (5000 cells/well) in 96-well assay black plates with flat bottoms (Greiner, Germany). After 24 hours, drug was added to the cells at different concentrations, and incubated for 48 hours. The alamar blue assay was performed according to the manufacturer's protocol. All experiments were performed in triplicate.

FIGS. 23A-23C show the cytotoxicity of POH, iso-POH and RP-POH on NF1-MPNST 26T cells.

NF1-MPNST 26T cells were seeded (5000 cells/well) in 96-well assay black plates with flat bottom (Greiner, Germany). After 24 hours, POH, Iso-POH and RP-POH were added to the cells at different concentrations, and incubated for 48 hours. The alamar blue assay was performed according to the manufacturer's protocol. All experiments were performed in triplicate.

Example 23

Figure 24:
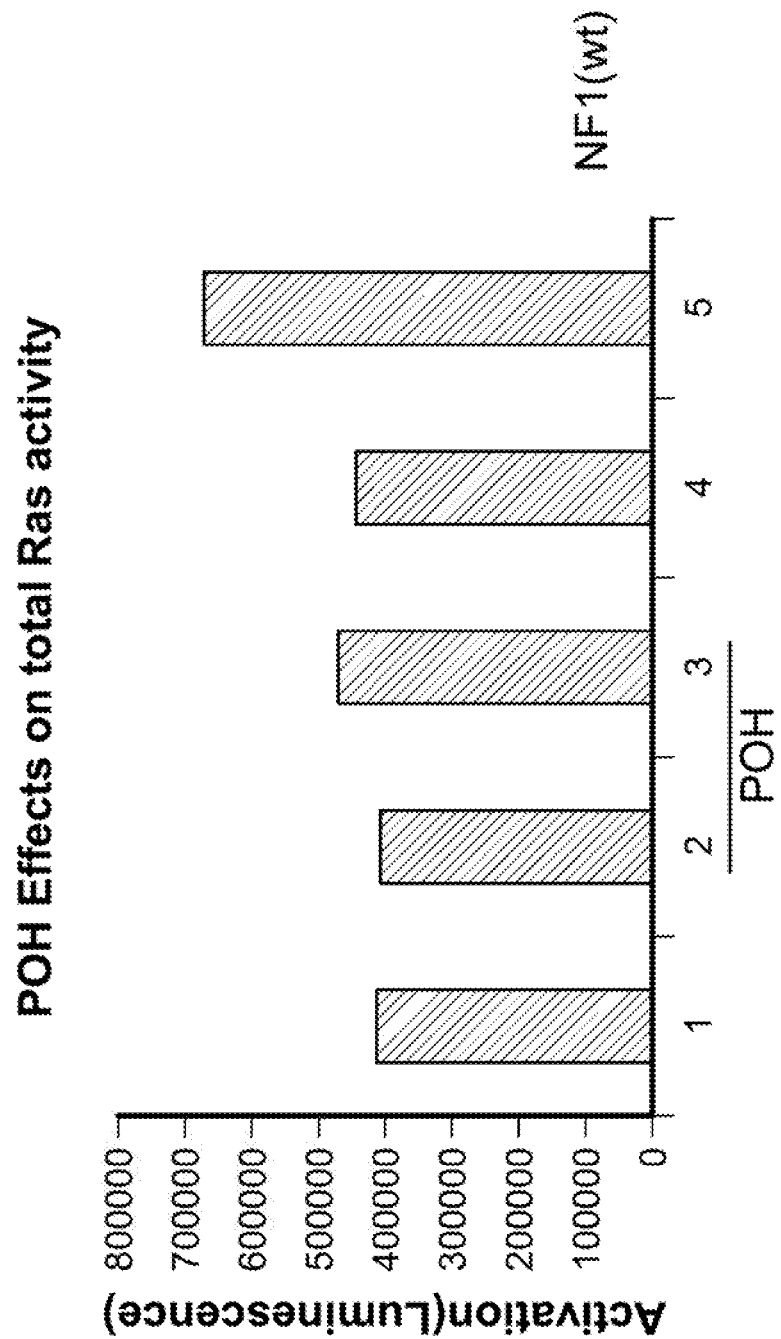
FIG. 24 shows POH effects on total Ras activity. 1: Normal medium (control). 2: 0.5 mM POH treated for 20 hr. 3: 1.0 mM POH treated for 20 hr. 4: 20 µM Farnesyltransferase inhibitor (FTI) treated for 20 hr. 5: positive control.

FIG. 24 shows POH effects on total Ras activity, using Ras activation ELISA assay. Specifically, NF1 cells (e.g., CRL-2884, human Schwann cell NF1) are cultured to approximately 85-90% confluency. NF1 cells were treated with perillyl alcohol (POH) or Farnesyltransferase inhibitor (FTI) for 20 hrs. Cultured media was removed and cells were washed twice with ice-cold PBS (Phosphate Buffered Saline). Cells were scraped from the plate and cell pellets collected. Then IX $Mg^{2+}$ Lysis/Wash buffer with protease and phosphatase inhibitor cocktail was added to the cell pellet. The pellet was resuspended in the buffer and and incubated on ice for 15 minutes. The sample was centrifuged at 14000 rpm for 10 minutes at 4° C. in a microcentrifuge. The supernatant was collected and protein concentration calculated. Cell lysates having 100 μg or 50 μg protein were used and ELISA was performed according to the manufacturer's protocol (Millipore Co., Billerica, Mass.).

In FIG. 24, No. 1: Normal medium (control); No. 2: 0.5 mM POH treated for 20 hr; No. 3: 1.0 mM POH treated for 20 hr; No. 4: 20 μM Farnesyltransferase inhibitor (FTI) treated for 20 hr; No. 5: positive control.

Example 24

Figure 25A:
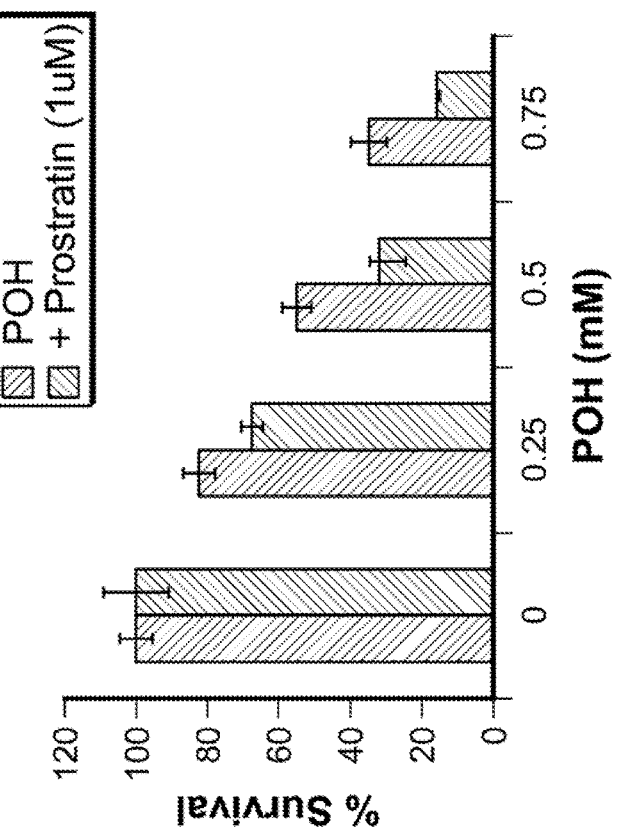
FIGS. 25A-25C show the cytotoxicity of POH, POH in combination with prostratin (FIG. 25A), and prostratin (FIG. 25B) on NF1-MPNST 26T cells.
Figure 25B:
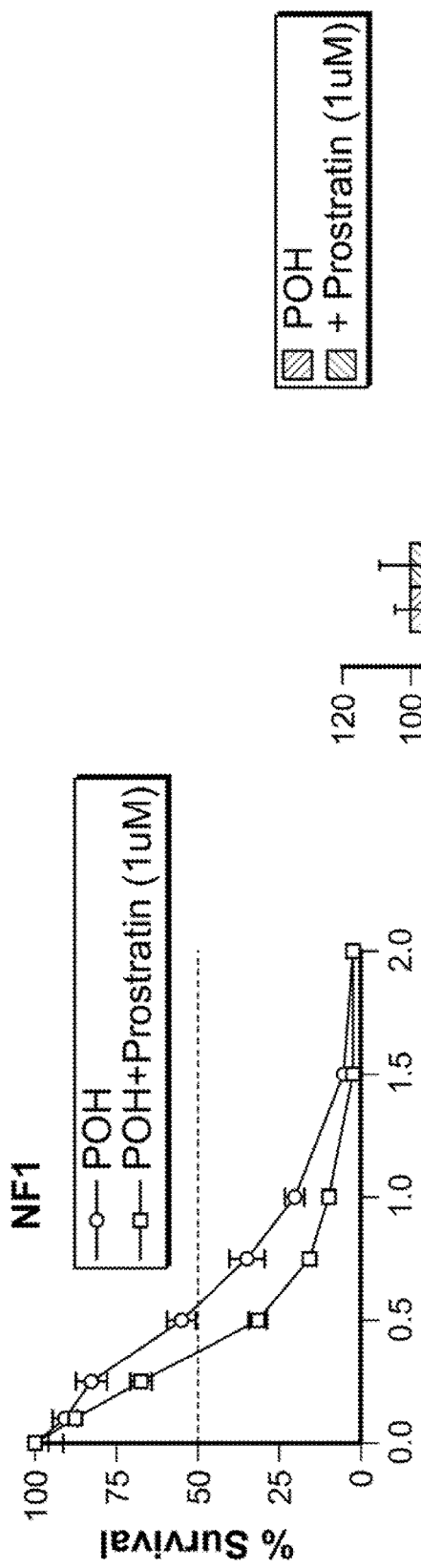
Figure 25C:
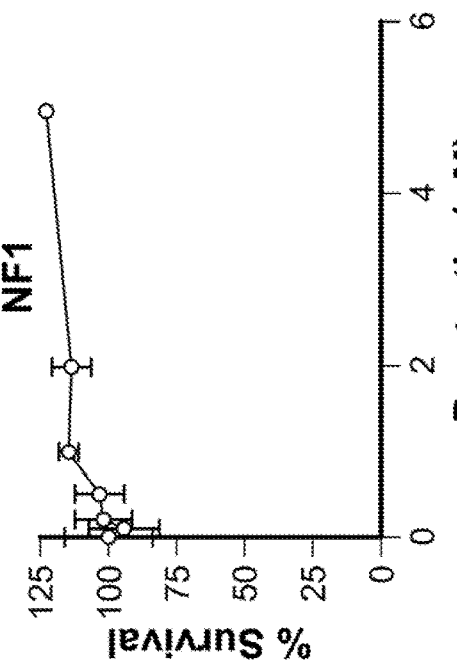

A combination of POH and prostratin was more cytotoxic for neurofibromatosis cells than POH alone or prostratin alone (FIGS. 25A-25C).

Similarly, a combination of POH and lovastatin was more cytotoxic for neurofibromatosis cells than POH alone or lovastatin alone (FIGS. 26A-26C).

NF1 cells (e.g., CRL-2884, human Schwann cell NF1) were used for the experiments shown in FIGS. 25A-25C and 26A-26C.

Example 25

Intracellular Calcium Levels After POH Treatment

Free intracellular calcium was determined by using Fluo-3AM (Invitrogen). U251 cells were seeded on coverslips the day before the experiment and treated with POH (1 mM or 1.5 mM) for 20 hours. Cells were then stained with Fluo-3 dye containing medium for 1 hour at 37° C. The dye was then washed out with dye-free media and fixed with 3.7% formaldehyde for 30 min. Coverslips were mounted on glass slides; and intracellular calcium levels were determined by monitoring intracellular fluorescence by fluorescence microscopy.

Figure 27:
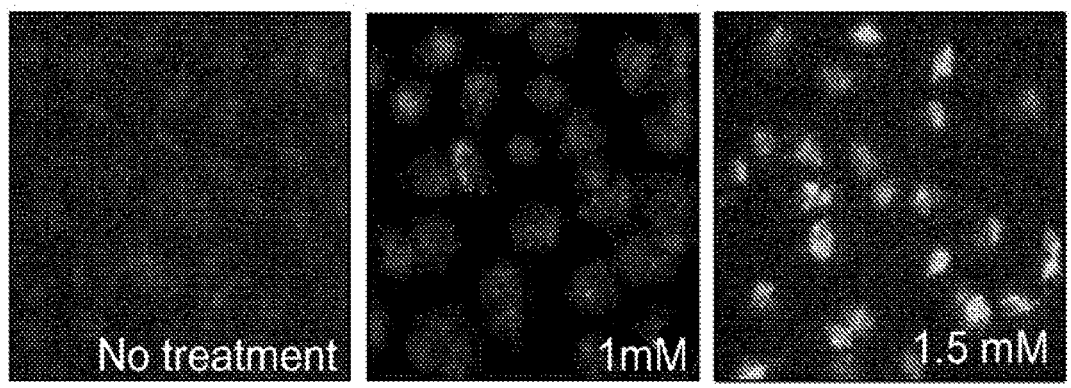
FIG. 27 shows intracellular calcium levels after POH treatment.

FIG. 27 shows that POH treatment can increase (free) intracellular calcium levels.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. A method of treating neurofibromatosis, comprising administering to a subject a therapeutically effective amount of perillyl alcohol, an iso-perillyl alcohol, or a combination thereof.

2. A method of treating neurofibromatosis, comprising administering to a subject a therapeutically effective amount of a carbamate of perillyl alcohol, a carbamate of an iso-perillyl alcohol, or a combination thereof, wherein the carbamate of perillyl alcohol is perillyl alcohol conjugated with temozolomide, rolipram or dimethyl celecoxib, and wherein the carbamate of an iso-perillyl alcohol is an iso-perillyl alcohol conjugated with temozolomide, rolipram or dimethyl celecoxib.

3. The method of claim 2, wherein the carbamate of perillyl alcohol is 4-(3-cyclopentyloxy-4-methoxy phenyl)-2-oxo-pyrrolidine-1-carboxylic acid 4-isopropenyl cyclohex-1-enylmethyl ester.

4. The method of claim 2, wherein the carbamate of perillyl alcohol is 3-methyl 4-oxo-3,4-dihydroimidazo[5,1-d][1,2,3,5]tetrazine-8-carbonyl-carbamic acid-4-isopropenyl cyclohex-1-enylmethyl ester.

5. The method of claim 1 or 2, further comprising administering temozolomide, dimethyl celecoxib, or rolipram to the subject.

6. The method of claim 1 or 2, further comprising administering to the subject a statin selected from the group consisting of atorvastatin, fluvastatin, lovastatin, pitavastatin, pravastatin, simvastatin and rosuvastatin.

7. The method of claim 1 or 2, further comprising administering prostratin to the subject.

8. The method of claim 1 or 2, wherein the administration is by inhalation, intranasally, orally, intravenously, subcutaneously or intramuscularly.

9. A method of inhibiting or decreasing Ras level and/or activity in a cell or in a subject, comprising administering to the cell or the subject a carbamate of perillyl alcohol, a carbamate of an iso-perillyl alcohol, or a combination thereof, wherein the carbamate of perillyl alcohol is perillyl alcohol conjugated with temozolomide, rolipram or dimethyl celecoxib, and wherein the carbamate of an iso-perillyl alcohol is an iso-perillyl alcohol conjugated with temozolomide, rolipram or dimethyl celecoxib.

10. The method of claim 9, wherein the carbamate of perillyl alcohol is 4-(3-cyclopentyloxy-4-methoxy phenyl)-2-oxo-pyrrolidine-1-carboxylic acid 4-isopropenyl cyclohex-1-enylmethyl ester.

11. The method of claim 9, wherein the perillyl alcohol carbamate is 3-methyl 4-oxo-3,4-dihydroimidazo[5,1-d][1,2,3,5]tetrazine-8-carbonyl-carbamic acid-4-isopropenyl cyclohex-1-enylmethyl ester.

12. The method of claim 9, further comprising administering temozolomide, dimethyl celecoxib, or rolipram.

13. The method of claim 9, further comprising administering a statin selected from the group consisting of atorvastatin, fluvastatin, lovastatin, pitavastatin, pravastatin, simvastatin and rosuvastatin.

14. The method of claim 9, further comprising administering prostratin.

15. The method of claim 9, wherein said administration is by inhalation, intranasally, orally, intravenously, subcutaneously or intramuscularly.

16. A method of treating neurofibromatosis, comprising administering to a subject a therapeutically effective amount of perillyl alcohol.

17. The method of claim 16, further comprising administering rolipram to the subject.

18. The method of claim 16, further comprising administering a statin selected from the group consisting of atorvastatin, fluvastatin, lovastatin, pitavastatin, pravastatin, simvastatin and rosuvastatin.

19. The method of claim 18, wherein the statin is lovastatin.

20. The method of claim 16, further comprising administering prostratin to the subject.

21. A method of treating neurofibromatosis, comprising administering to a subject a therapeutically effective amount of iso-perillyl alcohol.

22. The method of claim 21, further comprising administering rolipram to the subject.

23. The method of claim 21, further comprising administering a statin selected from the group consisting of atorvastatin, fluvastatin, lovastatin, pitavastatin, pravastatin, simvastatin and rosuvastatin.

24. The method of claim 23, wherein the statin is lovastatin.

25. The method of claim 2, wherein the carbamate of perillyl alcohol is 4-bis-N,N'-4-isopropenyl cyclohex-1-enylmethyloxy carbonyl [5-(2,5-dimethyl phenyl)-3-trifluoromethyl pyrazol-1-yl] benzenesulfonamide.

26. The method of claim 9, wherein the carbamate of perillyl alcohol is 4-bis-N,N'-4-isopropenyl cyclohex-1-enylmethyloxy carbonyl [5-(2,5-dimethyl phenyl)-3-trifluoromethyl pyrazol-1-yl] benzenesulfonamide.

27. The method of claim 2, wherein the carbamate of an iso-perillyl alcohol is (3-Methyl 4-oxo-3,4-dihydroimidazo[5,1-d][1,2,3,5]tetrazine-8-carbonyl)-carbamic acid-4-isopropylidene cyclohex-1-enylmethyl ester, 4-(3-Cyclopentyloxy-4-methoxyphenyl)-2-oxo-pyrrolidine-1-carboxylic acid 4-isopropylidene cyclohex-1-enylmethyl ester, or 4-(Bis-N,N'-4-isopropylidene cyclohex-1-enylmethyloxy carbonyl [5-(2,5-dimethyl phenyl)-3-trifluoromethyl pyrazol-1-yl] benzenesulfonamide.

28. The method of claim 9, wherein the carbamate of an iso-perillyl alcohol is (3-Methyl 4-oxo-3,4-dihydroimidazo[5,1-d][1,2,3,5]tetrazine-8-carbonyl)-carbamic acid-4-isopropylidene cyclohex-1-enylmethyl ester, 4-(3-Cyclopentyloxy-4-methoxyphenyl)-2-oxo-pyrrolidine-1-carboxylic acid 4-isopropylidene cyclohex-1-enylmethyl ester, or 4-(Bis-N,N'-4-isopropylidene cyclohex-1-enylmethyloxy carbonyl [5-(2,5-dimethyl phenyl)-3-trifluoromethyl pyrazol-1-yl] benzenesulfonamide.

* * * * *